US010537884B2

(12) United States Patent
Levy et al.

(10) Patent No.: US 10,537,884 B2
(45) Date of Patent: Jan. 21, 2020

(54) HIERARCHICAL ALUMINOPHOSPHATES AS CATALYSTS FOR THE BECKMANN REARRANGEMENT

(71) Applicant: AdvanSix Resins & Chemicals LLC, Parsippany, NJ (US)

(72) Inventors: Alan B. Levy, Randolph, NJ (US); Robert Raja, Fair Oak (GB); Stephanie H. Newland, Kintbury (GB); Scott R. Keenan, Marlton, NJ (US); Simon R. Bare, Naperville, IL (US)

(73) Assignees: AdvanSix Resins & Chemicals LLC, Parsippany, NJ (US); University of Southampton, Southampton (GB)

( * ) Notice: Subject to any disclaimer, the term of this patent is extended or adjusted under 35 U.S.C. 154(b) by 0 days.

(21) Appl. No.: 16/161,662

(22) Filed: Oct. 16, 2018

(65) Prior Publication Data

US 2019/0046963 A1 Feb. 14, 2019

Related U.S. Application Data

(63) Continuation of application No. 14/953,800, filed on Nov. 30, 2015, now abandoned.

(60) Provisional application No. 62/092,471, filed on Dec. 16, 2014.

(51) Int. Cl.
| | | |
|---|---|---|
| *B01J 29/06* | (2006.01) | |
| *B01J 29/84* | (2006.01) | |
| *C07D 225/02* | (2006.01) | |
| *C07D 223/10* | (2006.01) | |
| *B01J 29/85* | (2006.01) | |
| *B01J 29/89* | (2006.01) | |
| *B01J 35/10* | (2006.01) | |
| *C01B 37/08* | (2006.01) | |
| *C01B 39/54* | (2006.01) | |
| *B01J 29/04* | (2006.01) | |
| *B01J 37/03* | (2006.01) | |
| *B01J 29/83* | (2006.01) | |

(52) U.S. Cl.
CPC ............ *B01J 29/84* (2013.01); *B01J 29/041* (2013.01); *B01J 29/83* (2013.01); *B01J 29/85* (2013.01); *B01J 29/89* (2013.01); *B01J 35/109* (2013.01); *B01J 35/1057* (2013.01); *B01J 35/1061* (2013.01); *B01J 37/03* (2013.01); *C01B 37/08* (2013.01); *C01B 39/54* (2013.01); *C07D 223/10* (2013.01); *C07D 225/02* (2013.01); *B01J 2229/183* (2013.01)

(58) Field of Classification Search
CPC . B01J 29/041; B01J 29/83; B01J 29/84; B01J 29/85; B01J 35/109; B01J 35/1057; B01J 358/1061; B01J 37/03; B01J 37/08; C01B 39/54
USPC .......................................... 502/60, 208, 214
See application file for complete search history.

(56) References Cited

U.S. PATENT DOCUMENTS

| | | | |
|---|---|---|---|
| 4,440,871 | A | 4/1984 | Lok et al. |
| 4,873,325 | A | 10/1989 | Olson |
| 5,292,880 | A | 3/1994 | Apelian et al. |
| 5,942,613 | A | 8/1999 | Carati et al. |
| 6,531,595 | B2 | 3/2003 | Holderich et al. |
| 6,703,501 | B1 | 3/2004 | Kim et al. |
| 6,989,444 | B2 | 1/2006 | Sultana et al. |
| 7,589,841 | B2 | 9/2009 | Schwartz et al. |
| 8,772,476 | B2 | 7/2014 | Levy et al. |
| 8,835,342 | B2 | 9/2014 | Ying et al. |
| 9,221,762 | B2 | 12/2015 | Levy et al. |
| 2005/0197499 | A1 | 9/2005 | Shan et al. |
| 2007/0149778 | A1 | 6/2007 | Zones et al. |
| 2009/0156389 | A1* | 6/2009 | Ryoo ................. B01J 29/40 502/64 |
| 2010/0105893 | A1 | 4/2010 | Okubo et al. |
| 2012/0165558 | A1* | 6/2012 | Ryoo ................. B01J 29/40 549/403 |
| 2013/0109851 | A1 | 5/2013 | Levy et al. |
| 2016/0167030 | A1 | 6/2016 | Levy et al. |
| 2017/0158970 | A1* | 6/2017 | Song ................. B01J 37/04 |

FOREIGN PATENT DOCUMENTS

| | | |
|---|---|---|
| CN | 102897794 A | 1/2013 |
| CN | 103663493 A | 3/2014 |
| EP | 0251168 A2 | 1/1988 |
| IN | 201102418 I1 | 3/2013 |
| KR | 1020170109542 A | 9/2017 |
| RU | 2461424 C2 | 10/2011 |
| RU | 2609779 C2 | 12/2015 |
| WO | 2013063244 A1 | 5/2013 |

OTHER PUBLICATIONS

Sun et al., "Organosilane surfactant-directed synthesis of hierarchical porous SAPO-34 catalysts with excellent MTO performance", Chem Commun. 2014, 50, 6502-6505.*

(Continued)

*Primary Examiner* — Elizabeth D Wood
(74) *Attorney, Agent, or Firm* — Faegre Baker Daniels LLP

(57) ABSTRACT

Methods for producing lactams from oximes by performing a Beckmann rearrangement using a hierarchical porous aluminophosphate catalyst having interconnected microporous and mesoporous networks are provided. Exemplary catalysts include a plurality of weak Brønsted acid active sites, including silicon-containing aluminophosphates having the IZA framework code AFI, such as SAPO-5, CHA, such as SAPO-34, and FAU, such as SAPO-37.

12 Claims, 74 Drawing Sheets

(56) References Cited

OTHER PUBLICATIONS

Choi et al., "Organosilane surfactant-directed synthesis of mesoporous aluminophosphates constructed with crystalline microporous frameworks", Chem. Commun. 2006, pp. 4380-4382.*
Electronic Supplementary Information for Choi et al., 2006, 2 pgs.*
Quiming Sun et al., "Organosilane surfactant-directed synthesis of hierarchical porous SAPO-34 catalysts with excellent MTO performance", Cham Commun. Apr. 30, 2014, 50, 6502-6505.*
Baerlocher, Ch., et al., "AFI" and "CHA." in: Baerlocher, Ch., Atlas of Zeolite Framework Types (New York, Elsevier, 2007), pp. 28-29, 96-97.
Danilina, Nadiya, et al. Active SAPO-5 Catalysts with a Bimodal Pore System. Institute for Chemical and Bioengineering, available at least as early as Oct. 2013, 2 pages.
Danilina, Nadiya, et al., Hierarchical SAPO-5 Catalysts Active in Acid-Catalyzed Reactions. Journal of Catalysis 272:37-43, 2010.
Danilina, Nadiya, et al., Influence of Synthesis Parameters on the Catalytic Activity of Hierarchical SAPO-5 in Space-Demanding Alkylation Reactions. Catalysis Today, 168:80-85, 2011.
Extended European Search Report issued in EP Application 15870717.4, dated Jun. 12, 2018, 10 pages.
International Preliminary Report on Patentability issued in PCT/US2015064696, dated Jun. 29, 2017, 9 pages.
International Search Report and Written Opinion issued in PCT/US2015/064696, dated Jun. 9, 2016, 10 pages.
Jappar, N., et al., Synthesis and Characterization of a New Titanium Silicoaluminophosphate: TAPSO-37. Microporous and Mesoporous Materials, 23:169-178, 1998.
Kong et al., "The Synthesis of Hierarchical SAPO-34 and its Enhanced Catalytic Performance in Chloromethane COnversion to Light Olefins", Catalysis Letters, Springer New York LLC, U.S., vol. 144, No. 9, pp. 1609-1666, Jul. 4, 2014.
Paterson, James, et al., Engineering Active Sites for Enhancing Synergy in Heterogeneous Catalytic Oxidations. Chem. Commun., 47:517-519, 2011.
Potter, Matthew, et al., Role of Isolated Acid Sites and Influence of Pore Diameter in the Low-Temperature Dehydration of Ethanol. ACS Catal., 4:4161-4169, 2014.
Thomas et al., "Design of a "Green" one-step catalytic production of .epsilon.-caprolactam (precursor of nylon-6)", Proceedings of the National Academy of Sciences, National Academy of Sciences, U.S., vol. 102, No. 39, Sep. 27, 2005, pp. 13732-13736.
Verboekend, Danny et al., Hierarchical Silicoaluminophosophates by Post-Synthetic Modification: Influence of Topology, Composition, and Silicon Distribution. Chemistry of Materials, pp. 1-14, Jul. 21, 2014.
Wang, F., et al., Polyethyleneimine templated synthesis of hierarchical SAPO-34 zeolites with uniform mesopores. RSC Advances, 4:46093-46096, 2014.
Wang, J., et al. Tetramethylguanidine-templated synthesis of aluminophosphate-based microporous crystals with AFI-type structure. Microporous and Mesoporous Materials, 117:561-569, 2009.
Yadav et al., "Unique Mesoporous Silicoaluminophosphate Assembled from Faujasite-type SAPO-37 Precursor: A Potential Catalyst for Isomerization", Chemistry Letters, vol. 42, No. 10, Oct. 5, 2013, pp. 1160-1162.
Yin, Chengyang, Synthesis of Hierarchical Porous Silicalite-1 and its Catalytic Performance in Beckmann Rearrangement. Microporous and Mesoporous Materials, 202:133-137, 2015.
Zhou, Lipeng, et al., Synthesis of Hierarchical MeAPO-5 Molecular Sieves—Catalysts for the Oxidation of Hydrocarbons with Efficient Mass Transport Microporous and Mesoporous Materials, 161:76-83, 2012.

* cited by examiner

SAPO-5

SAPO-34

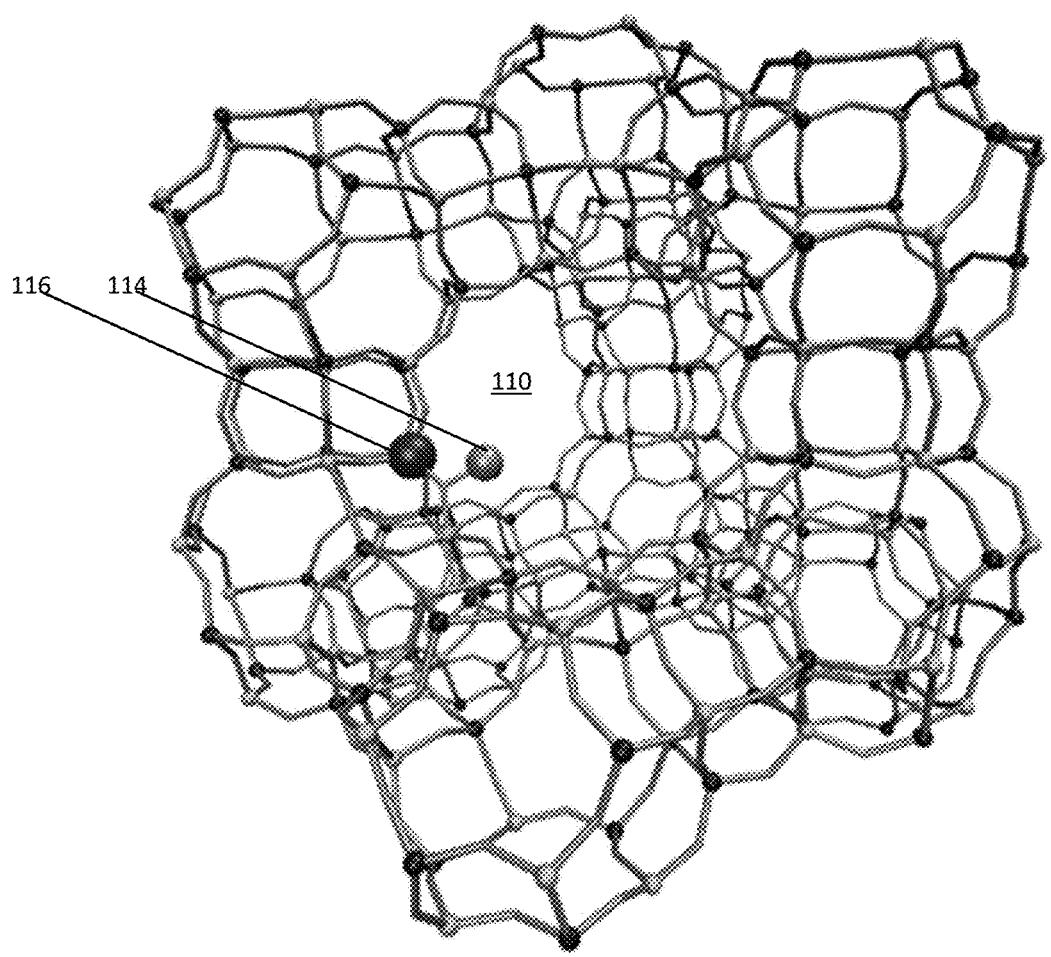
SAPO-37  Figure 4C

```
Initial values  : (Refinement keys on 2nd line)
Zero      Lambda      a           b           c          alpha      beta       gamma      Vol.
   0      1.5406      13.5124     13.5124     8.3871     90         90         120        1326.2
   0      0           1           0           1          0          0          0
Final values    : (Standard errors on 2nd line)
Zero      Lambda      a           b           c          alpha      beta       gamma      Vol.
   0      1.5406      13.5126     13.5126     8.3871     90         90         120        1326.2
   0      0           0.0908      0           0.0074     0          0          0
```

| H | K | L | 2T(Obs) | 2T-Zero | 2Th(Cal) | Dif |
|---|---|---|---------|---------|----------|---------|
| 0 | 1 | 0 | 7.818   | 7.818   | 7.5484   | 0.2696  |
| 1 | 1 | 0 | 13.247  | 13.247  | 13.0933  | 0.1537  |
| 0 | 2 | 0 | 15.273  | 15.273  | 15.1299  | 0.1431  |
| 1 | 2 | 0 | 20.215  | 20.215  | 20.0591  | 0.1559  |
| 0 | 0 | 2 | 21.248  | 21.248  | 21.1691  | 0.0789  |
| 0 | 3 | 0 | 22.788  | 22.788  | 22.7786  | 0.0094  |
| 1 | 1 | 2 | 24.996  | 24.996  | 24.971   | 0.025   |
| 2 | 2 | 0 | 26.292  | 26.292  | 26.3615  | -0.0695 |
| 1 | 2 | 2 | 29.351  | 29.351  | 29.3247  | 0.0263  |
| 0 | 4 | 0 | 30.364  | 30.364  | 30.5319  | -0.1679 |
| 2 | 2 | 2 | 33.99   | 33.99   | 34.0521  | -0.0621 |
| 1 | 3 | 2 | 34.861  | 34.861  | 34.9289  | -0.0679 |
| 0 | 4 | 2 | 37.434  | 37.434  | 37.4518  | -0.0178 |
| 1 | 2 | 3 | 38.0416 | 38.0416 | 38.0469  | -0.0053 |

SAPO-5

Figure 8A

```
Initial values  : (Refinement keys on 2nd line)
Zero      Lambda      a           b           c          alpha      beta       gamma      Vol.
   0      1.5406      13.6494     13.6494     8.3233     90         90         120        1342.9
   0      0           1           0           1          0          0          0
Final values    : (Standard errors on 2nd line)
Zero      Lambda      a           b           c          alpha      beta       gamma      Vol.
   0      1.5406      13.651      13.651      8.3234     90         90         120        1343.3
   0      0           0.0672      0           0.0075     0          0          0
```

| H | K | L | 2T(Obs) | 2T-Zero | 2Th(Cal) | Dif |
|---|---|---|---------|---------|----------|---------|
| 1 | 1 | 0 | 13.113  | 13.113  | 12.96    | 0.153   |
| 0 | 2 | 0 | 15.118  | 15.118  | 14.9756  | 0.1424  |
| 1 | 2 | 0 | 19.954  | 19.954  | 19.8538  | 0.1002  |
| 0 | 0 | 2 | 21.469  | 21.469  | 21.333   | 0.136   |
| 0 | 1 | 2 | 22.628  | 22.628  | 22.6327  | -0.0047 |
| 1 | 1 | 2 | 25.057  | 25.057  | 25.0405  | 0.0165  |
| 2 | 2 | 0 | 26.104  | 26.104  | 26.0896  | 0.0144  |
| 1 | 3 | 1 | 29.246  | 29.246  | 29.2511  | -0.0051 |
| 0 | 4 | 0 | 30.182  | 30.182  | 30.215   | -0.033  |
| 2 | 2 | 2 | 33.836  | 33.836  | 33.9434  | -0.1074 |
| 1 | 4 | 0 | 34.661  | 34.661  | 34.7459  | -0.0849 |
| 0 | 4 | 2 | 37.179  | 37.179  | 37.2857  | -0.1067 |
| 0 | 5 | 0 | 38.0254 | 38.0254 | 38.0267  | -0.0013 |

HP SAPO-5

Figure 8B

```
Initial values  : (Refinement keys on 2nd line)
Zero    Lambda    a        b        c        alpha    beta    gamma    Vol.
  0     1.5406    9.395    9.395    9.395    94.23    94.23   94.23    822.1
  0     0         1         0        0        1        0        0
Final values : (Standard errors on 2nd line)
Zero    Lambda    a        b        c        alpha    beta    gamma    Vol.
  0     1.5406    9.3943   9.3943   9.3943   94.23    94.23   94.23    822
  0     0         0.0405   0        0        0.248    0       0
 H       K        L        2T(Obs)  2T-Zero  2Th(Cal) Dif
 0       0       -1         9.459    9.459    9.4625   -0.0035
 0       1       -1        12.846   12.846   12.8504   -0.0044
 0       1        1        13.826   13.826   13.9231   -0.0971
 0       1        1        13.846   13.846   13.9231   -0.0771
 1       1       -1        15.988   15.988   15.9822    0.0058
 1       1        1        17.659   17.659   17.6968   -0.0378
 0       0       -2        18.974   18.974   18.9904   -0.0164
 0       1       -2        20.578   20.578   20.5606    0.0174
 0       1        2        21.982   21.982   21.9313    0.0507
 1       1       -2        22.383   22.383   22.3525    0.0305
 1       2       -1        23.007   23.007   22.9967    0.0103
 1       1        2        24.878   24.878   24.8346    0.0434
 0       2       -2        25.881   25.881   25.8662    0.0148
 1       2       -2        27.619   27.619   27.5993    0.0197
 0       2        2        28.065   28.065   28.0573    0.0077
 0       3       -1        29.558   29.558   29.4908    0.0672
 1       1       -3        30.583   30.583   30.5526    0.0304
 1       3       -1        31.251   31.251   31.516    -0.265
 2       2       -2        32.321   32.321   32.2864    0.0346
 1       1        3        33.368   33.368   33.3679    0.0001
 1       2       -3        34.438   34.438   34.4442   -0.0062
 0       2        3        35.953   35.953   35.8933    0.0597
 0       0        4        38.583   38.583   38.529     0.054
 1       1       -4        39.6743  39.6743  39.6236    0.0507
```

SAPO-34

Figure 9A

```
Initial values  : (Refinement keys on 2nd line)
Zero    Lambda    a        b        c        alpha    beta    gamma    Vol.
  0     1.5406    9.3684   9.3684   9.3684   94.26    94.26   94.26    815.1
  0     0         1        0        0        1        0        0
Final values : (Standard errors on 2nd line)
Zero    Lambda    a        b        c        alpha    beta    gamma    Vol.
  0     1.5406    9.368    9.368    9.368    94.25    94.25   94.25    815
  0     0         0.0563   0        0        0.494    0       0
 H       K        L        2T(Obs)  2T-Zero  2Th(Cal) Dif
 0       0       -1         9.615    9.615    9.4898   0.1252
 0       1       -1        12.979   12.979   12.8845   0.0945
 1       1       -1        16.143   16.143   16.026    0.117
 1       1        1        17.837   17.837   17.7548   0.0822
 0       0       -2        19.085   19.085   19.0454   0.0396
 0       1       -2        20.734   20.734   20.6165   0.1175
 1       2       -1        23.207   23.207   23.062    0.145
 1       1        2        25.057   25.057   24.9153   0.1417
 0       2       -2        26.015   26.015   25.9355   0.0795
 1       2       -2        27.686   27.686   27.6743   0.0117
 0       2        2        27.953   27.953   28.1454  -0.1924
 1       2        2        30.761   30.761   30.7817  -0.0207
 1       2        2        30.873   30.873   30.7617   0.1113
 2       2       -2        32.209   32.209   32.3766  -0.1676
 1       2       -3        34.349   34.349   34.5379  -0.1889
 2       2        2        35.908   35.908   35.9548  -0.0468
```

HP SAPO-34

Figure 9B

HP SAPO-34

HP SAPO-34

HP SAPO-34

HP SAPO-5

HP SAPO-5

HP SAPO-34

HP SAPO-34

$^{27}$Al MAS NMR spectra of SAPO-5

$^{27}$Al MAS NMR spectra of HP SAPO-5

²⁷Al MAS NMR spectra of SAPO-34    Figure 30A
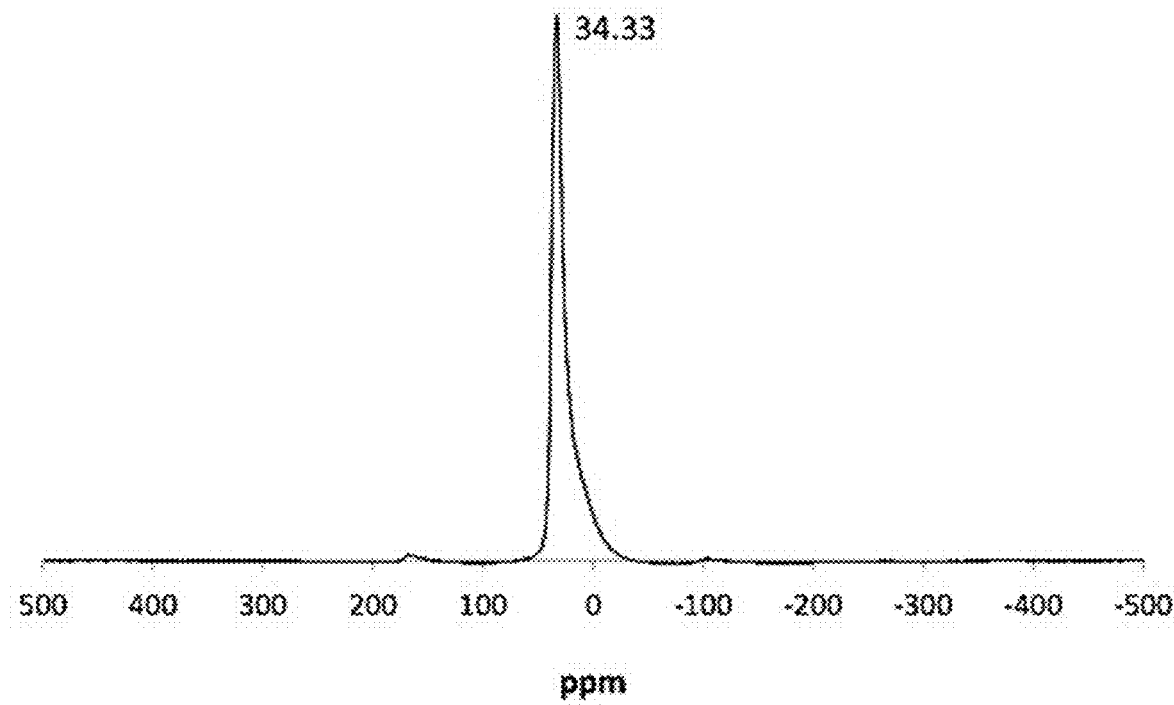
²⁷Al MAS NMR spectra of HP SAPO-34
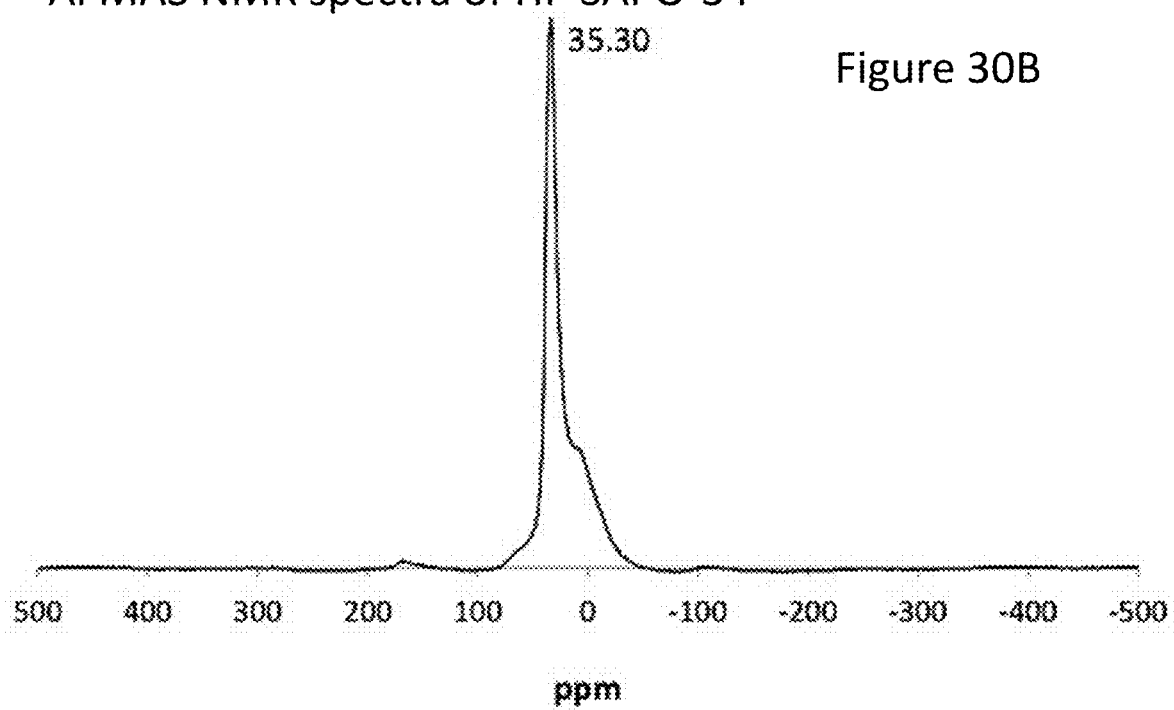
Figure 30B $^{31}$P MAS NMR spectra of SAPO-34

$^{31}$P MAS NMR spectra of HP SAPO-34

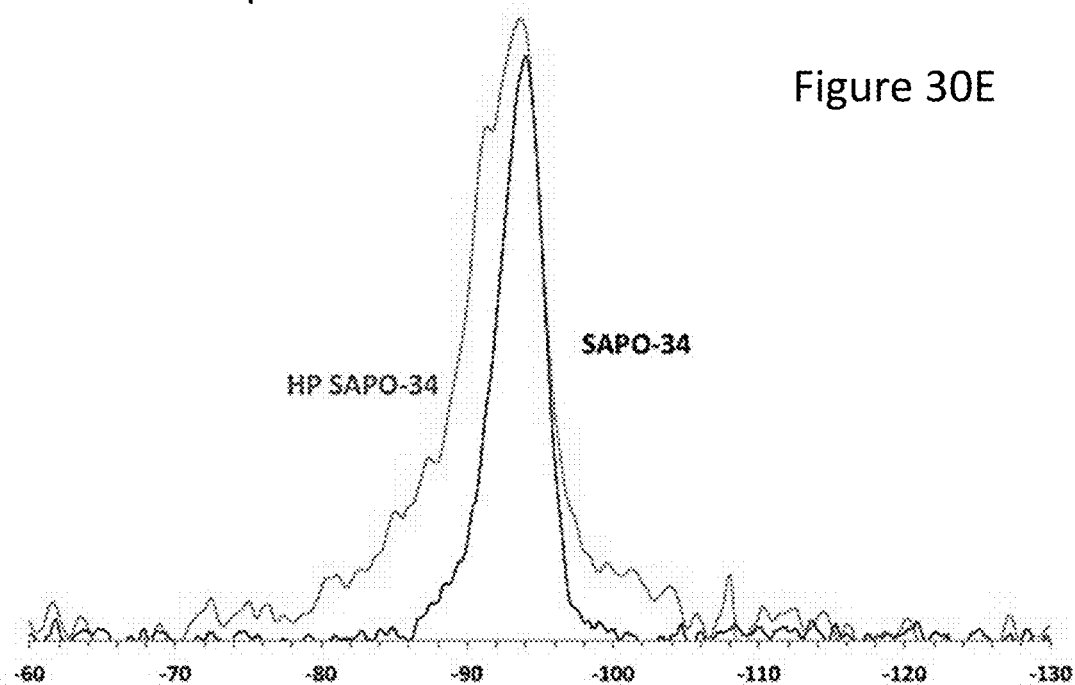
Figure 30E. $^{29}$Si MAS NMR spectra of SAPO-34 and HP SAPO-34

$^{27}$Al MAS NMR spectra of SAPO-37

$^{31}$P MAS NMR spectra of HP SAPO-37

HP SAPO-5

HP SAPO-34

HP SAPO-34
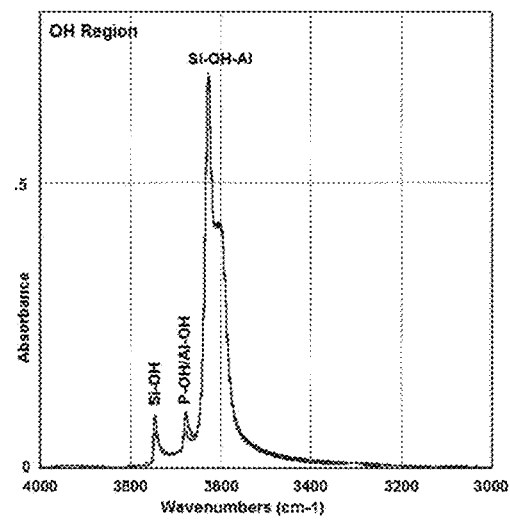
Figure 36A
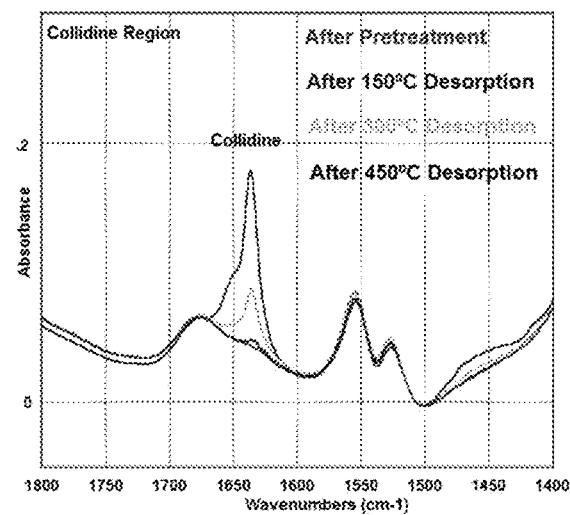
Figure 36B
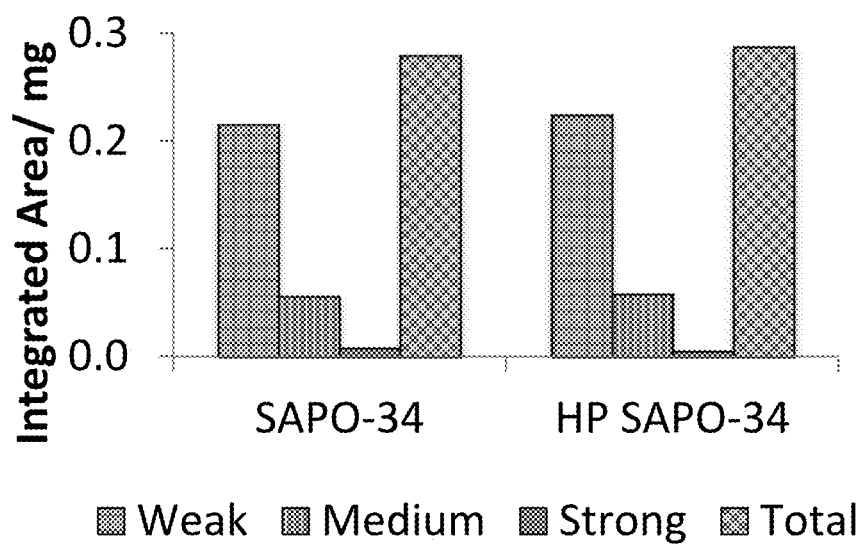

FTIR-CO Difference Spectra (OH region)

HIERARCHICAL ALUMINOPHOSPHATES AS CATALYSTS FOR THE BECKMANN REARRANGEMENT

CROSS-REFERENCE TO RELATED APPLICATIONS

This application is a continuation application of U.S. patent application Ser. No. 14/953,800, filed Nov. 30, 2015, which claims priority under 35 U.S.C. § 119(e) to U.S. Provisional Patent Application No. 62/092,471 entitled HIERARCHICAL ALUMINOPHOSPHATES AS CATALYSTS FOR THE BECKMANN REARRANGEMENT, filed on Dec. 16, 2014, the entire disclosure of which is expressly incorporated by reference herein.

FIELD

The present invention relates to methods of producing lactams, such as ε-caprolactam, for example. In particular, the present invention relates to a method producing ε-caprolactam utilizing aluminophosphate catalysts.

BACKGROUND

Traditional approaches for producing lactams, used in the production of nylon, include an oxime undergoing a Beckmann rearrangement in the presence of an acid catalyst, such as fuming sulfuric acid.

Oximes are compounds having the general formula:

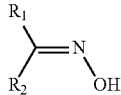

wherein R1 is an organic group and R2 is hydrogen or an organic group. When R2 is hydrogen, the oxime is an oxime derived from an aldehyde, referred to as aldoximes. When R2 is an organic group, the oxime is an oxime derived from a ketone, referred to as ketoximes.

Cyclic oximes are a sub-group of ketoximes having the general formula:

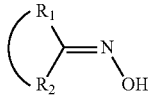

wherein the R1 and R2 groups form a ring.

Lactams, or cyclic amides, are compounds having the general formula:

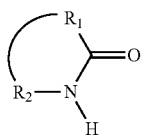

wherein R1 and R2 form a ring.

Exemplary oximes include, but are not limited to, cyclohexanone oxime, cyclododecanone oxime, 4-hydroxy acetophenone oxime and oximes formed from acetophenone, butyraldehyde, cyclopentanone, cycloheptanone, cyclooctanone, and benzaldehyde. Exemplary lactams include those made from cyclic oximes, including those listed above. Lactams are well known in the art as being useful in the production of polyamides, such as nylon. ε-caprolactam can be polymerized to form Nylon-6. ω-laurolactam can be polymerized to form Nylon-12. Additional examples of useful lactams include 11 undecanelactam, a precursor of Nylon-11, 2-Pyrrolidone a precursor of Nylon-4, 2-Piperidone a precursor of Nylon-5.

Exemplary reactions are shown in FIG. 1. As illustrated in FIG. 1A, cyclohexanone oxime is reacted to form ε-caprolactam. ε-caprolactam in turn is polymerized to form nylon-6. As illustrated in FIG. 1B, cyclododecanone oxime is reacted to form ω-laurolactam. ω-laurolactam in turn is polymerized to form nylon-12. As illustrated in FIG. 1C, cyclooctanone oxime is reacted to form the corresponding lactam (caprylolactam), which in turn can be polymerized to form nylon-8. Nylon-6, nylon-8, and nylon-12 are extensively used in industry and manufacturing.

One potential reaction mechanism for the reaction of FIG. 1A is illustrated in FIG. 1D. The mechanism generally consists of protonating the hydroxyl group, performing an alkyl migration while expelling the hydroxyl to form a nitrilium ion, followed by hydrolysis, tautomerization, and deprotonation to form the lactam.

Typically, Beckmann rearrangement reactions of oximes to form lactams are performed using acids such as fuming sulfuric acid. These reactions are characterized by complete or nearly complete conversion of the oxime and very high selectivity for the desired lactams. However, these reactions also produce byproducts including ammonium sulfate. Although ammonium sulfate is a useful product in itself, minimizing its production may be desirable.

Different catalysts, such as zeolites have been proposed for use in optimizing the Beckmann rearrangement. It is widely regarded that weak Brønsted sites are required and as such a range of different microporous catalysts, including zeolites, aluminophosphates (AlPO), metal substituted aluminophosphates (MeAlPO), and mesoporous catalysts, including MCM-41 and SBA-15 have been proposed. Zeolites, such as the highly siliceous MFI zeolite catalyst, ZSM-5, have been used in the gas-phase Beckmann rearrangement of cyclohexanone oxime to ε-caprolactam.

However, typical microporous structures may include one or more disadvantages, including a drop in activity over time due to the formation of carbon deposits on the active sites that act as a poison, reduced mass transfer, diffusion limitations, reduced substrate versatility, and limitations on pore size. Zeotypes having large pores, such as AlPO-8 (AET), VPI-5 (VFI), and cloverite (CLO) may include terminal hydroxyl groups, reducing the stability of the structure. Moreover, these larger pored zeotypes may include strong acid sites, which are less favorable for certain types of reactions, and may not result in increased versatility, longevity, and activity. Mesoporous silicas and isomorphously substituted metals in mesoporous systems, such as Mg-MCM41, Al-MCM41, and MgAl-MCM41, may be less stable, less selective, and less active than microporous catalysts, and their amorphous framework may result in reduced stability.

Improvements in the foregoing processes are desired.

SUMMARY

The present disclosure provides methods for producing lactams from oximes by performing a Beckmann rearrangement using a hierarchical aluminophosphate catalyst. These catalysts are used in reactions to convert oximes into lactams. High conversion of oxime and high selectivity for the desired lactams are produced using the disclosed methods, including improved catalyst longevity, relatively high conversion, and relatively high selectivity for a lactam produced from its corresponding oxime.

In some exemplary embodiments, hierarchical porous aluminophosphate catalysts, such as metal-substituted aluminophosphate materials, are provided. Without wishing to be held to any particular theory, it is believed that the hierarchical porous structure provides a microporous structure with desired weak isolated Brønsted acid active sites and a mesoporous network aiding in mass transfer of reactants and products. The network of mesopores is believed to facilitate access to the active sites in the microporous framework of the material. Additionally, in some exemplary embodiments, the hierarchical porous (HP) AlPO materials have large surface areas and pore volumes compared to a corresponding microporous material due to the secondary porosity of the mesoporous network.

In one exemplary embodiment, a method of performing a Beckmann rearrangement reaction is provided. The method comprises reacting an oxime in the presence of a catalyst to produce a lactam, said catalyst comprising a hierarchical aluminophosphate. In a more particular embodiment, the catalyst comprises a plurality of weak Brønsted acid active sites. In a still more particular embodiment, the catalyst does not include any Lewis acid sites.

In one more particular embodiment of any of the above embodiments, the catalyst comprises a microporous framework and a mesoporous framework. In one exemplary embodiment, the microporous framework and the mesoporous framework are interconnected. In a more particular embodiment of any of the above embodiments, the mesoporous framework having a pore diameter from 15 Å to 50 Å. In one more particular embodiment of any of the above embodiments, the microporous framework having a pore diameter from 3 Å to 10 Å.

In one more particular embodiment of any of the above embodiments, the catalyst is a hierarchical porous aluminophosphate catalyst isomorphously substituted with one or two metals selected from the list consisting of: manganese, iron, copper, magnesium, chromium, cobalt, copper, zinc, silicon, titanium, vanadium, and tin. In a more particular embodiment of any of the above embodiments, the catalyst is a hierarchical porous aluminophosphate catalyst isomorphously substituted with one or two metals selected from the list consisting of: cobalt, silicon, and titanium. In a more particular embodiment of any of the above embodiments, the catalyst is a hierarchical porous aluminophosphate catalyst isomorphously substituted with silicon. In a more particular embodiment of any of the above embodiments, the catalyst is a hierarchical porous aluminophosphate catalyst isomorphously substituted with one or two metals selected from the list consisting of: cobalt and titanium. In a still more particular embodiment, the metal is isomorphously substituted as a Type I or Type II substitution.

In one more particular embodiment of any of the above embodiments, the catalyst comprising a microporous structure having the IZA framework code AFI, CHA, or FAU.

In one more particular embodiment of any of the above embodiments, the catalyst is a hierarchical porous silicoaluminophosphate catalyst. In a still more particular embodiment, the catalyst is selected from the group consisting of: HP SAPO-5, HP SAPO-11, HP SAPO-18, HP SAPO-31, HP SAPO-34, HP SAPO-37, HP SAPO-41, and HP SAPO-44.

In a still more particular embodiment, the catalyst is selected from the group consisting of HP SAPO-5, HP SAPO-34, and HP SAPO-37. In a still more particular embodiment, the catalyst is selected from the group consisting of HP SAPO-5 and HP SAPO-34. In one even more particular embodiment, the catalyst is HP SAPO-5. In another even more particular embodiment, the catalyst is HP SAPO-34. In another even more particular embodiment, the catalyst is HP SAPO-37.

In one more particular embodiment of any of the above embodiments, the catalyst is a hierarchical porous aluminophosphate catalyst selected from the group consisting of HP Co AlPO-5, HP Ti AlPO-5, and HP Co Ti AlPO-5. In one more particular embodiment of any of the above embodiments, the catalyst is HP Co AlPO-5. In one more particular embodiment of any of the above embodiments, the catalyst is HP Ti AlPO-5. In one more particular embodiment of any of the above embodiments, the catalyst is HP Co Ti AlPO-5.

In one more particular embodiment of any of the above embodiments, the oxime is selected from the group consisting of: cyclohexanone oxime, cyclododecanone oxime, 4-hydroxy acetophenone oxime and oximes formed from acetophenone, butyraldehyde, cyclopentanone, cycloheptanone, cyclooctanone, and benzaldehyde. In another more particular embodiment of any of the above embodiments, the lactam is selected from the group consisting of: ε-caprolactam ω-laurolactam 11-undecanelactam, 2-Pyrrolidone, and 2-Piperidone. In one more particular embodiment of any of the above embodiments, the oxime is selected from cyclohexanone oxime, cyclooctanone oxime, and cyclododecanone oxime.

In one more particular embodiment of any of the above embodiments, the reaction is performed in the vapor phase. In another more particular embodiment of any of the above embodiments, the reaction is performed in the liquid phase.

In another embodiment, a hierarchical porous catalyst is provided. The catalyst includes an aluminophosphate framework with the an IZA framework code selected from the group consisting of AFI, CHA, and FAU; a plurality of interconnected micropores, each micropore having a pore diameter from 3 to 10 Å; and a plurality of mesopores interconnected with the micropores, each mesopores having a pore diameter from 15 Å to 50 Å.

In a more particular embodiment, the catalyst is a hierarchical porous aluminophosphate catalyst isomorphously substituted with one or two metals selected from the group consisting of: cobalt, silicon, and titanium.

In a more particular embodiment of any of the above embodiments, the catalyst is a hierarchical porous silicoaluminophosphate catalyst selected from the group consisting of: HP SAPO-5, HP SAPO-34, and HP SAPO-37.

In a more particular embodiment of any of the above embodiments, the catalyst is a hierarchical porous aluminophosphate catalyst isomorphously substituted with one or two metals selected from the group consisting of: cobalt and titanium.

In a more particular embodiment of any of the above embodiments, the catalyst is selected from the group consisting of HP Co AlPO-5, HP Ti AlPO-5, and HP Co Ti AlPO-5.

In a more particular embodiment of any of the above embodiments the catalyst comprises a silicon-containing aluminophosphate framework with the IZA framework code AFI; a plurality of interconnected micropores, each micropore having a pore diameter from 7 to 8 Å; and a plurality of mesopores interconnected with the micropores, each mesopore having a pore diameter from 15 Å to 50 Å.

In a more particular embodiment of any of the above embodiments, the catalyst comprises a silicon-containing aluminophosphate framework with the IZA framework code CHA; a plurality of interconnected micropores, each micropore having a pore diameter from 3 to 4 Å; and a plurality of mesopores interconnected with the micropores, each mesopores having a pore diameter from 15 Å to 50 Å. In another more particular embodiment, the catalyst comprises a aluminophosphate framework with the IZA framework code CHA isomorphously substituted with one or two metals selected from the group consisting of cobalt and titanium; a plurality of interconnected micropores, each micropore having a pore diameter from 3 to 4 Å; and a plurality of mesopores interconnected with the micropores, each mesopores having a pore diameter from 15 Å to 50 Å.

In another more particular embodiment of any of the above embodiments, the catalyst comprises a silicon-containing aluminophosphate framework with the IZA framework code FAU; a plurality of interconnected micropores, each micropore having a pore diameter from 7 to 8 Å; and a plurality of mesopores interconnected with the micropores, each mesopore having a pore diameter from 15 Å to 50 Å.

In a more particular embodiment of any of the above embodiments, the catalyst is phase pure. In another more particular embodiment of any of the above embodiments, the catalyst comprises a plurality of weak Brønsted acid active sites. In still another particular embodiment of any of the above embodiments, the catalyst does not include any Lewis acid sites.

In one exemplary embodiment, a method of producing a hierarchical porous aluminophosphate catalyst is provided. The method includes combining a organosilane surfactant, a structure directing agent, and metal precursors to form a mixture, and adding a silicon source to the mixture. The method further includes crystalizing the resulting material to form a catalyst. In a more particular embodiment of any of the above embodiments, the method further comprising crystalizing the catalyst at a temperature of about 200° C. for about 24 hours.

In a more particular embodiment of any of the above embodiments, the organosilane surfactant is dimethyloctadecyl[(3-(trimethoxysilyl)propyl] ammonium chloride. In a more particular embodiment of any of the above embodiments, the structure directing agent is triethylamine and triethylammonium hydroxide. In a more particular embodiment of any of the above embodiments, the metal precursor is aluminum isopropoxide. In a more particular embodiment of any of the above embodiments, the silicon source is silica. In a more particular embodiment, the hierarchical porous aluminophosphate catalyst is a catalyst according to any of the above embodiments.

The above mentioned and other features of the invention, and the manner of attaining them, will become more apparent and the invention itself will be better understood by reference to the following description of embodiments of the invention taken in conjunction with the accompanying drawings.

BRIEF DESCRIPTION OF THE DRAWINGS

FIG. 4C illustrates a pore diameter of an exemplary microporous SAPO-37 material.

FIG. 8A is related to Example 4, and provides the CellRef refinement values for the SAPO-5 material.

FIG. 8B is related to Example 4, and provides the CellRef refinement values for the HP SAPO-5 material.

FIG. 9A is related to Example 4, and provides the CellRef refinement values for the SAPO-34 material.

FIG. 9B is related to Example 4, and provides the CellRef refinement values for the HP SAPO-34 material.

FIGS. 30A-30E are related to Example 7 and illustrate NMR spectra for SAPO-34 and HP SAPO-34.

FIG. 36A is related to Example 7 and illustrates the collidine adsorption results of HP SAPO-34.

FIG. 36B is related to Example 7 and compares the distribution of acid sites as determined by collidine adsorption in the SAPO-34 and HP SAPO-34 materials.

DETAILED DESCRIPTION

Figure 1A:
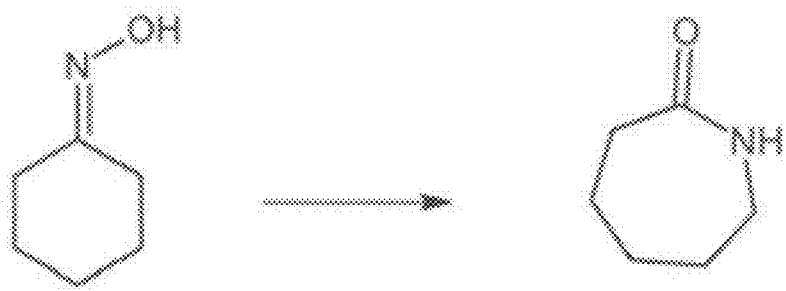
FIG. 1A illustrates the reaction from cyclohexanone oxime to ε-caprolactam.
Figure 1B:
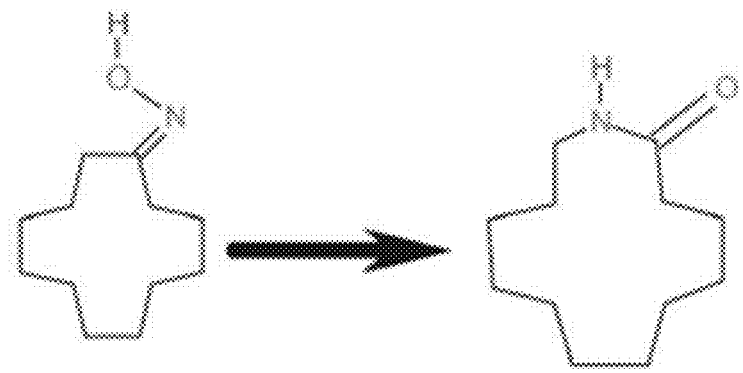
FIG. 1B illustrates the reaction from cyclododecanone oxime to ω-laurolactam.
Figure 1C:
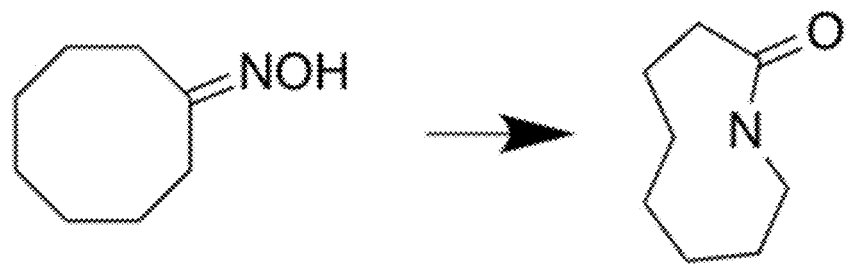
FIG. 1C illustrates the reaction from cyclooctanone oxime to caprylolactam.
Figure 1D:
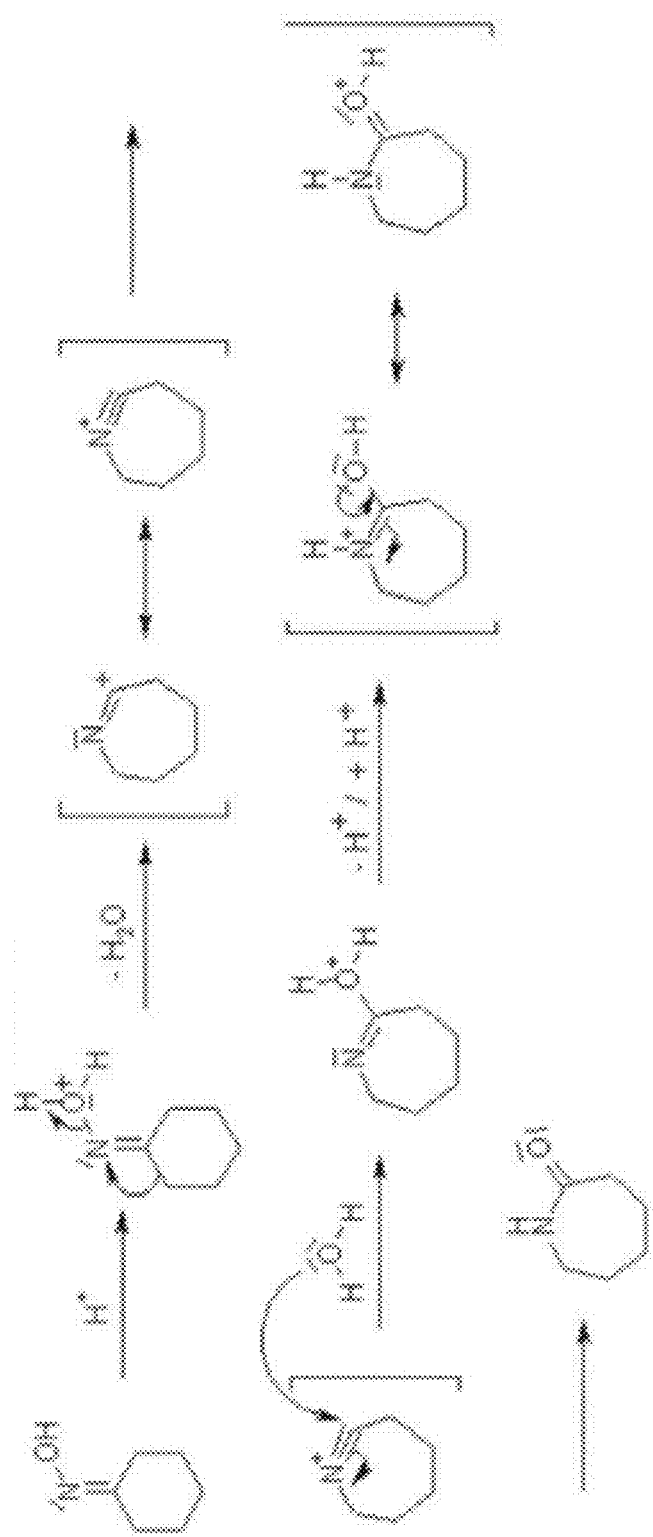
FIG. 1D illustrates the potential steps of a reaction corresponding to a Beckmann rearrangement reaction from cyclohexanone oxime to ε-caprolactam.

The present disclosure is directed to a method to form lactams from cyclic oxime compounds. Exemplary reactions are shown in FIG. 1. As illustrated in FIG. 1A, cyclohexanone oxime is reacted to form ε-caprolactam, which in turn can be polymerized to form nylon-6. As illustrated in FIG. 1B, cyclododecanone oxime is reacted to form ω-laurolactam, which in turn can be polymerized to form nylon-12. As illustrated in FIG. 1C, cyclooctanone oxime is reacted to form caprylolactam, which in turn can be polymerized to form nylon-8. In one exemplary embodiment, a cyclic oxime having from as little as 5, 6, 8, as great as 10, 12, 18, or greater carbon atoms is reacted to form the corresponding oxime.

The present method is also useful to perform other Beckmann rearrangement reactions.

Oximes are converted to lactams, such as in the examples illustrated in FIGS. 1A-1C, through contact with the catalysts. The present disclosure is believed to be generally applicable to any oxime generated from a variety of aldehydes and ketones. Exemplary oximes include, but are not limited, to cyclohexanone oxime, cyclododecanone oxime, 4-hydroxy acetophenone oxime and oximes formed from acetophenone, butryaldehyde, cyclopentanone, cycloheptanone, cyclooctanone, benzaldehyde.

In some exemplary embodiments, the reaction is performed in the absence of a solvent. In some exemplary embodiments, the reaction is performed in the presence of a solvent. In reactions performed in the absence of a solvent, the product is used to absorb the exothermic heat produced by the reaction. In these embodiments, a large ratio of lactam to oxime is maintained in the reaction area to absorb the energy produced by the reaction.

Exemplary solvents include organic nitriles of the formula:

Wherein $R^1$ represents $C_1$-$C_8$-alkyl, $C_1$-$C_8$-alkenyl, $C_1$-$C_8$-alkynyl, $C_3$-$C_8$-cycloalkyl, $C_3$-$C_8$-aralkyl including a $C_6$ aromatic ring. Exemplary nitriles include acetonitrile, benzonitrile and mixtures of any of the foregoing.

Other exemplary solvents include aromatic compounds of the formula:

Wherein Ar is an aromatic ring and $R^2$ represents H, $CH_3$, F, Cl, or Br. The aromatic ring may be substituted with one or more $R^2$ groups. Exemplary aromatic solvents include benzene, toluene, xylene, and chlorobenzene.

Still other exemplary solvents include water and alcohols of the formula:

Wherein $R^3$ represents hydrogen, $C_1$-$C_8$-alkyl, $C_1$-$C_8$-alkenyl, $C_1$-$C_8$-alkynyl, $C_3$-$C_8$-cycloalkyl, $C_3$-$C_8$-arylalkyl. Exemplary alcohols include alcohols of 8 or fewer carbon atoms such as methanol, ethanol, n-propanol, iso-propanol, n-butanol, sec-butanol, iso-butanol, tert-butanol, n-amyl alcohol, n-hexanol, phenol, and mixtures of any of the foregoing.

In exemplary embodiments, the solvent is rigorously dried prior to contact with the catalyst. As used herein, rigorously dried is understood to mean dried to a level of 100 ppm water or less. Exemplary methods of drying include adsorption of water using molecular sieves, such as Activated 4 A molecular sieves. As used herein, a reaction performed in the absence of water means a reaction in which water comprises less than 0.01 wt % of the weight of the reactants.

The reaction is performed as a liquid phase reaction or a gas phase reaction. As used herein, a liquid phase reaction in a reaction in which substantially all of the oxime is in the liquid phase when reacted to form the lactam. As used herein, a gas phase reaction in a reaction in which substantially all of the oxime and solvent is in the gas or vapor phase when reacted to form the lactam.

When performed as a gas phase reaction, the reaction is typically performed at a temperature below 350° C. In a more particular embodiment, the reaction is performed at a temperature from about 130° C. to about 300° C. In still other embodiments, the reaction may be performed at a temperature as low as about 90° C., 100° C., 110° C., 120°, 130°, 135° C., or as high as about 140° C., 150° C., 170° C., 180° C., 190° C., 200° C., 210° C., 220° C., 230° C., 240° C. 250° C., 275° C., 290° C., 300° C., 325° C., 350° C., or within any range defined between any pair of the foregoing values, such as 90° C. to 350° C., 100° C. to 325° C., or 130° C. to 300° C.

When performed as a gas phase reaction, the reaction is typically performed at a pressure from about 0.1 bar to about 1 bar. In some embodiments, a relatively low pressure may be used to provide a high boiling point component in the gas phase without decomposing the component. More particularly, in exemplary embodiments of the reaction performed as a gas phase reaction, the pressure may be as low as 0.005 bar, 0.01 bar, 0.02 bar, 0.05 bar, 0.1 bar, as high as 0.5 bar, 1 bar, 10 bar, or higher, or within a range defined between any pair of the foregoing values, such as 0.005 bar to 10 bar, 0.05 bar to 1 bar, or 0.1 bar to 1 bar.

When performed as a liquid phase reaction, the reaction is typically performed at a temperature beneath 250° C. In a more particular embodiment, the reaction is performed at a temperature from about 100° C. to about 170° C. In still other embodiments, the reaction may be performed at a temperature as low as about 90° C., 100° C., 110° C., 120°, 130°, or as high as about 140° C., 150° C., 170° C., 180° C., 190° C., 200° C., 210° C., 220° C., 230° C., 240° C. 250° C., or within any range defined between any pair of the foregoing values, such as 90° C. to 250° C., 100° C. to 220° C., or 100° C. to 170° C.

When performed as a liquid phase reaction, the reaction is typically performed at a pressure from about 1 bar to about 5 bar. More particularly, in some exemplary embodiments, the pressure may be as low as 0.5 bar, 1 bar, as high as 1 bar, 2 bar, 5 bar, 10 bar, 15 bar, 20 bar, 25 bar, 30 bar, 35 bar, or within any range defined between any pair of the foregoing values, such as 0.5 bar to 35 bar, 0.5 bar to 10 bar, or 1 bar to 5 bar. In some exemplary embodiments of the reaction performed as a liquid phase reaction, the solvent is typically a gas at the reaction temperature, but is maintained in the liquid phase by performing the reaction at an elevated pressure.

When performed as a liquid phase reaction, the reaction is typically performed at a temperature and pressure below the critical point of the solvent, where the pressure may be as low as 1 bar, as high as 2 bar, 5 bar, 10 bar, 15 bar, 20 bar, 25 bar, 30 bar, 35 bar, or within any range defined between any pair of the foregoing values, such as 1 bar to 35 bar, 1 bar to 10 bar, or 1 bar to 5 bar.

The efficiency of the reaction may be expressed in terms of conversion of oxime, selectivity of the desired product, or yield. Conversion is a measure of the amount of oxime reactant that is consumed by the reaction. Higher conversions are more desirable. The conversion is calculated as:

$$\text{Conversion}(\%) = 100\% \times \left(1 - \frac{\text{moles of oxime remaining}}{\text{moles of oxime supplied}}\right)$$

Selectivity is a measure of the amount of the desired product that is produced relative to all reaction products. Higher selectivity is more desirable. Lower selectivity indicates a higher percentage of reactant being used to form products other than the desired lactam. The selectivity is calculated as:

$$\text{Selectivity}(\%) = 100\% \times \frac{\text{moles of desired lactam produced}}{\text{moles of oxime supplied} - \text{moles of oxime remaining}}$$

Yield is a measurement that combines selectivity and conversion. Yield indicates how much of the incoming oxime is reacted to form the desired lactam. The yield is calculated as:

Yield (%)=Selectivity (%)×Conversion (%)/100%

The methods according to the present disclosure result in high conversion and selectivity of the desired lactam.

In typical embodiments, the conversion is 50% or higher. In a more particular embodiment, the conversion is from about 50% to about 100%. For example, the conversion may be as low as about 50%, 60%, 70%, 75%, or as high as about 80%, 85%, 90%, 95%, 97.5%, 99%, 99.5%, approaching 100%, or 100%, or may be within any range defined between any pair of the foregoing values, such as 50% to 100%, 75% to 99.5%, or 80% to 99%.

In typical embodiments, the selectivity is 50% or higher. In a more particular embodiment, the selectivity is as low as about 50%, 55%, 60%, 65%, or as high as about 70%, 75%, 80%, 85%, 90%, 95%, 97.5%, 99%, 99.5%, approaching 100%, or may be within any range defined between any pair of the foregoing values, such as 50% to 100%, 75% to 99.5%, or 80% to 99%.

In typical embodiments, the yield is 30% or higher. In a more particular embodiment, the yield is as low as about 30%, 35%, 40%, 45%, 50%, 55%, 60%, 65%, or as high as about 70%, 75%, 80%, 85%, 90%, 95%, 97.5%, 99%, 99.5%, approaching 100%, or may be within any range defined between any pair of the foregoing values, such as 50% to 100%, 75% to 99.5%, or 80% to 99%.

Figure 2:
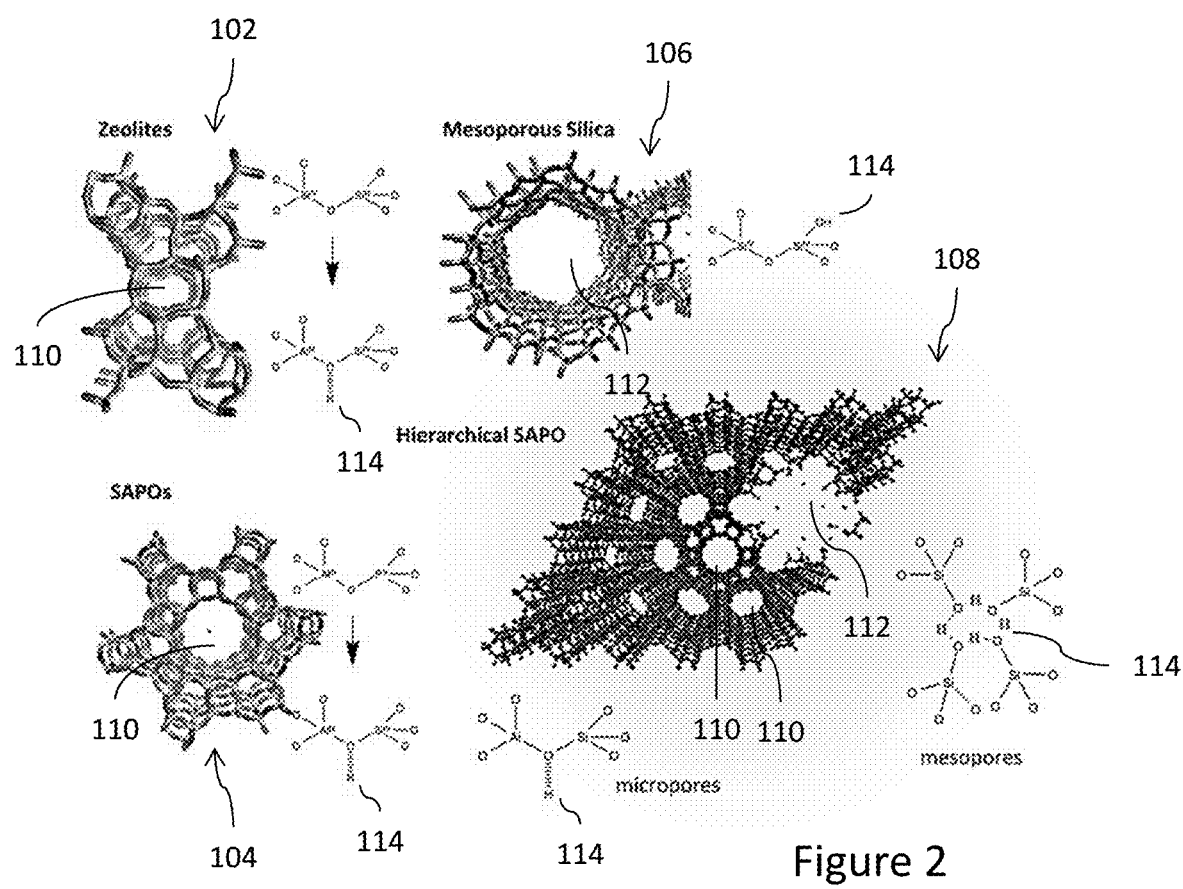
FIG. 2 illustrates active sites and pore diameters of an exemplary zeolite, an exemplary mesoporous silica, and exemplary SAPO material, and an exemplary hierarchical SAPO material.

The methods according to the present disclosure include an oxime reactant undergoing a Beckmann rearrangement reaction in the presence of a catalyst. Referring to FIG. 2, exemplary catalysts include natural and synthetic materials, including molecular sieves, microporous materials, such as zeolites 102, aluminophosphate (AlPO) materials (not shown), and silicoaluminophosphate (SAPO) materials 104, and mesoporous materials, such as mesoporous silica 106. As illustrated in FIG. 2, the microporous materials, such as zeolite 102 and SAPO 104, illustratively includes one or more micropores 110, and the mesoporous material, such as mesoporous silica 106, illustratively includes one or more mesopores 112. As shown in FIG. 2, the micropores 110 and mesopores 112 may include a plurality of active sites 114, such as a hydrogen atom or hydroxyl group.

Figure 3:
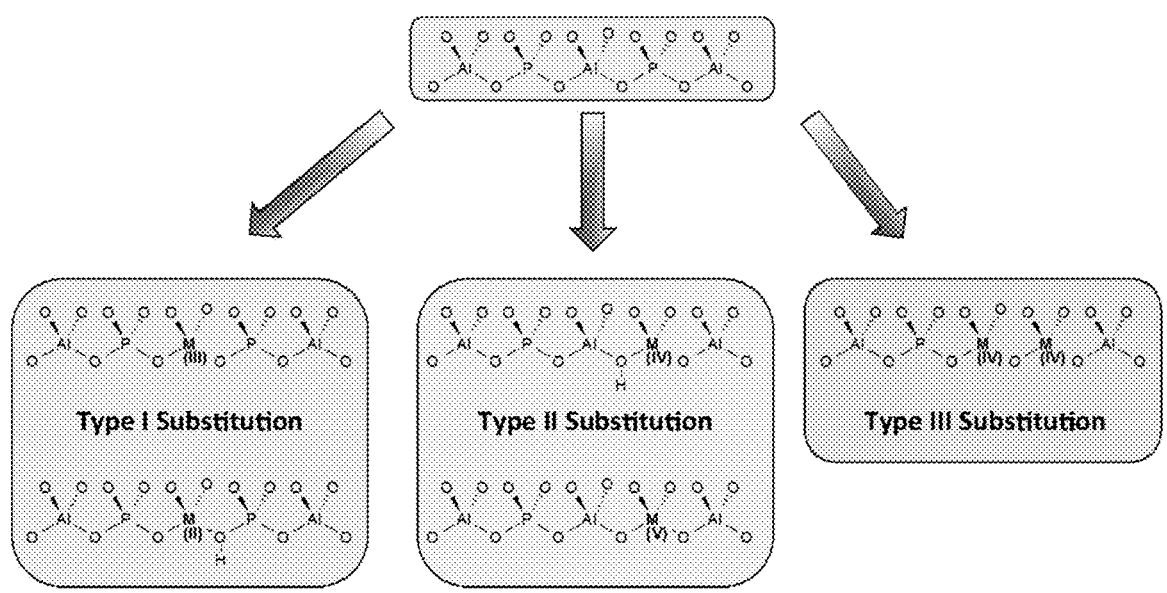
FIG. 3 illustrates Type I, Type II, and Type III isomorphous substitutions in an AlPO material.

Aluminophosphates (AlPO) catalysts are microporous materials known to be useful as catalysts. AlPO catalysts include repeating $AlO_4$ and $PO_4$ tetrahedra. It is possible to modify the catalytic properties of a given AlPO catalyst through, for example, the choice of topology, isomorphous substitution, deposition, grafting, and the like. As shown in FIG. 3, the aluminum and/or phosphorous atoms in the lattice may be isomorphously substituted. An isomorphous substitution of an aluminum atom with a (+2) or (+3) metal is illustrated as a Type I substitution, an isomorphous substitution of a phosphorous atom with a (+4) or (+5) metal is illustrated as a Type II substitution, and isomorphous substitutions of both an aluminum and a phosphorous atom with (+4) metal is illustrated as a Type III substitution. Exemplary metals that may be isomorphously substituted to form a Type I substitution include cobalt, copper, nickel, and zinc. Exemplary metals that may be isomorphously substituted to form a Type II substitution include titanium, vanadium, silicon, germanium, and tin.

One class of AlPO catalysts known to be useful as catalysts is the silicon-containing silicoaluminophosphate (SAPO) catalysts. Exemplary methods of preparing certain SAPO catalysts, are provided in U.S. Pat. No. 4,440,871 to Lok, et al., U.S. Pat. No. 8,772,476 to Levy, et al., N. Jappar, Y. Tanaka, S. Nakata, and T. Tatsumi, "Synthesis and Characterization of a New Titanium Silicoaluminophosphate: TAPSO-37," *Microporous and Mesoporous Materials*, Vol. 23, Issues 3-4, August 1998, pp. 169-178, J. Paterson, et al., "Engineering Active Sites for Enhancing Synergy in Heterogeneous Catalytic Oxidations," *Chemical Communications*, 47, p. 517-519, 2011, and M. E. Potter, et al., "Role of Isolated Acid Sites and Influence of Pore Diameter in the Low-Temperature Dehydration of Ethanol," *ACS Catal.*, 4(11), pp. 4161-4169, the disclosures of each are hereby incorporated by reference.

The weight percentage of silicon in the formed catalyst can also be determined. An exemplary method for determining the weight percentage of silicon is by inductively coupled plasma. Typically, silicon comprises from about 1 wt. % to about 10 wt. % of the total weight of the catalyst. In still other embodiment, silicon comprises a weight percentage of the total weight of the catalyst up from as little as 1 wt. %, 1.5 wt. %, 2 wt. %, 2.5 wt. % to as much as 6 wt. %, 7 wt. %, 8 wt. %, 9 wt. %, 10 wt. %, or within any range defined between any pair of the foregoing values.

Figure 4A:
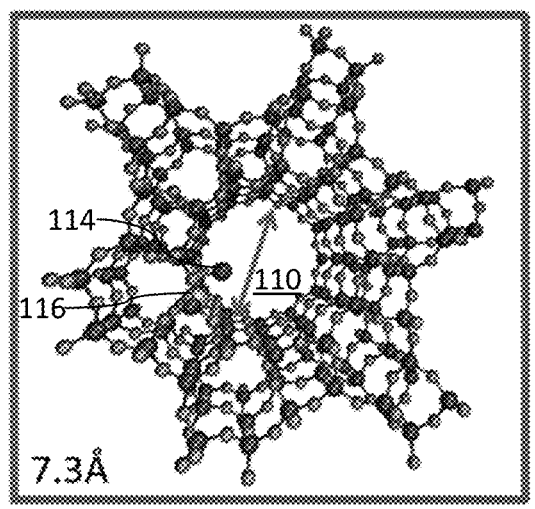
FIG. 4A illustrates a pore diameter of an exemplary microporous SAPO-5 material.

One exemplary microporous SAPO catalyst, SAPO-5, is illustrated in FIG. 4A. SAPO-5 is a silicon-containing aluminophosphate or silicoaluminophosphate catalyst with the International Zeolite Association (IZA) framework code AFI as described in the *Atlas of Zeolite Framework Types*, 6$^{th}$ ed., Baerlocher, et al., Elsevier, Amsterdam (2007), the disclosure of which is hereby incorporated by reference in its entirety. The SAPO-5 catalyst comprises a plurality of micropores 110 having a pore aperture of 7.3 Å. The catalyst comprises a plurality of silicon atoms 116 isomorphously substituted for phosphorous in the framework, leading to the formation of active sites 114.

Figure 4B:
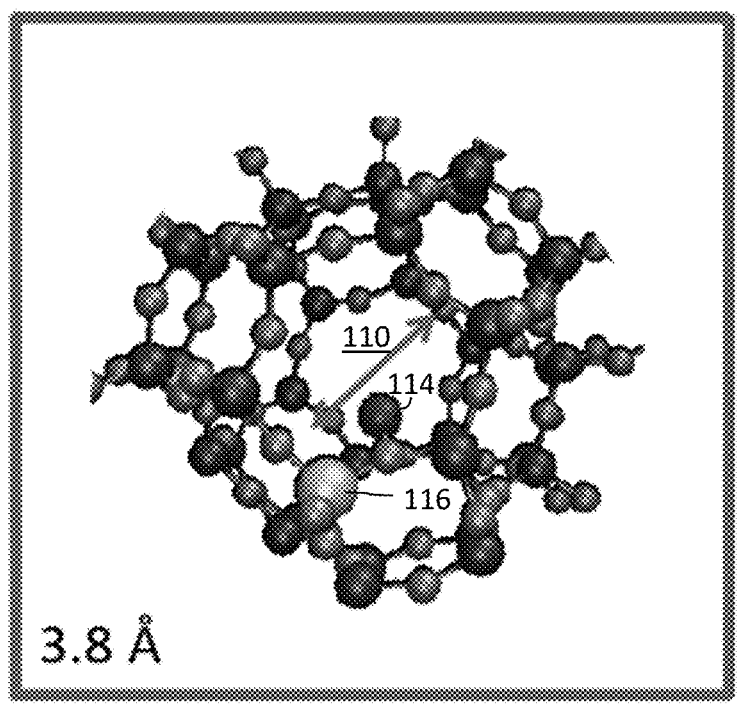
FIG. 4B illustrates a pore diameter of an exemplary microporous SAPO-34 material.

One exemplary microporous SAPO catalyst, SAPO-34, is illustrated in FIG. 4B. SAPO-34 is a silicon-containing aluminophosphate or silicoaluminophosphate catalyst with the International Zeolite Association (IZA) framework code CHA. The SAPO-34 catalyst comprises a plurality of micropores 110 having a pore aperture of 3.8 Å. The catalyst comprises a plurality of silicon atoms 116 isomorphously substituted for phosphorous in the framework leading to the formation of active sites 114.

One exemplary microporous SAPO catalyst, SAPO-37, is illustrated in FIG. 4C. SAPO-34 is a silicon-containing aluminophosphate or silicoaluminophosphate catalyst with the International Zeolite Association (IZA) framework code FAUFAU as described in the *Atlas of Zeolite Framework Types*, 6th ed., Christian Baerlocher, Lynne B. McCusker and David H. Olson, Elsevier, Amsterdam (2007), the disclosure of which is hereby incorporated by reference in its entirety. The SAPO-37 catalyst comprises sodalite cages linked together through 6,6 (double-6) secondary building units. Twelve of these sodalite cages are then used to create a super-cage structure of which the pore-aperture 110 is 7.4 Å and the internal diameter of the super-cage is in the region of 12-14 Å. The catalyst comprises a plurality of silicon atoms 116 isomorphously substituted for phosphorous in the framework, leading to the formation of active sites 114.

Other exemplary microporous catalysts include AlPO-11 (IZA framework code AEL), AlPO-18 (IZA framework code AEI), AlPO-31 (IZA framework code ATO), AlPO-37 (IZA framework code FAU), AlPO-41 (IZA framework code AFO), AlPO-44 (IZA framework code CHA), and corresponding monometallic and bimetallic structures, wherein the metal is selected from Mn, Fe, Cu, Mg, Cr, Co, Cu, Zn, Si, Ti, V, and Sn. In one more particular embodiment, the catalyst is a SAPO catalyst, such as SAPO-5, SAPO-11, SAPO-18, SAPO-31, SAPO-34, SAPO-37, SAPO-41, or SAPO-44.

In one embodiment, the AlPO catalyst or SAPO catalyst is a hierarchical porous (HP) catalyst. HP AlPO catalysts or HP SAPO catalysts include pores on more than one length scale, such as the illustrated hierarchical SAPO catalyst 108 illustrated in FIG. 2. In a more particular embodiment, the HP AlPO catalyst or HP SAPO catalyst includes bimodal pore distribution, such a first porous framework 110 comprising a plurality of micropores and a second porous framework 112 comprising a plurality of mesopores. In one exemplary embodiment, the hierarchical catalyst includes a plurality of micropores as little as 3 Å, 4 Å, 5 Å, 6 Å, as great as 7 Å, 8 Å, 9 Å, 10 Å, or within any range defined between any two of the foregoing values, such as 3 Å to 10 Å, 3 Å to 6 Å, 3 Å to 4 Å, 7 Å to 10 Å, or 7 Å to 8 Å. In one exemplary embodiment, the hierarchical catalyst includes a plurality of mesopores as little as 15 Å, 20 Å, 25 Å, 30 Å, as great as 35 Å, 40 Å, 45 Å, 50 Å, or within any range defined between any two of the foregoing values, such as 15 Å to 50 Å, 20 Å to 40 Å, or 15 Å to 40 Å.

The micropore framework 110 and mesopore framework 112 are interconnected. Both the microporous framework 110 and mesoporous framework 112 may include active sites 114, such as hydrogen atoms or hydroxyl groups. Without wishing to be held to any particular theory, it is believed that the micropores possess active sites for catalyzing the Beckmann rearrangement reaction, while the mesopores aid in diffusion of molecules into and out of the active sites.

Exemplary hierarchical AlPOs include HP Mn AlPO-5, reported by Zhou, et al., "Synthesis of hierarchical MeAPO-5 molecular sieves—Catalysts for the oxidation of hydrocarbons with efficient mass transport," *Microporous and Mesoporous Materials*, Vol 161, pp. 76-83, 2012, and HP SiAlPO-5, reported by Danilina, et al, "Influence of synthesis parameters on the catalytic activity of hierarchical SAPO-5 in space-demanding alkylation reactions," Catalysis Today, Vol. 168(1), pp. 80-85, 2011.

Figure 5:
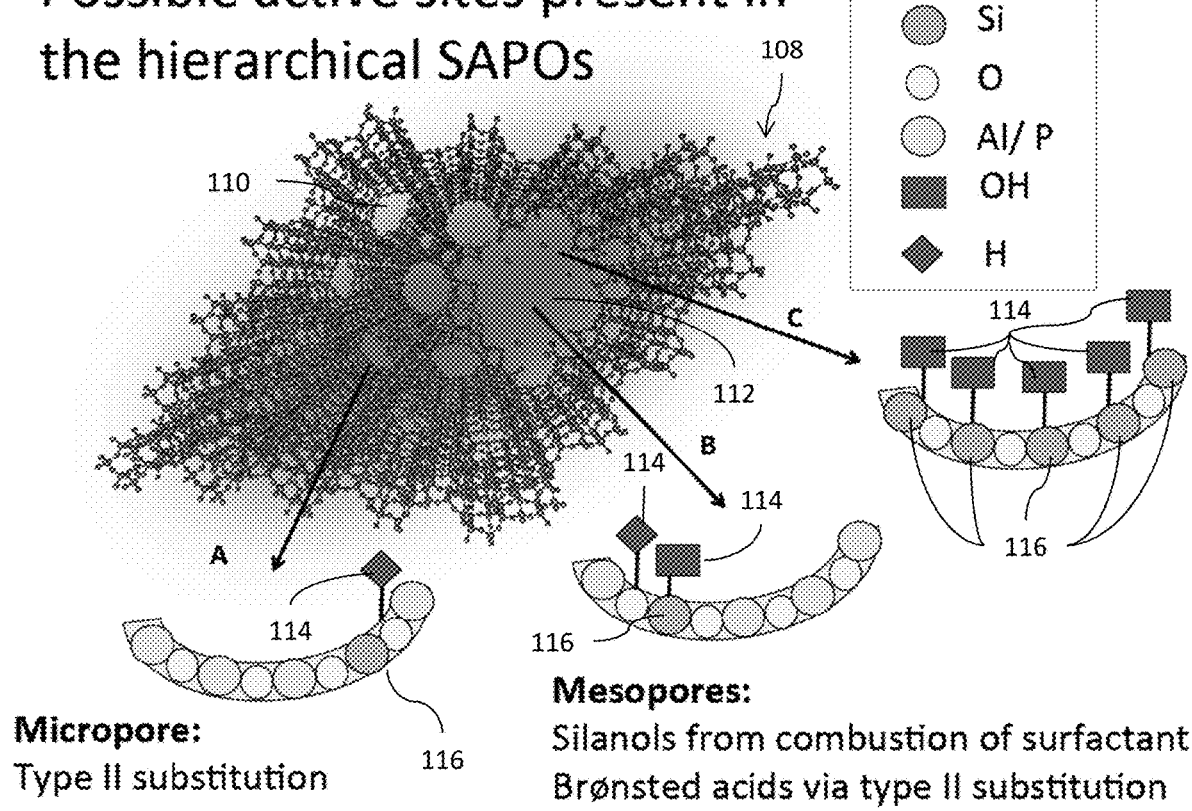
FIG. 5 illustrates possible micropore and mesopore active sites in an exemplary hierarchical SAPO material.

Referring next to FIG. 5, an exemplary hierarchical SAPO catalyst 108 is illustrated. As shown in FIG. 5, the exemplary hierarchical SAPO catalyst includes both a plurality of micropores 110 and one or more mesopores 112. The micropores illustrated in FIG. 5 are formed by the crystal lattice of the repeating $AlO_4$ and $PO_4$ tetrahedra, which may be isomorphously substituted with a silicon atom 116. As illustrated in FIG. 5, the SAPO catalyst may include Type II substitutions in the micropores, providing an available proton extending from the lattice into the micropore as a potential Brønsted acid active site 114. As further illustrated in FIG. 5, the SAPO may also include Type II substitutions in the much larger mesopores, providing both protons and/or hydroxyl groups extending from the lattice to serve as a potential Brønsted acid active site 114. Without wishing to be held to any particular theory, it is believed that the presence of silanols may provide desirable properties in the catalyst, such as additional hydrophilicity, additional acid sites, the potential to functionalize other active sites, a change in surface area, improved acid site density, and improved acid site strength.

As shown in FIG. 5, the micropore framework 110 and mesopore framework 112 are interconnected. Without wishing to be held to any particular theory, it is believed that the micropores 110 possess active sites for catalyzing the Beckmann rearrangement reaction, while the mesopores 112 aid in diffusion of molecules into and out of the active sites. The micropores 110 have the same pore aperture as the microporous SAPO catalyst on which the hierarchical catalyst is based. In contrast, the mesopore 112 in the hierarchical SAPO catalyst 108 illustrated in FIG. 5 has a pore diameter larger than pore aperture of the surrounding micropores 110.

In one exemplary embodiment, the hierarchical catalyst includes a plurality of micropores having a total volume as little as 0.05 $cm^3/g$, 0.07 $cm^3/g$, 0.10 $cm^3/g$, 0.12 $cm^3/g$, as great as 0.14 $cm^3/g$, 0.19 $cm^3/g$, 0.20 $cm^3/g$, or within any range defined between any two of the foregoing values, such as 0.05 $cm^3/g$ to 0.20 $cm^3/g$ or 0.10 $cm^3/g$ to 0.14 $cm^3/g$, and a plurality of mesopores having a total volume as little as 0.08 $cm^3/g$, 0.10 $cm^3/g$, 0.11 $cm^3/g$, as great as 0.12 $cm^3/g$, 0.15 $cm^3/g$, 0.17 $cm^3/g$, 0.20 $cm^3/g$, or within any range defined between any two of the foregoing values, such as 0.08 $cm^3/g$ to 20 $cm^3/g$ or 0.10 $cm^3/g$ to 0.15 $cm^3/g$. In one exemplary embodiment, the hierarchical catalyst has more surface area and/or pore volume than the corresponding microporous material In one exemplary embodiment, the hierarchical catalyst is an AlPO selected from HP AlPO-5, HP AlPO-11, HP AlPO-18, HP AlPO-31, HP AlPO-34, HP AlPO-37, HP AlPO-41, HP AlPO-44, and monometallic and bimetallic structures thereof, wherein the metal is selected from Mn, Fe, Cu, Mg, Cr, Co, Cu, Zn, Si, Ti, V, and Sn. In one exemplary embodiment, the metal is cobalt. In a more particular embodiment, the hierarchical catalyst is a hierarchical porous (HP) cobalt AlPO catalyst, such as HP Co AlPO-5. In one exemplary embodiment, the metal is titanium. In a more particular embodiment, the hierarchical catalyst is a hierarchical porous titanium AlPO catalyst, such as HP Ti AlPO-5. In one exemplary embodiment, the hierarchical catalyst is bimetallic, wherein the metals are cobalt and titanium. In a more particular embodiment, the hierarchical catalyst is a hierarchical porous bimetallic cobalt and titanium AlPO catalyst selected from the group consisting of HP Co Ti AlPO-5, HP Co Ti AlPO-11, HP Co Ti AlPO-18, HP Co Ti AlPO-31, HP Co Ti AlPO-34, HP Co Ti AlPO-37, HP Co Ti AlPO-41, HP Co Ti AlPO-44. In a more particular embodiment, the hierarchical catalyst is a hierarchical porous bimetallic cobalt and titanium AlPO catalyst, such as HP Co Ti AlPO-5.

In one exemplary embodiment, the hierarchical catalyst is a hierarchical porous (HP) SAPO catalyst, such as HP SAPO-5, HP SAPO-11, HP SAPO-18, HP SAPO-31, HP SAPO-34, HP SAPO-37, HP SAPO-41, and HP SAPO-44.

In one exemplary embodiment, the hierarchical SAPO catalyst is selected from a hierarchical SAPO-5 catalyst, a hierarchical SAPO-34 catalyst, and a hierarchical SAPO-37 catalyst. In one exemplary embodiment, the hierarchical SAPO catalyst is selected from a hierarchical SAPO-5 catalyst and a hierarchical SAPO-34 catalyst. In one exemplary embodiment, the hierarchical SAPO catalyst is a hierarchical SAPO-5 catalyst. In one exemplary embodiment, the hierarchical SAPO catalyst is a hierarchical SAPO-34 catalyst. In one exemplary embodiment, the hierarchical SAPO catalyst is a hierarchical SAPO-37 catalyst.

Figure 6:
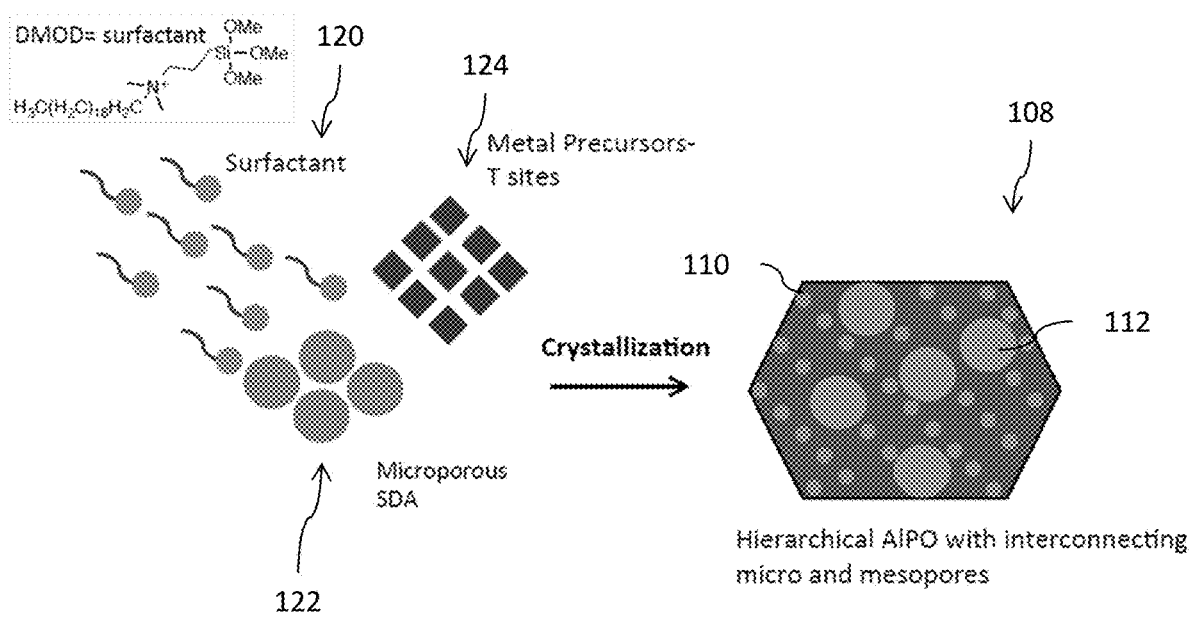
FIG. 6 illustrates an exemplary soft-templating technique for forming a hierarchical AlPO material.

In one embodiment, hierarchical catalysts, such as hierarchical AlPO and SAPO catalysts, may be formed using a soft-templating technique, as illustrated in FIG. 6. As illustrated in FIG. 6, an organosilane surfactant 120, such as dimethyloctadecyl[(3-(trimethoxysilyl)propyl] ammonium chloride (DMOD), was used in combination with a structure directing agent (SDA) 122 and metal precursors 124. Exemplary structure directing agents 122 include triethylamine and triethylammonium hydroxide. Exemplary metal precursors include aluminum isopropoxide. DMOD is an illustrative surfactant 120 containing an 18 carbon chain and a silicon-containing head. Without wishing to be held to any particular theory, it is believed that the silica portion of the surfactant is incorporated into the SAPO framework, and upon calcination of the organic hydrophobic tail additional silanol sites may be formed. These additional sites may also provide active sites for the Beckmann rearrangement.

Referring to FIG. 6, in an exemplary embodiment, a silicon source, such as silica, is added dropwise, to a mixture of surfactant 120, SDA 122, and metal precursor 124 and stirred. The resulting material is crystallized to form the hierarchical porous SAPO material 108, including both a plurality of micropores 110 from the SAPO crystalline structure, and a plurality of mesopores 112 from the surfactant.

In one exemplary embodiment, the surfactant includes a carbon chain of as little as 5 carbons, 8 carbons, 10 carbons, 15 carbons, as great as 18 carbons, 20 carbons, 25 carbons, 30 carbons, or greater, or within any range defined between any two of the foregoing values, such as 5 to 30 carbons, 8 to 25 carbons, or 15-20 carbons. In one exemplary embodiment, the surfactant includes a silicon-containing head group. In another exemplary embodiment, the surfactant includes a polar head group containing at least one of carbon, nitrogen, silicon, and phosphorous.

In one embodiment, the hierarchical catalyst is formed from a ratio of aluminum:phosphorous:SDA:water:silica: surfactant of about 1 Al:1 P:1 SDA:65 $H_2O$:0.15 Si:0.05 surfactant. In one embodiment, the hierarchical catalyst is formed from a ratio of aluminum:phosphorous:SDA:water: silica:surfactant of about 1 Al:1 P:0.8 SDA:50 $H_2O$:0.15 Si:0.05 surfactant. Exemplary SDAs include triethylamine and triethylamine hydroxide. Exemplary surfactants include DMOD.

In one embodiment, the hierarchical catalyst is crystallized at a temperature of about 200° C. for about 24 hours.

In one embodiment, the hierarchical catalyst is phase pure. In some embodiments, the hierarchical catalyst is a SAPO material that contains amorphous silicon in an amount as little as 1 wt. %, 0.5 wt. %, 0.1 wt. %, 0.05 wt. %, 0.01 wt. %, 0 wt. %, or within any range defined between any two of the foregoing values.

In one embodiment, hierarchical catalysts, such as hierarchical AlPO and SAPO catalysts, may be formed by post synthetic demetallation of a microporous framework. Exemplary reactants for demetallation of a zeolite microporous framework include basic reagents, such as sodium hydroxide, and acidic reagents, such as hydrochloric acid. In one exemplary embodiment, a microporous catalyst is added to a base, such as sodium hydroxide, tetrapropylammonium hydroxide with tetrapropylammonium bromide, or to an acid, such as hydrochloric acid. In one embodiment, the microporous catalyst is added to the base or acid in the presence of a surfactant. In one embodiment, the microporous catalyst is added to the base or acid without a surfactant. The material is partially digested, such as at a temperature between 298K and 373K for about 30 minutes. Following treatment, the partially digested material is calcined under air, such as at a temperature of about 550° C. for 16 hours, to form the mesoporous material.

In one embodiment, adsorption testing of the hierarchical porous material produces a Type IV isotherm with hysteresis, indicative of polymolecular adsorption of a porous adsorbent.

In one embodiment, the hierarchical porous materials have unit cells consistent with the unit cell of the corresponding microporous materials.

In one embodiment, the hierarchical porous materials have weak, isolated Brønsted acid sites. In one embodiment, the hierarchical porous materials do not have Lewis acidity.

In one embodiment, the hierarchical porous materials have isolated, tetrahedral silicon sites. In some embodiments, these sites may be similar to isolated, tetrahedral silicon sites of the corresponding microporous material. In some embodiments, the hierarchical porous materials include silanol active sites.

Example 1: Synthesis of a Microporous SAPO-5 (SAPO-5), a Hierarchically Porous SAPO-5 (HP SAPO-5)

The synthetic protocol for the isomorphous substitution of Si into the hierarchically porous AFI framework is described below. An equivalent method was deployed for the synthesis of the microporous analogue without the inclusion of the surfactant dimethyloctadecyl[(3-(trimethoxysilyl)propyl] ammonium chloride (DMOD).

Aluminum isopropoxide (6.807 g, Aldrich) was added to a Teflon beaker with phosphoric acid (2.28 ml, 85% in $H_2O$, Aldrich) and water (10 ml) and vigorously stirred for 1.5 hours until a homogeneous solution was formed. DMOD (1.2 ml, 72% in $H_2O$, Aldrich) was added drop wise, followed immediately by addition of triethylamine (3.7 ml, Aldrich) drop wise and then water (20 ml). The resulting thicker solution was stirred for one hour. Silica sol (0.771 ml, 40% in water, Aldrich) was added drop wise and the gel was stirred for a further 1.5 hours to obtain a white gel with the composition: 1 Al:1 P:0.8 TEA:50 $H_2O$:0.15 Si:0.05 DMOD.

The gel was divided between three 23 ml Teflon-lined stainless-steel autoclaves which were transferred to a pre heated fan assisted oven (WF-30 Lenton) at 200° C. for 24 hours.

The white solid product from each autoclave was collected via filtration and washed with 500 ml of deionized water. The product was left to dry at 80° C. overnight. The as-synthesized catalyst was calcined in a tube furnace under a flow of air at 550° C. for 16 hours to produce a white solid.

Example 2: Synthesis of a Microporous SAPO-34 (SAPO-34) and a Hierarchically Porous SAPO-34 (HP SAPO-34)

The synthetic protocol for the isomorphous substitution of Si into the hierarchically porous CHA framework is described below. An equivalent method was deployed for the synthesis of the microporous analogue without the inclusion of the surfactant dimethyloctadecyl[(3-(trimethoxysilyl)propyl]ammonium chloride (DMOD).

Aluminium isopropoxide (4.5450 g, Aldrich) was added to a Teflon beaker with tetraethylammonium hydroxide (TeaOH) (9.14 ml, 35% in H$_2$O, Aldrich) and stirred for one hour. Fumed silica (0.2 g) was added slowly and stirred for ten minutes. DMOD (0.8 ml, 72% in water, Aldrich) was added drop wise and the white opaque gel stirred for one hour. Deionized water (14 ml) was added drop wise followed directly by phosphoric acid (1.5 ml, 85% in H$_2$O, Aldrich). The gel was stirred vigorously for two hours to produce a white gel with the composition: 1 Al:1 P:1 TeaOH:65 H$_2$O:0.15 Si:0.05 DMOD.

The contents of the gel were divided between two 23 ml Teflon-lined stainless-steel autoclaves which were transferred to a pre heated fan assisted oven (WF-30 Lenton) at 200° C. for 24 hours.

The white solid product from each autoclave was collected via filtration and washed with 500 ml of deionized water. The product was left to dry at 80° C. overnight. The as-synthesized catalyst was calcined in a tube furnace under a flow of air at 550° C. for 16 hours to produce a white solid.

Example 3: Synthesis of a Microporous SAPO-37 (SAPO-34) and a Hierarchically Porous SAPO-37 (HP SAPO-37)

The synthetic protocol for the isomorphous substitution of Si into the hierarchically porous FAU framework is described below. An equivalent method was deployed for the synthesis of the microporous analogue without the inclusion of the surfactant dimethyloctadecyl[(3-(trimethoxysilyl)propyl]ammonium chloride (DMOD).

Boehmite (5.5844 g) was added slowly to a solution of phosphoric acid (85 wt. %, 9.251 g) and deionized water (10 g) in a Teflon beaker. The thick white mixture was stirred magnetically for 7 hours and labelled solution A.

Solution B was prepared by adding DMOD (72 wt. %, 2 ml) drop wise to a solution of tetra propyl ammonium hydroxide, TPAOH (40 wt. %, 38.689 g) and tetra methyl ammonium hydroxide. TMAOH (0.365 g), followed by fumed silica (1 g). Solution B was stirred for 2 hours.

Once both solution A and B were homogenized solution B was added drop wise to solution A to create a very thick mixture. This was stirred for 68 hours. Then transferred to autoclaves and crystallized at 200° C. for 24 hours.

The resulting white solid was filtered with 1 liter of deionized water and left to dry in an oven (80° C.) overnight. The catalyst was then calcined at 550° C. for 16 hours under air to yield a white solid.

Example 4: Characterization of Catalysts

Powder X-Ray Diffraction

Figure 7A:
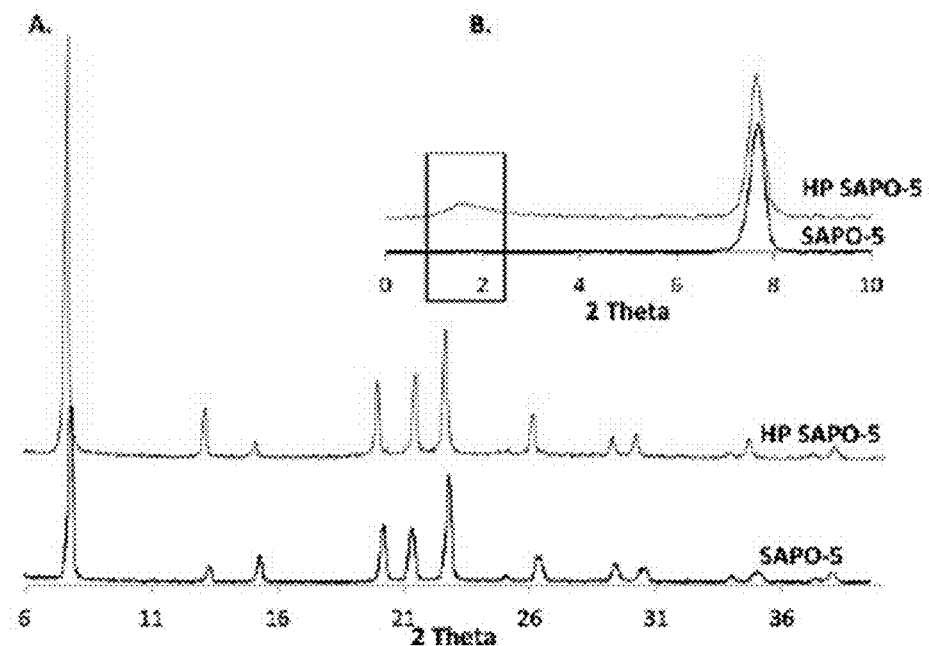
FIG. 7A is related to Example 4, and illustrates the X-ray diffraction spectra for SAPO-5 and HP SAPO-5.
Figure 7B:
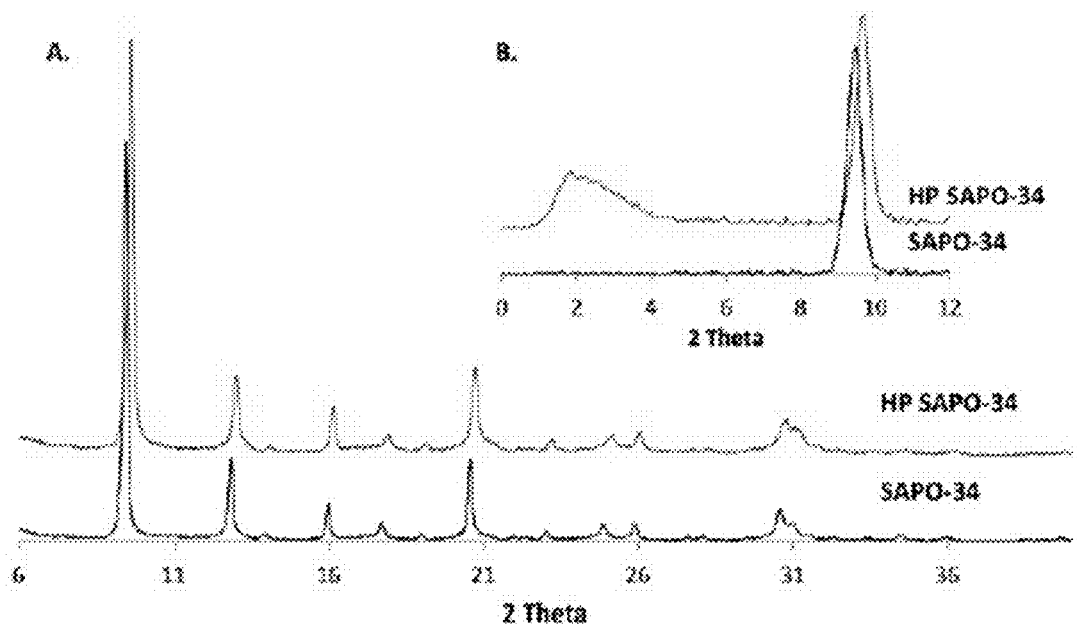
FIG. 7B is related to Example 4, and illustrates the X-ray diffraction spectra for SAPO-34 and HP SAPO-34.
Figure 7C:
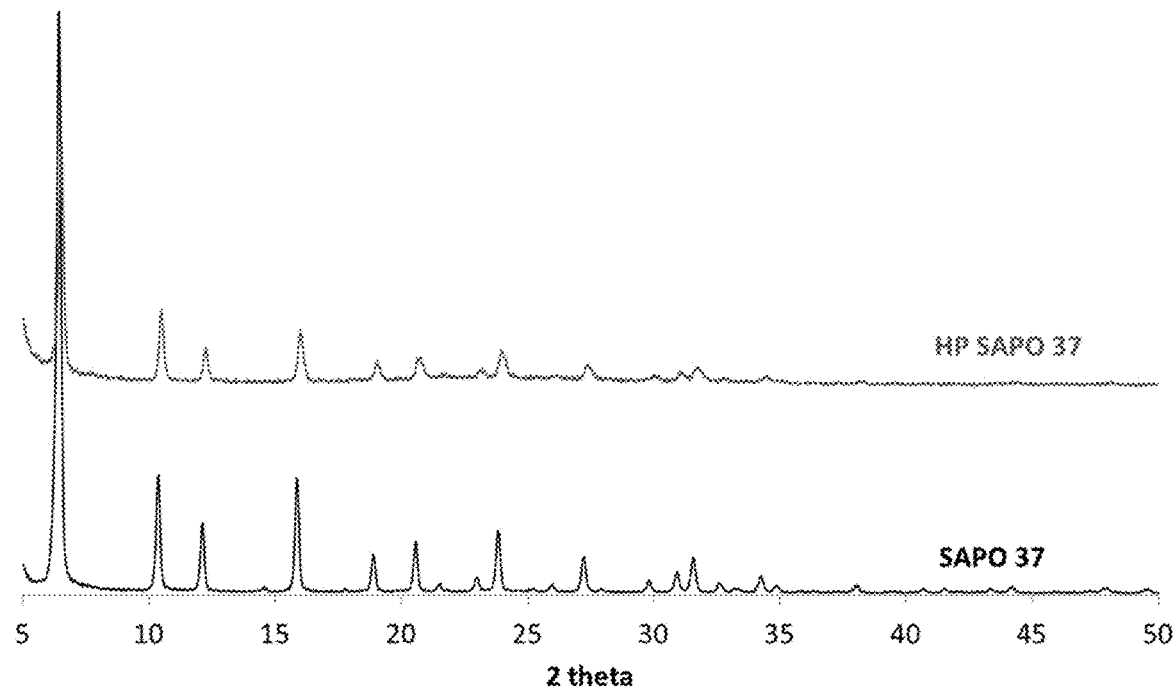
FIG. 7C is related to Example 4, and illustrates the X-ray diffraction spectra for SAPO-37 and HP SAPO-37.

Powder X-ray diffraction (pXRD) patterns were obtained using a Bruker D2 diffractometer using Cu K α1 radiation where λ=1.54056. Low angle X-ray diffraction patterns were obtained using a Bruker C2 GADDS diffractometer. The hierarchical catalysts were confirmed to retain their parent unit cells via pXRD (FIGS. 7A-7C). The corresponding lattice parents were similar to the microporous analogues (see, e.g. FIGS. 8A, 8B, 9A and 9B) and confirmed that the hierarchical catalysts were phase pure and retained their crystallinity.

As shown in FIG. 7A-7C, the phase purity and crystallinity of all materials were confirmed via powder X-ray diffraction. All signals can be attributed to the corresponding AFI, CHA, or FAU structure according to the IZA database. The CellRef refinement values for the calcined AFI and CHA catalysts are presented as FIGS. 8 and 9. The results were consistent with the expected AFI framework for SAPO-5 and HP SAPO-5, and the expected CHA framework for SAPO-34 and HP SAPO-34.

Low angle XRD measurements of the hierarchical samples, shown in the inserts of FIGS. 7A and 7B, revealed a peak at low angles, which was absent in the microporous samples. This peak indicates the presence of mesopores in the hierarchical samples.

BET Surface Area

Nitrogen adsorption desorption experiments were performed using a Gemini 2575 Brunauer-Emmett-Teller (BET) Apparatus with nitrogen as the adsorption gas at 77K.

BET measurements for each catalyst are presented in Table 1. As shown in Table 1, the hierarchical catalysts had higher overall surface area ($S_{BET}$), higher micropore volume ($V_{micro}$), and higher mesopores volume ($V_{meso}$) than the corresponding microporous materials.

TABLE 1

BET properties.

| Sample | $S_{BET}$ (m$^2$g$^{-1}$) | $V_{micro}$ (cm$^3$g$^{-1}$) | $V_{meso}$ (cm$^3$g$^{-1}$) |
|---|---|---|---|
| SAPO-5 | 137 | 0.06 | 0.04 |
| HP SAPO-5 | 237 | 0.07 | 0.11 |
| SAPO-34 | 407 | 0.14 | 0.09 |
| HP SAPO-34 | 566 | 0.19 | 0.17 |
| SAPO-37 | 623.6 | 0.26 | 0.11 |
| HP SAPO-37 | 482.2 | 0.11 | 0.27 |

Figure 10A:
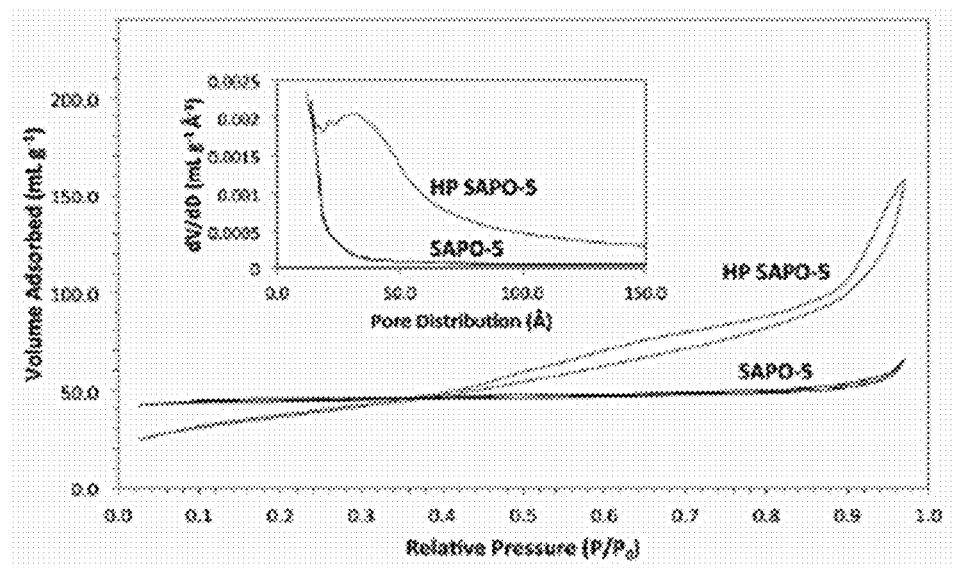
FIG. 10A is related to Example 4, and illustrates the BET adsorption and BJH adsorption pore volume curves for SAPO-5 and HP SAPO-5.
Figure 10B:
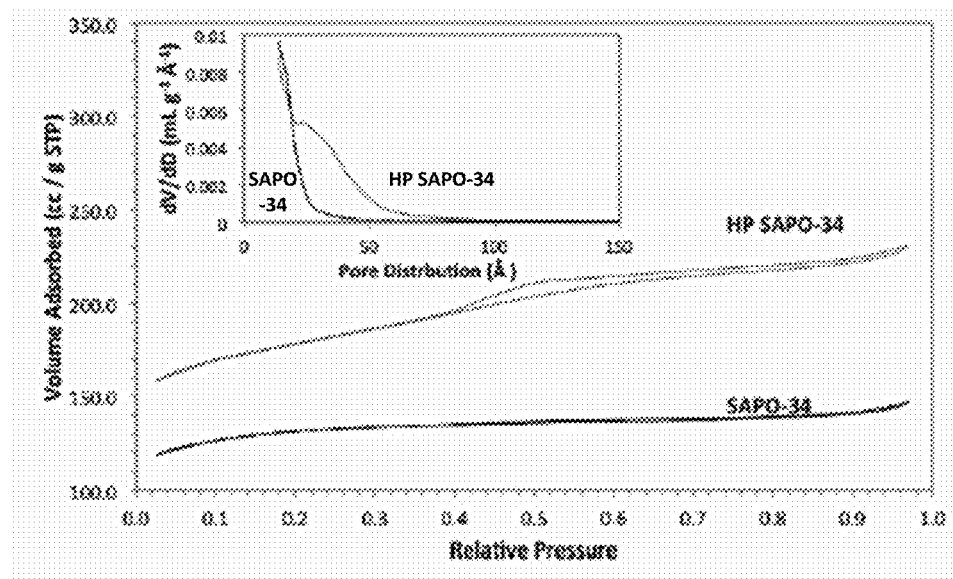
FIG. 10B is related to Example 4, and illustrates the BET adsorption and BJH adsorption pore volume curves for SAPO-34 and HP SAPO-34.
Figure 10C:
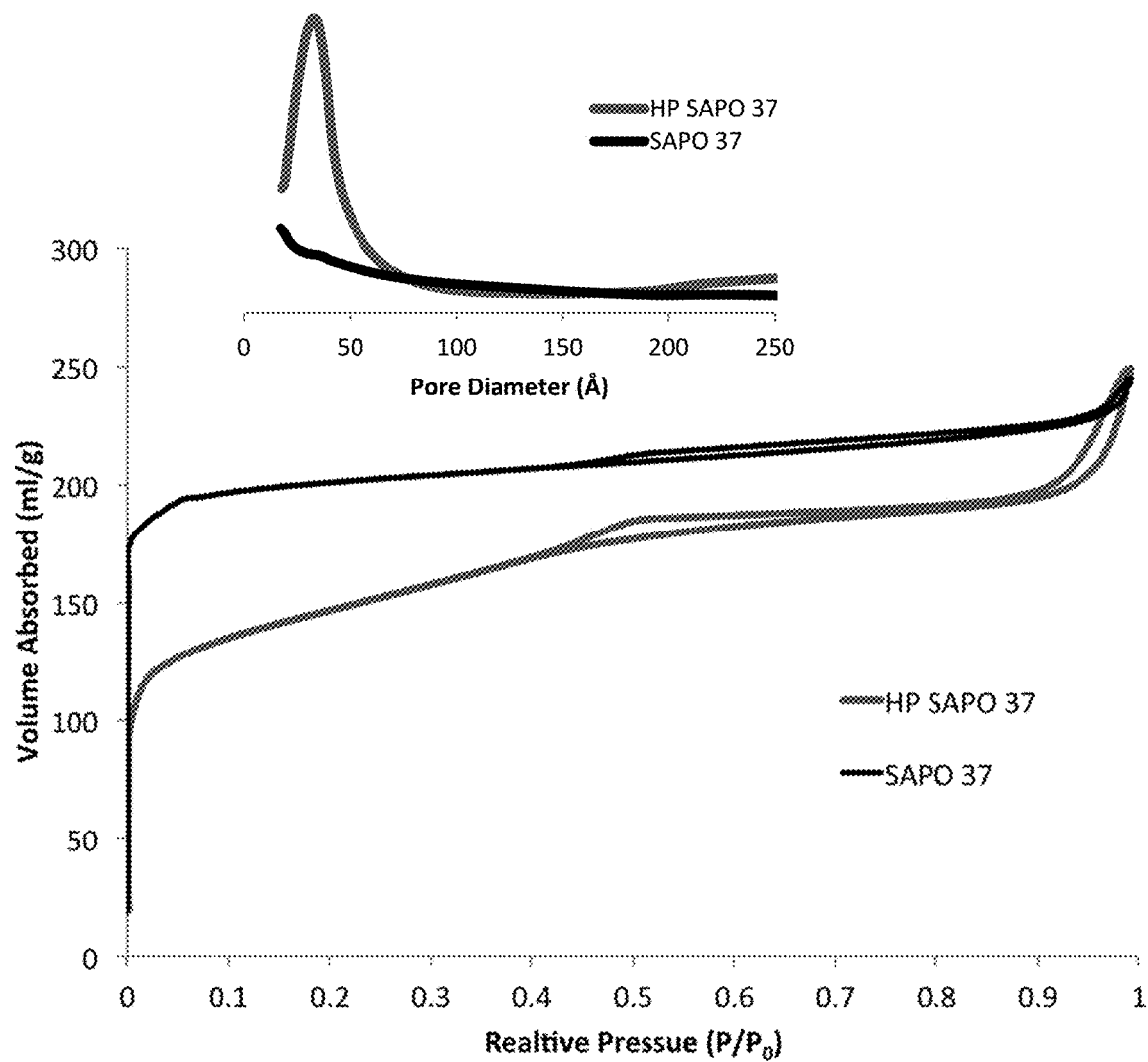
FIG. 10C is related to Example 4, and illustrates the BET adsorption and BJH adsorption pore volume curves for SAPO-37 and HP SAPO-37.
Figure 11A:
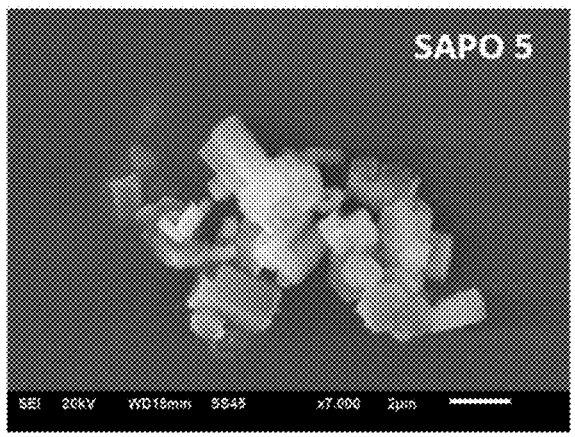
FIG. 11A is related to Example 4 and illustrates an SEM image of SAPO-5.
Figure 11B:
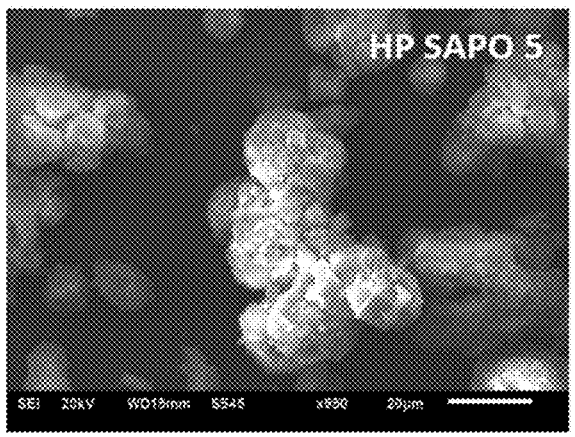
FIG. 11B is related to Example 4 and illustrates an SEM image of HP SAPO-5.
Figure 11C:
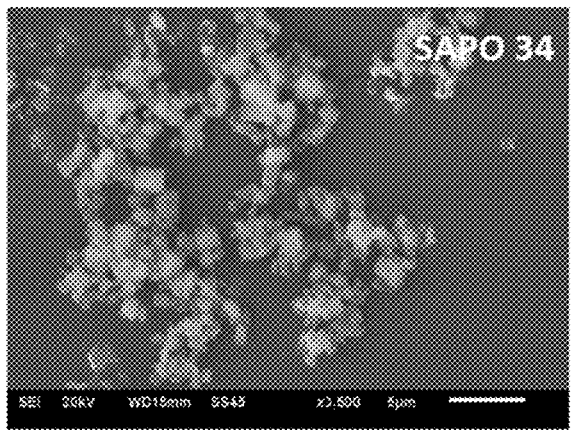
FIG. 11C is related to Example 4 and illustrates an SEM image of SAPO-34.
Figure 11D:
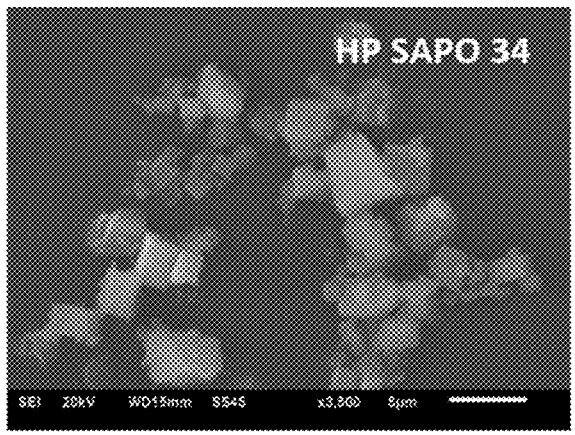
FIG. 11D is related to Example 4 and illustrates an SEM image of HP SAPO-34.

The N$_2$ adsorption desorption isotherms of HP SAPO-5, HP SAPO-34, and SAPO-37, shown in FIGS. 10A-10C, are typical of a type IV isotherm with a hysteresis. The exhibited type IV isotherms with hysteresis for the hierarchical porous materials are consistent with the presence of mesopores in the corresponding hierarchical frameworks.

The BJH adsorption pore volume curves provided as inserts in FIGS. 10A-10C further confirm the presence of mesopores having a diameter between about 20 Å and about 60 Å in the hierarchical systems, as well as the absence of such mesopores in the microporous materials.

The hierarchical catalysts exhibited type IV isotherms (FIGS. 10A-10C) with hysteresis, which is consistent with the presence of mesopores. The surface areas and mesopore volumes were also higher in the hierarchical catalysts compared to the microporous analogues, consistent with incorporation of mesopores into the hierarchical frameworks (Table 1). The BJH adsorption pore distribution curves further support the presence of mesopores in the hierarchical systems and the absence of such mesopores in the microporous catalysts (FIGS. 10A-10C).

Scanning Electron Microscopy and Transmission Electron Microscopy Images

The hierarchical materials porosity was further evaluated via scanning electron microscopy (SEM) (FIGS. 11-14). FIG. 11A illustrates the elongated hexagonal crystals of microporous SAPO-5. FIG. 11B illustrates the crystals of the hierarchical porous HP SAPO-5. FIG. 11C illustrates cubic crystals of microporous SAPO-34. FIG. 11D illustrates the crystals of the hierarchical porous HP SAPO-34. The hierarchical porous material images in FIGS. 11B and 11D depict larger particles than the corresponding microporous materials in FIGS. 11A and 110. The hierarchical materials appear to include aggregates of smaller crystals.

Figure 12A:
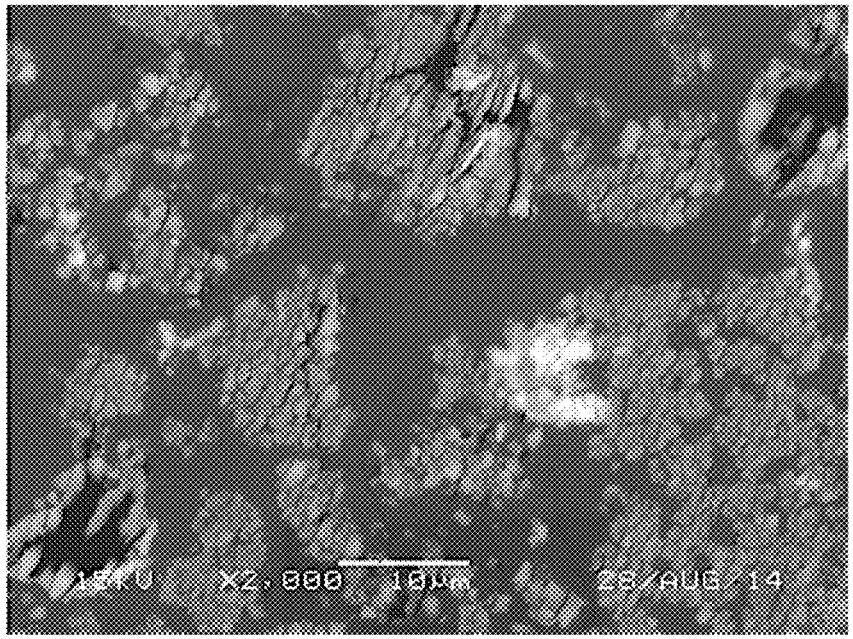
FIGS. 12A and 12B are related to Example 4 and illustrate SEM images of HP SAPO-34.
Figure 12B:
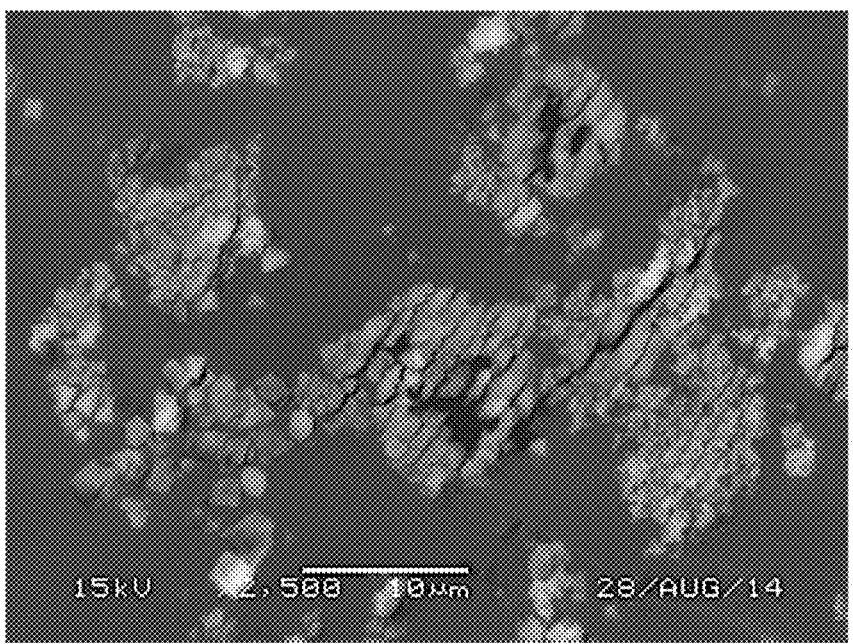
Figure 13:
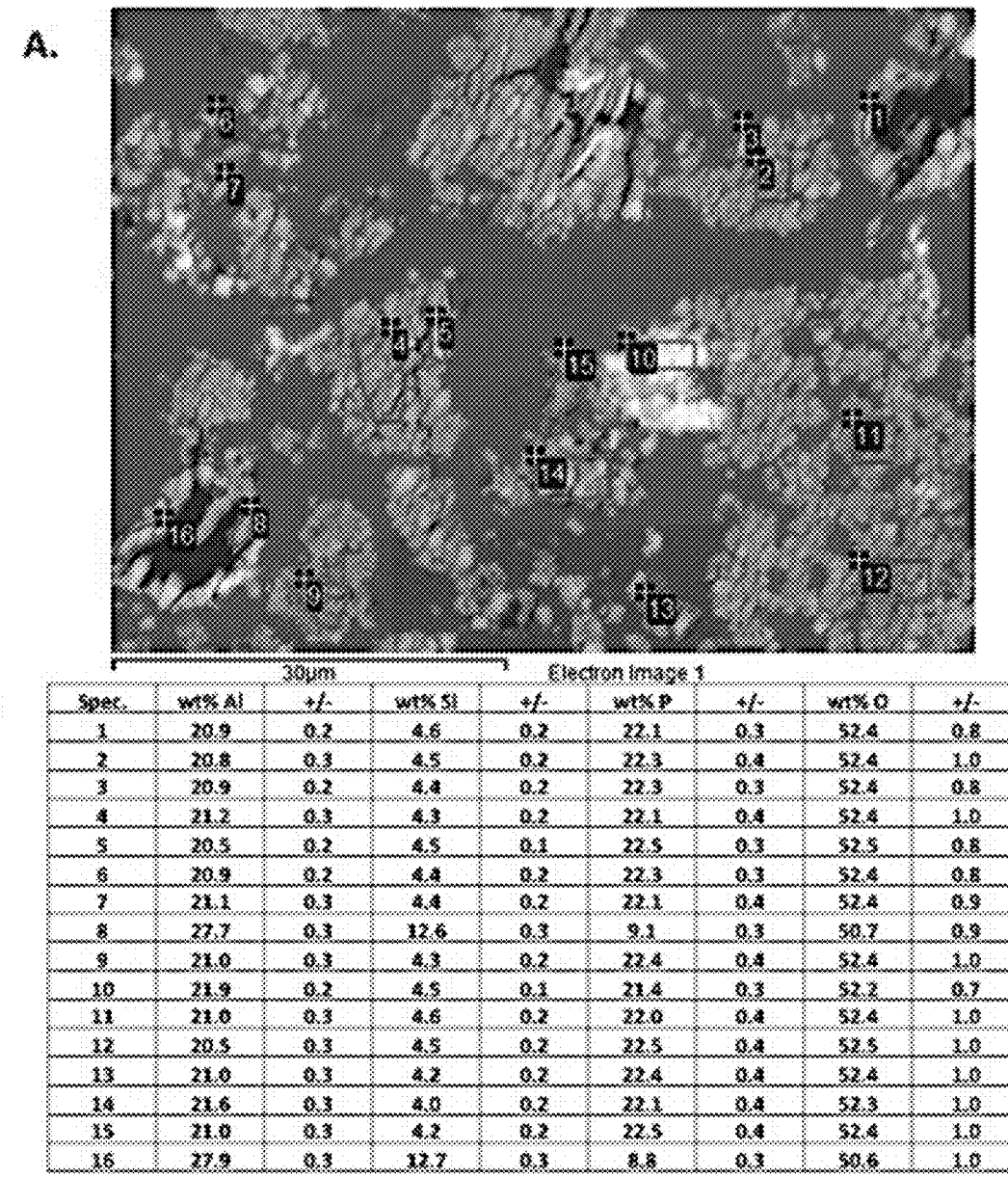
FIG. 13 is related to Example 4 and illustrates an SEM image and EDS data of HP SAPO-34.
Figure 14:
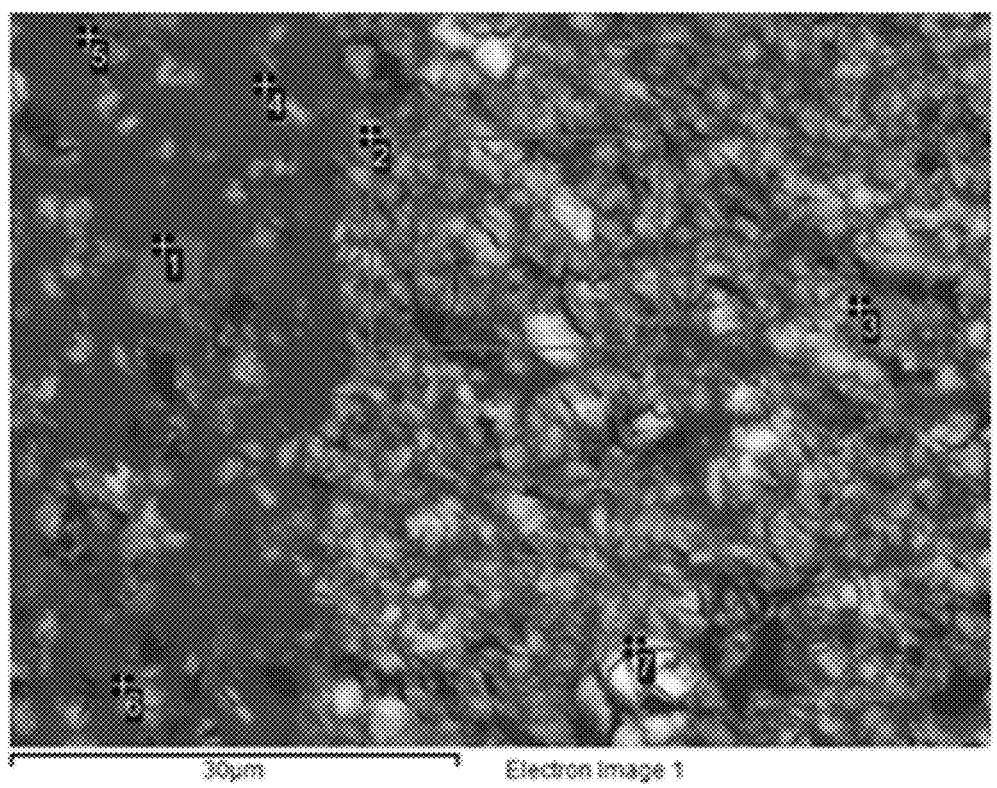
FIG. 14 is related to Example 4 and illustrates an SEM image and EDS data of HP SAPO-5.

As shown in FIGS. 12A and 12B, the HP SAPO-34 is composed of blocky, well-dispersed crystals, as well as larger agglomerations of possible intergrown and less-dispersed crystals.

The SEM images indicated the samples have a fairly uniform composition throughout the sample. As shown in the SEM image and corresponding energy dispersive (EDS) data of FIG. 13, the composition of the HP SAPO-34 is fairly uniform. As shown in the SEM image and corresponding energy dispersive (EDS) data of FIG. 14, the composition of the HP SAPO-5 is fairly uniform.

The hierarchical materials porosity was further evaluated via transmission electron microscopy (TEM) (FIGS. 15-19). The TEM images indicated the samples having a fairly uniform composition throughout the sample, and revealed fine mesoporosity in both the crystalline HP SAPOs (see FIGS. 17-19).

Figure 15:
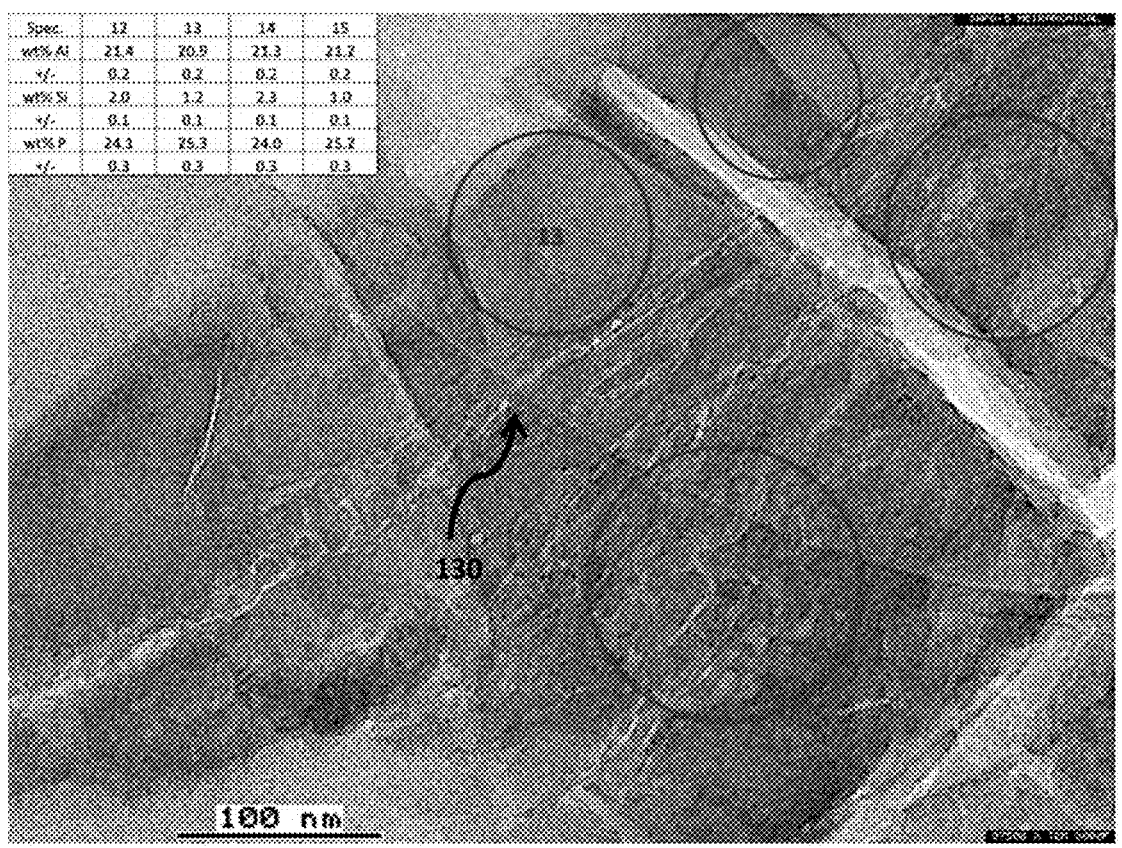
FIGS. 15 and 16 are related to Example 4 and illustrate a TEM image and elemental analysis of HP SAPO-5.

As shown in the TEM image an elemental analysis of FIG. 15, the HP SAPO-5 material had regions of mesoporosity in the faulted region 130. The elemental analysis of the ratio of Al:Si:P, was as expected for a SAPO material.

Figure 16:
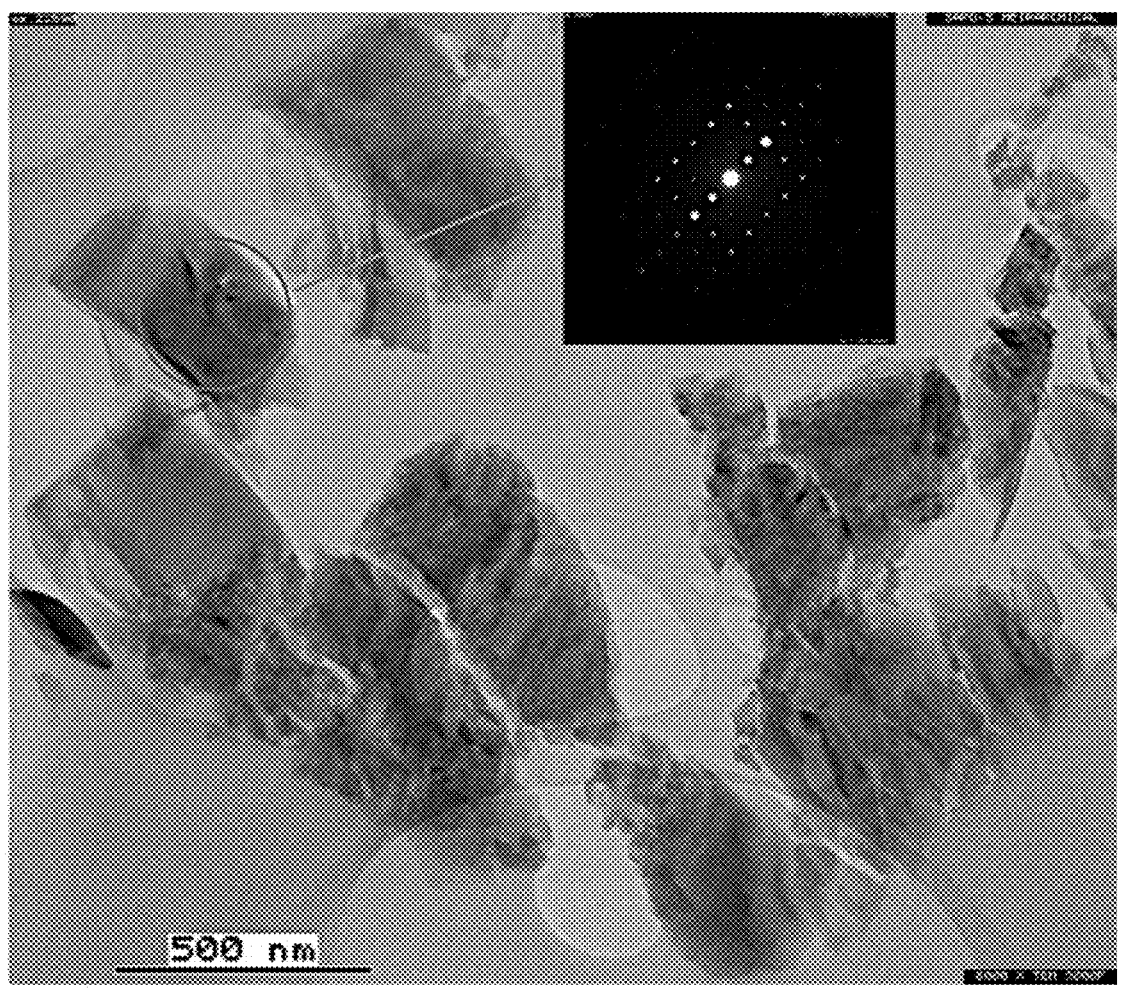

The lattice crystal structure of each of the HP SAPO-5 and HP SAPO-34 was confirmed. As shown in FIG. 16, the diffraction pattern of the selected portion of the HP SAPO-5 material was confirmed to be AFI. The elemental analysis in FIG. 15 is consistent with the expected Al:P:Si ratio for a SAPO material.

Figure 17:
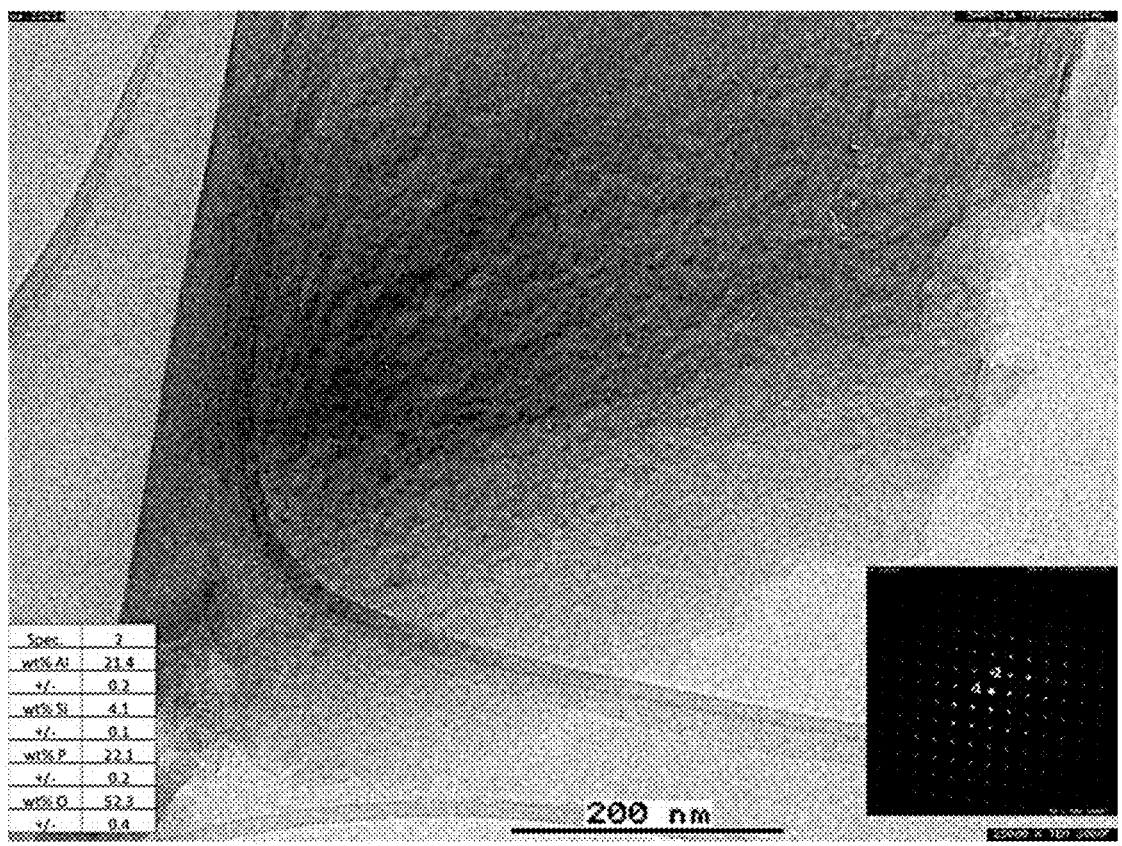
FIGS. 17-19 are related to Example 4 and illustrate a TEM image and elemental analysis of HP SAPO-34.
Figure 18:
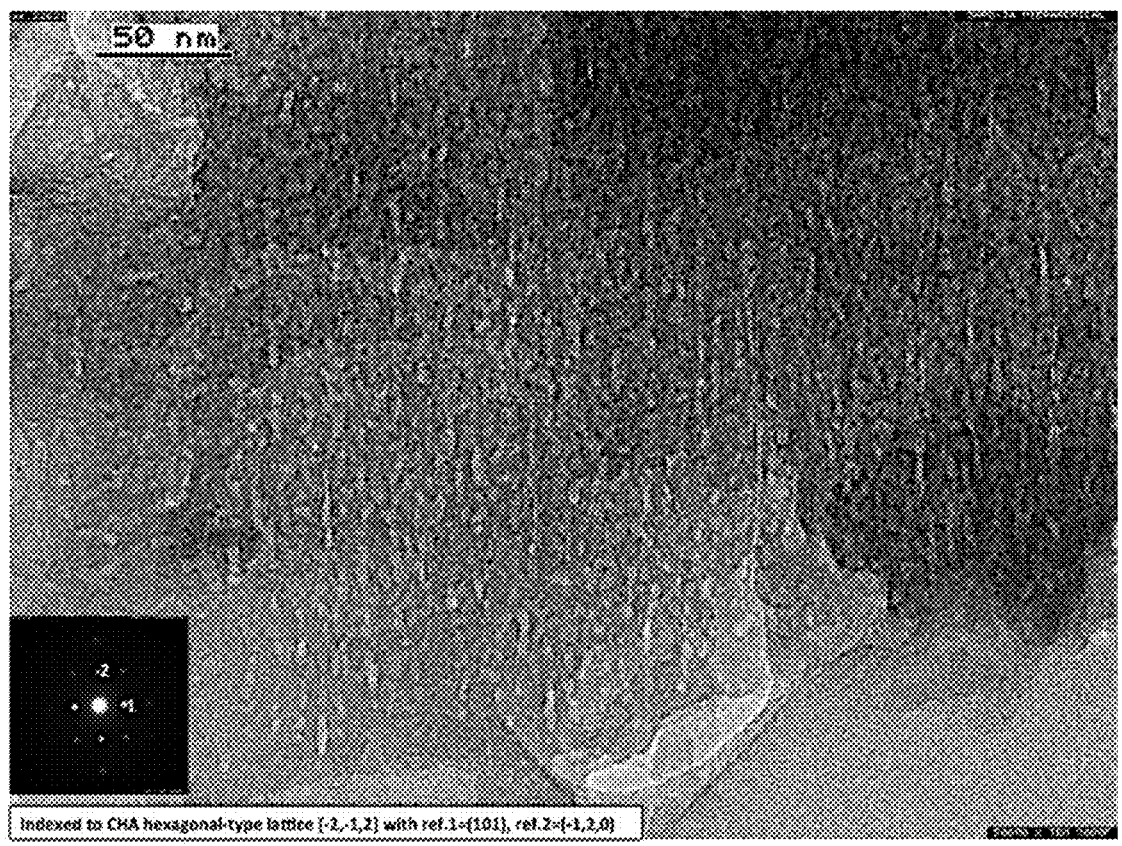

From the TEM and diffraction patterns of HP SAPO-34 it was possible to elucidate the rod like and elongated shapes of the mesopores and their positioning perpendicular and parallel to the rhombohedral basis vectors. It was clear that these mesopores were well connected within the microporous network. (FIGS. 17, 18). As shown in FIG. 17, the diffraction pattern of the selected portion of the HP SAPO-5 material was confirmed to be AFI. The elemental analysis in FIG. 17 is consistent with the expected Al:P:Si ratio for a SAPO material. The two reflections (101) (RHS ref1) and (−1, 1, 1) (RHS ref 2) are equivalent to (100) and (101), the pores therefore appear to have rod-like morphology, elongated parallel to one or another to the rhombohedral basis vectors. As shown in FIG. 18, which includes a TEM image and diffraction pattern of HP SAPO-34 from the same location, the indexing indicates that the pores are elongated perpendicular to the (101) plane. This is equivalent to the (100) of the rhombohedral type unit cell.

Figure 19:
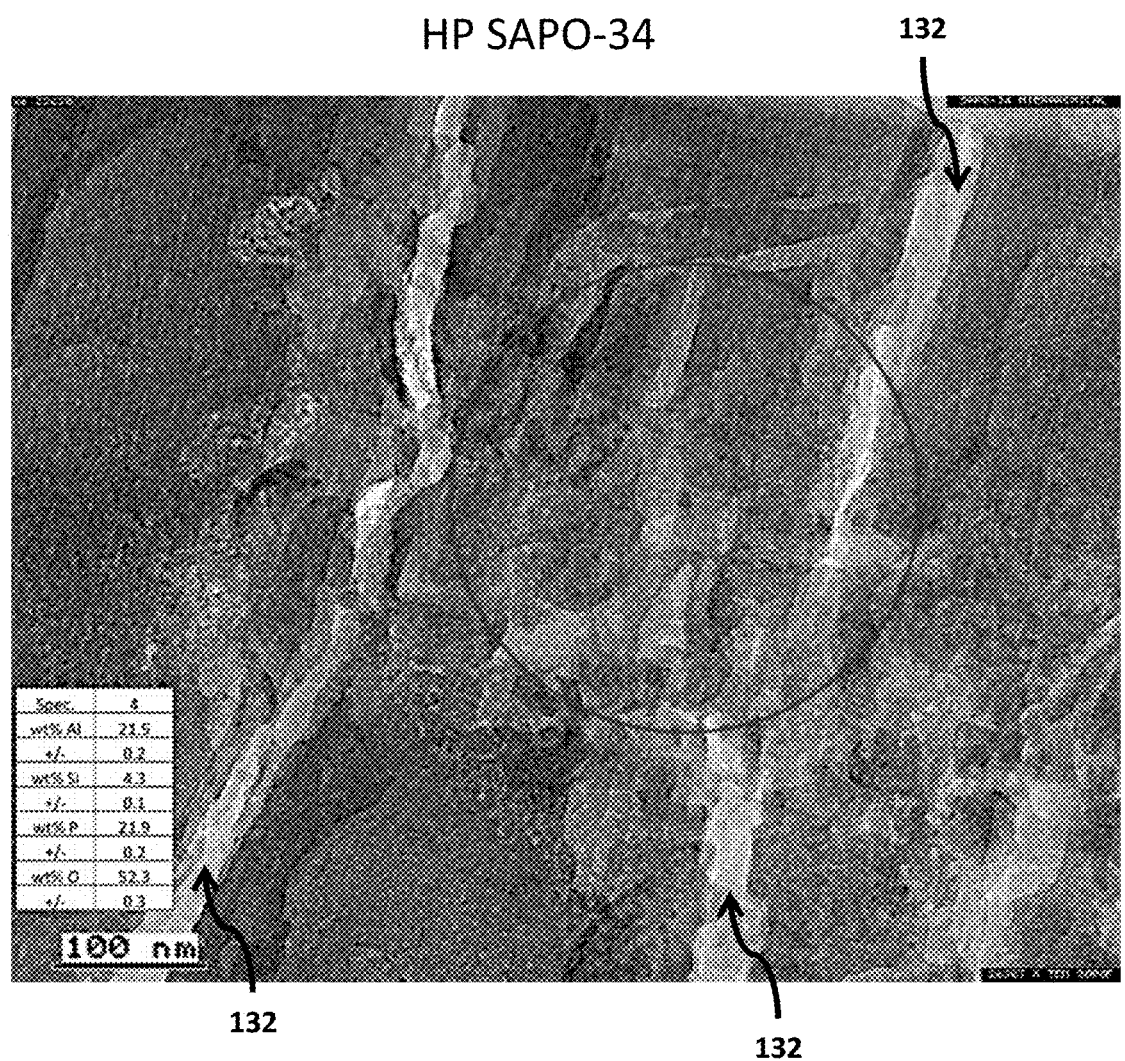

The TEM image and EDS of the HP SAPO-34 in FIG. 19 further show the presence of some secondary porosity 132.

Example 5: Vapor Beckmann Rearrangement of Cyclohexanone Oxime and Cyclooctanone Oxime The catalytic performance of the hierarchical HP SAPO-5 and HP SAPO-34 samples was compared to that of the microporous SAPO-5 and SAPO-34 samples. A vapor Beckmann rearrangement of cyclohexanone oxime (see FIG. 1A) was performed for each pair of hierarchical and microporous catalysts.

A cylindrical quartz fixed bed reactor (4 mm in diameter) with a quartz frit was packed with 0.5 cm layer of glass beads (1 mm), a 4 cm layer of pelletized catalyst (0.2 g), and a further 20 cm of glass beads (1 mm) were placed inside the heater unit of the reactor assembly. The sample was then pre-treated at 673K under a 50 ml/min flow of helium gas for one hour. The temperature was then lowered to 598K and the flow of helium was reduced to 33.3 ml/hour. A liquid feed of 100 g/litre of cyclohexanone oxime in ethanol was fed into the reactor to maintain a WHSV of 0.79 $hr^{-1}$ that was controlled by an electronic syringe pump. A sample was taken after every hour when steady state was achieved. Samples were analyzed using a Perkin Elmer Glarus 480 gas chromatogram with FID and using an Elite 5 column, the peak areas were calibrated using pre-determined response factors with mesitylene as an internal standard.

The feed solution for assessing the carbon balance using mesitylene as the internal standard was composed of: Mesitylene: 0.444 g; Cyclohexanone oxime: 4.10 g, EtOH: 36.000 g Performing an identical procedure to one described above the following GC data was obtained at 598K, WHSV of 0.79 $hr^{-1}$ with HP SAPO-5 and by using the response factors it was possible to calculate the number of moles from the peak areas.

Figure 20A:
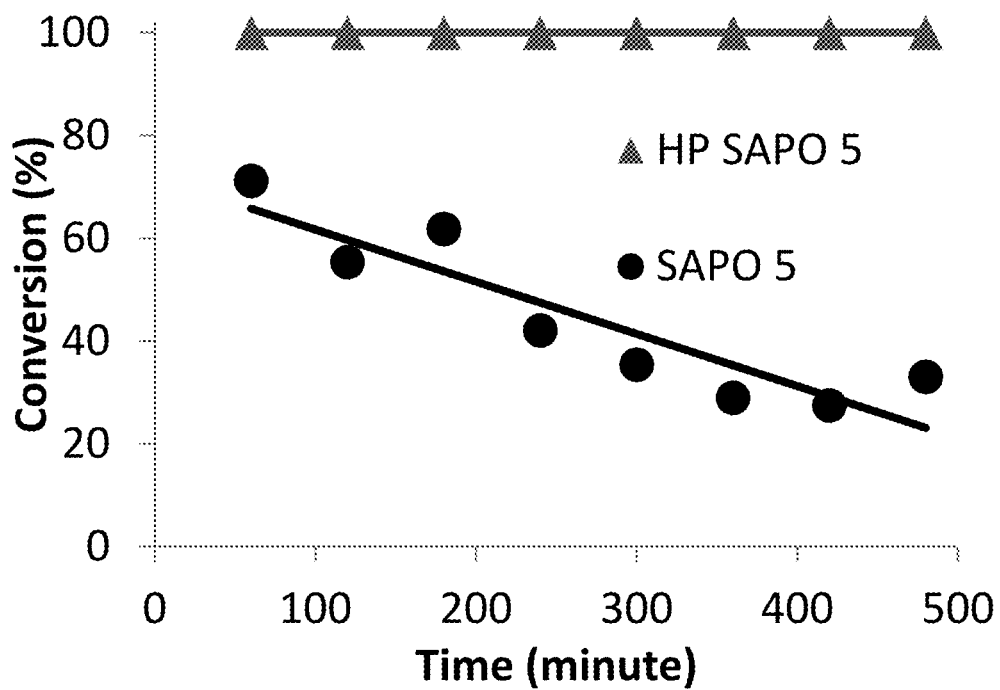
FIGS. 20A-20I are related to Example 5 and illustrate the conversion, selectivity, and yield of SAPO-5, HP SAPO-5, SAPO-34, HP SAPO-34, H-ZSM-5, and MCM-41 for the gas-phase Beckmann rearrangement of cyclohexanone oxime.
Figure 20B:
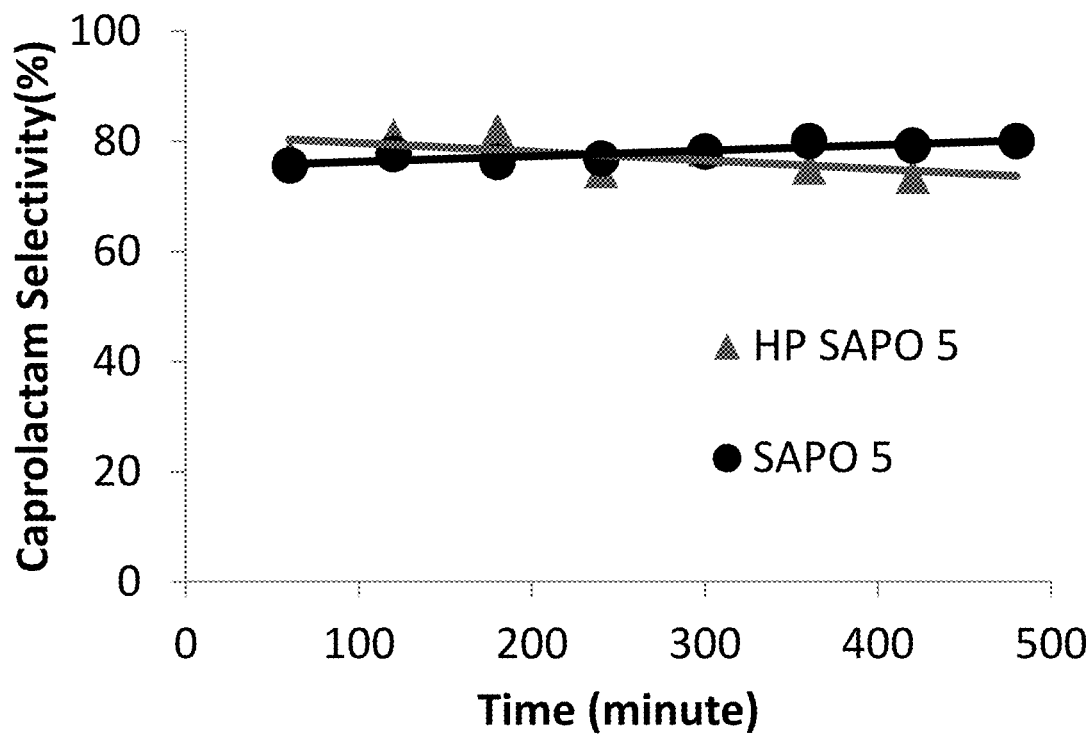
Figure 20C:
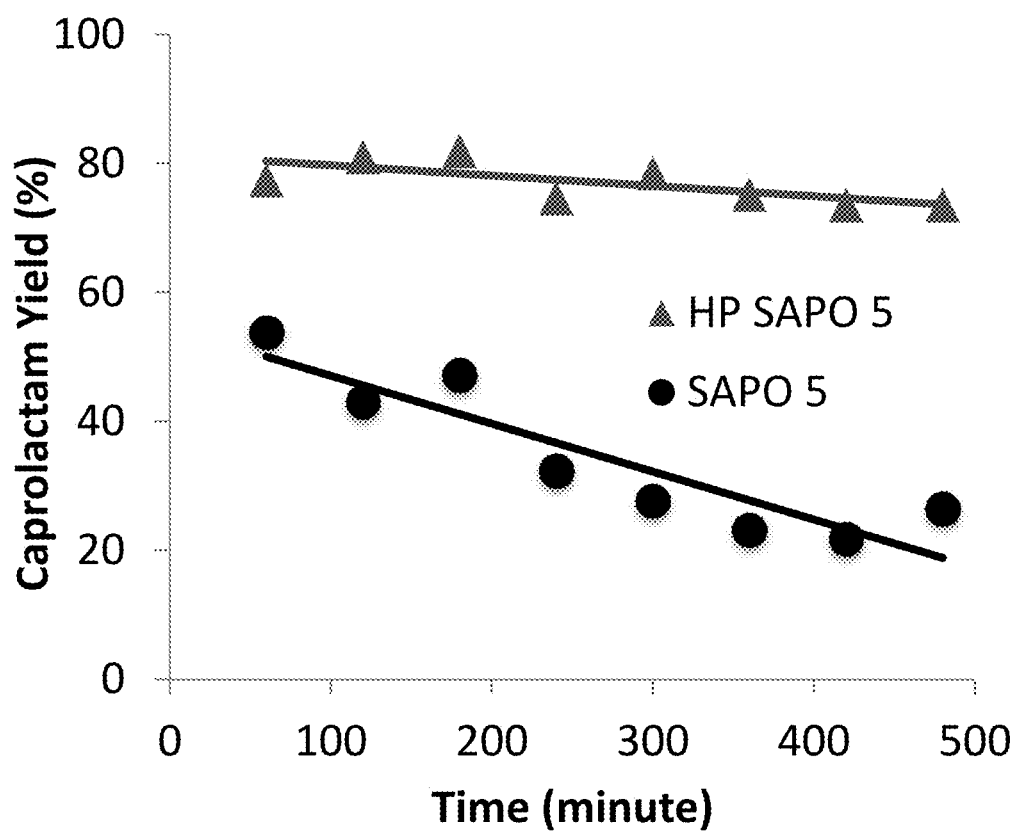

FIG. 20A shows the conversion of the microporous SAPO-5 and of the hierarchical HP SAPO-5, and FIG. 20B shows the selectivity for ε-caprolactam of the reaction. FIG. 20C shows the corresponding yield for the reactions.

Figure 20D:
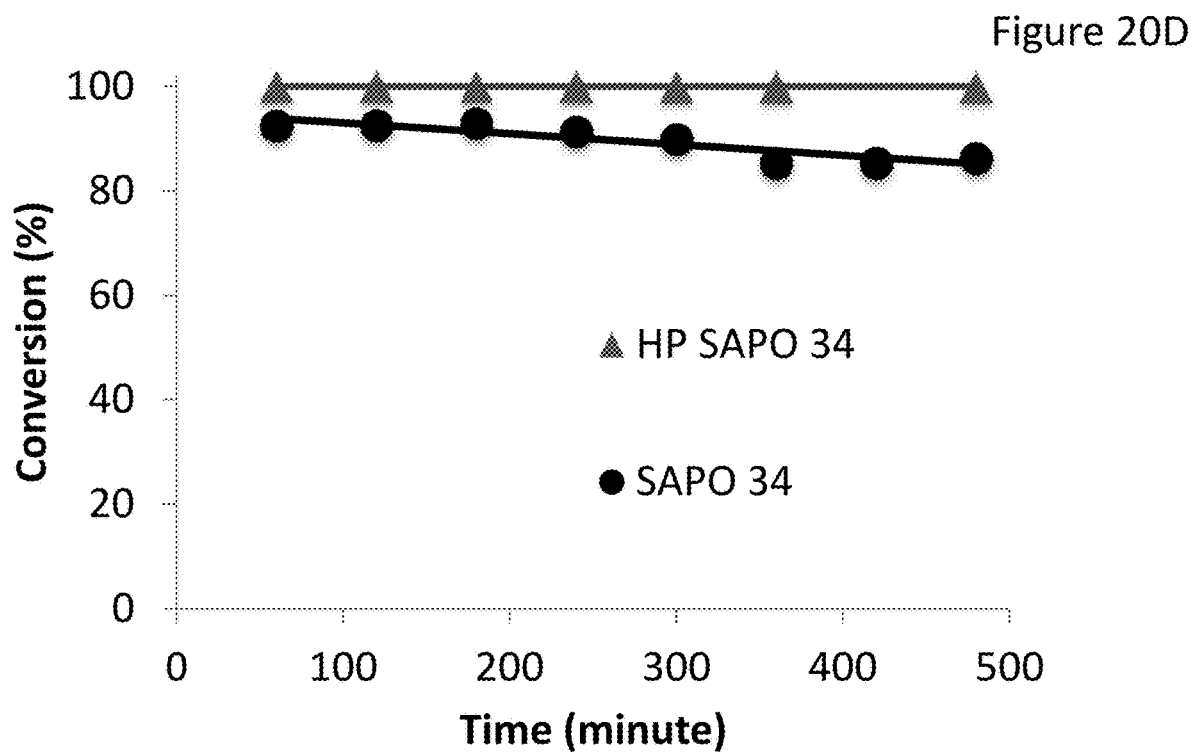
Figure 20E:
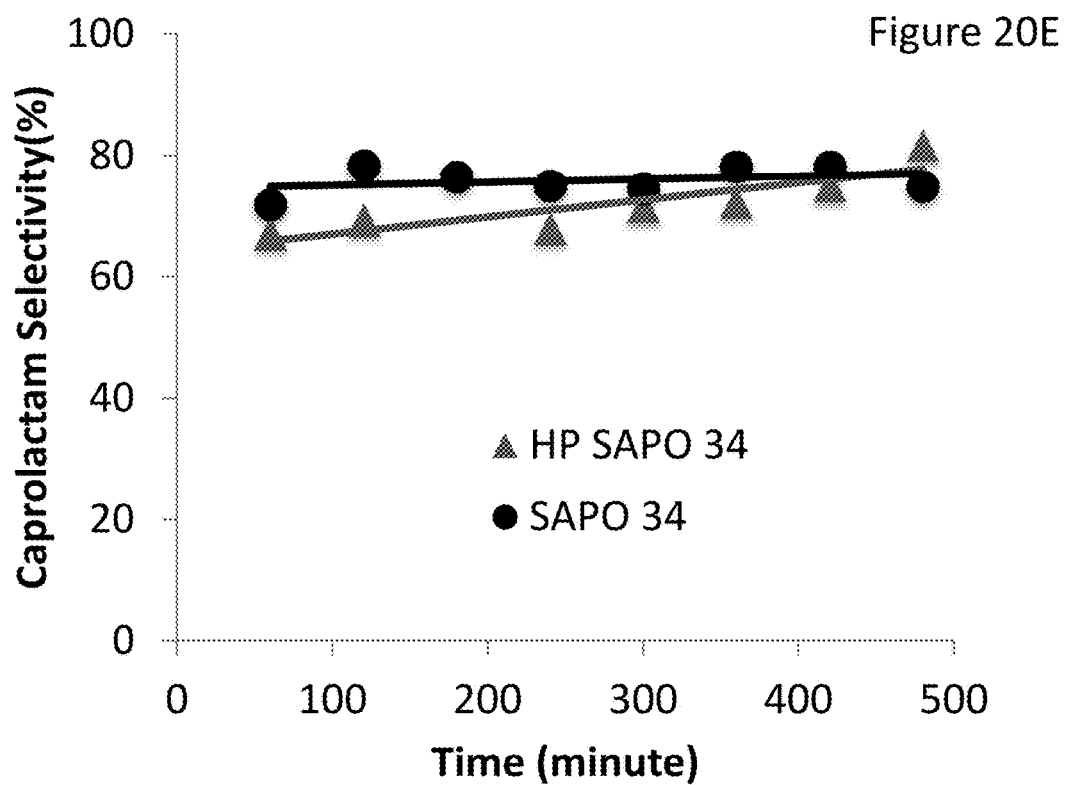
Figure 20F:
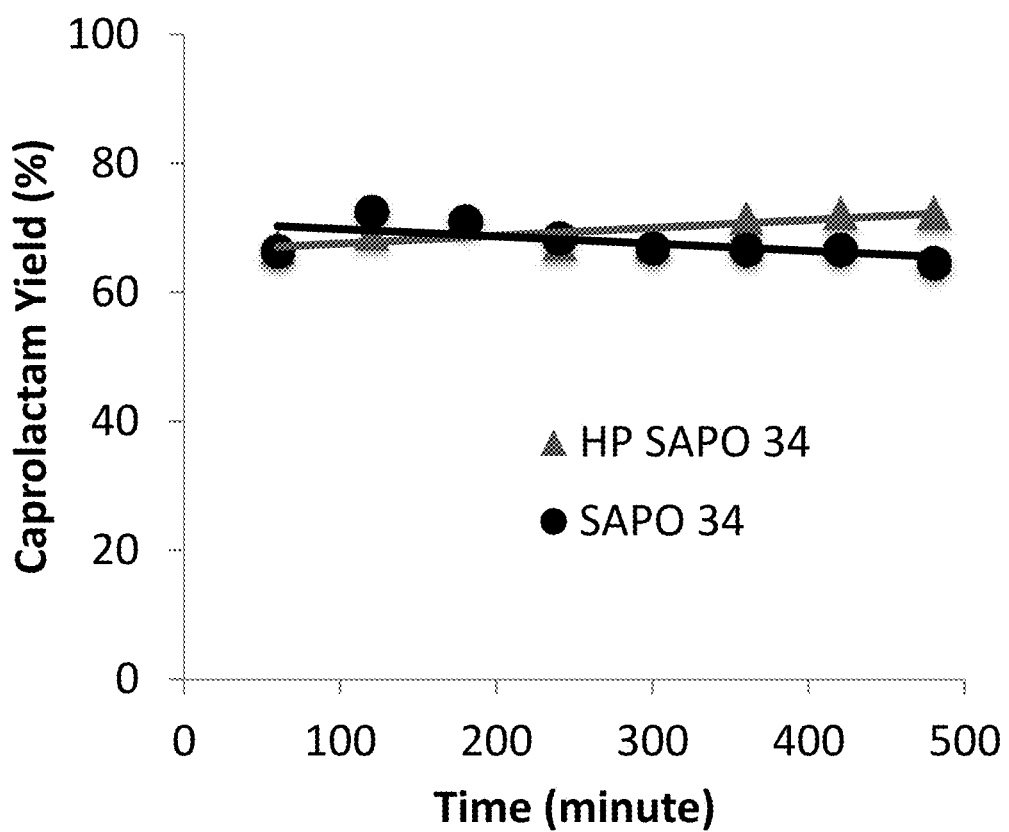

FIG. 20D shows the conversion of the microporous SAPO-34 and of the hierarchical HP SAPO-34, and FIG. 20E shows the selectivity for ε-caprolactam of the reaction. FIG. 20F shows the corresponding yield for the reactions.

As shown in FIGS. 20A-20F, the hierarchical catalysts provided superior performance compared to the microporous catalysts. The hierarchical catalysts were able to maintain both a constant conversion (FIGS. 20A, 20D), and relatively constant selectivity (FIGS. 20B, 20E), while the corresponding microporous catalysts appeared to deactivate. For example the HP SAPO-5 retains a >97% conversion whereas SAPO-5's activity started at 71% and dramatically dropped to just 33% over 7 hours.

Figure 20G:
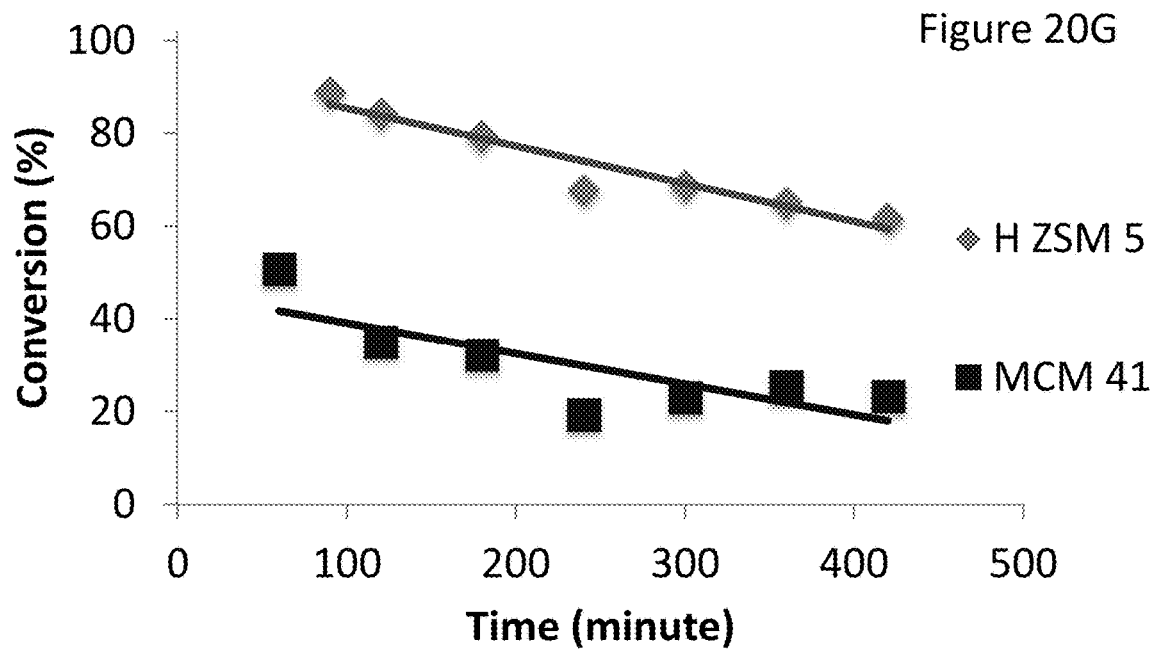
Figure 20H:
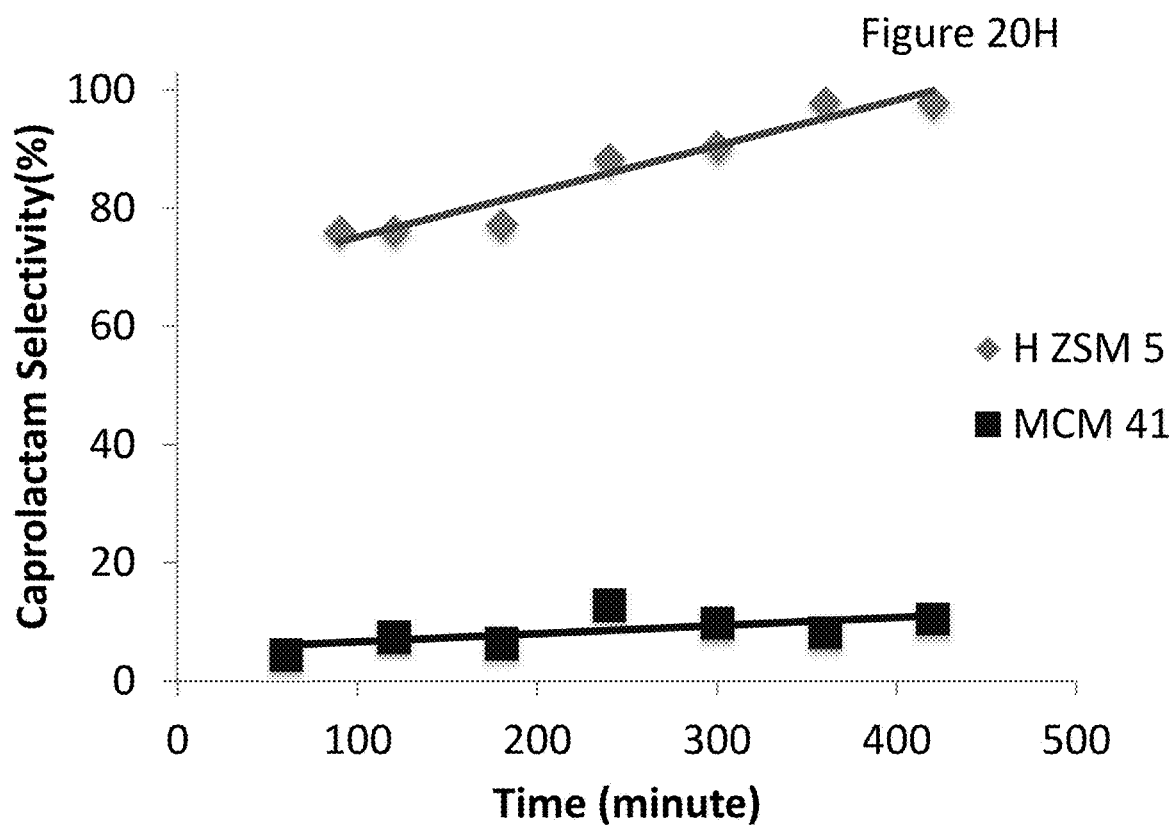
Figure 20I:
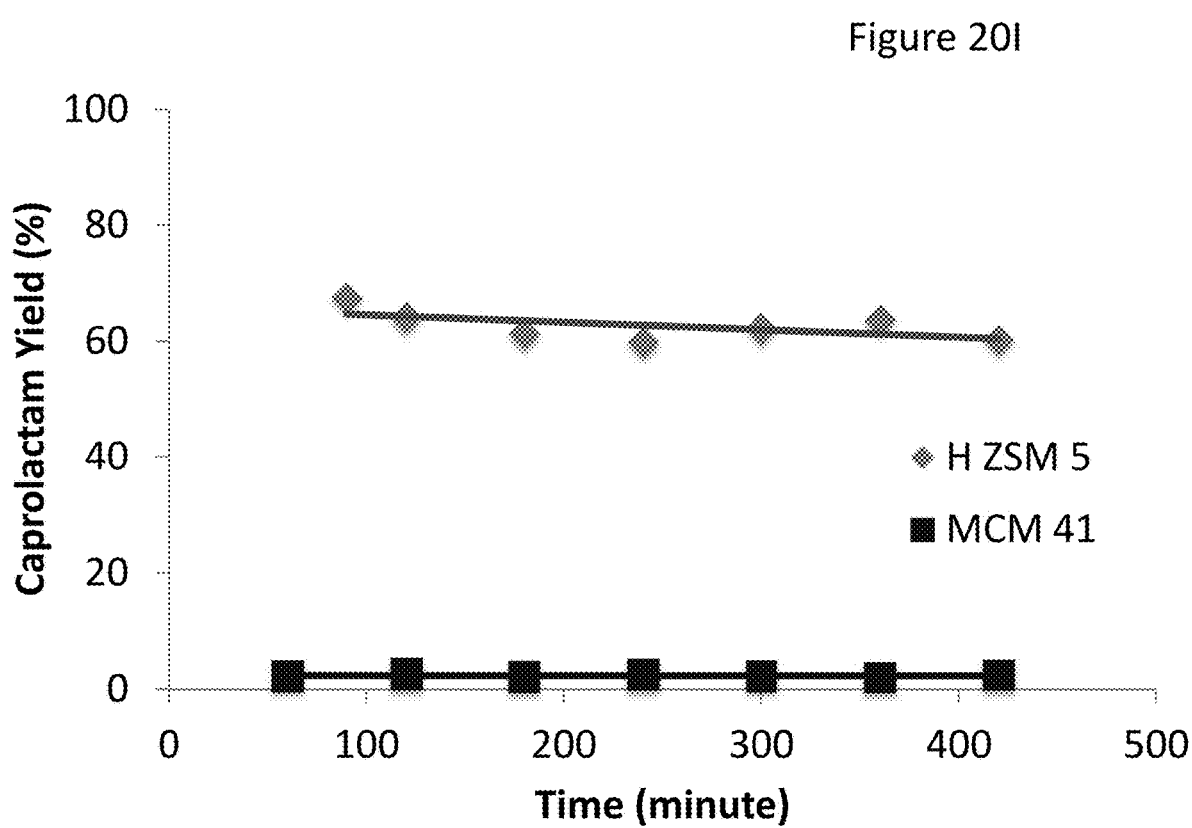

The performance of the industrial microporous catalyst H-ZSM-5 and the mesoporous MCM-41 catalysts was also investigated. The conversion of H-ZSM-5 and MCM-41 is shown in FIG. 20G, and the selectivities for ε-caprolactam are shown in FIG. 20H. FIG. 20I shows the corresponding yield for the reactions.

The microporous H-ZSM-5 catalyst, similar to the microporous SAPO-5 and SAPO-34, appeared to quickly deactivate. The mesoporous catalyst MCM-41 was quickly deactivated and exhibited much lower initial conversion and selectivity than the hierarchical catalysts.

The hierarchical materials generally provided high conversion and selectivity, as well as generally improved longevity compared to the remaining materials. Without wishing to be bound by any particular theory, it is believed that the microporous framework of the hierarchical catalysts provided active sites for the Beckmann rearrangement reaction, and that the connected mesopores provided enhanced diffusion of the cyclic oximes and/or lactams to and from the active sties.

An identical protocol was followed for the vapor phase Beckmann rearrangement of the more sterically demanding cyclooctanone oxime to form the corresponding caprylolactam (see FIG. 10).

Figure 21A:
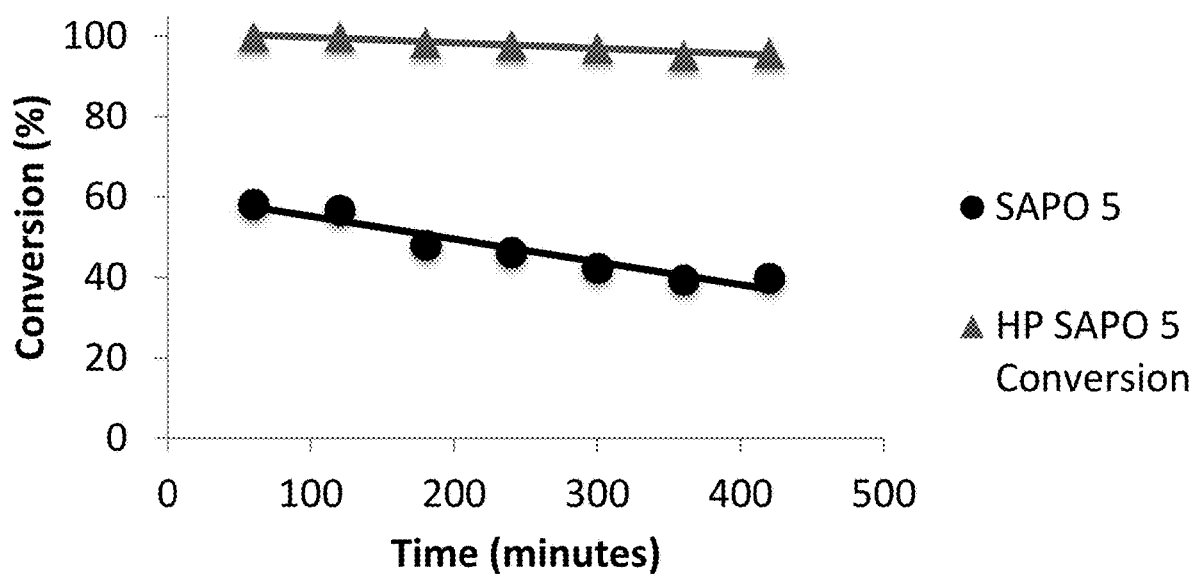
FIGS. 21A-21I are related to Example 5 and illustrate the conversion, selectivity, and yield of SAPO-5, HP SAPO-5, SAPO-34, HP SAPO-34, H-ZSM-5, and MCM-41 for the gas-phase Beckmann rearrangement of cyclooctanone oxime.
Figure 21B:
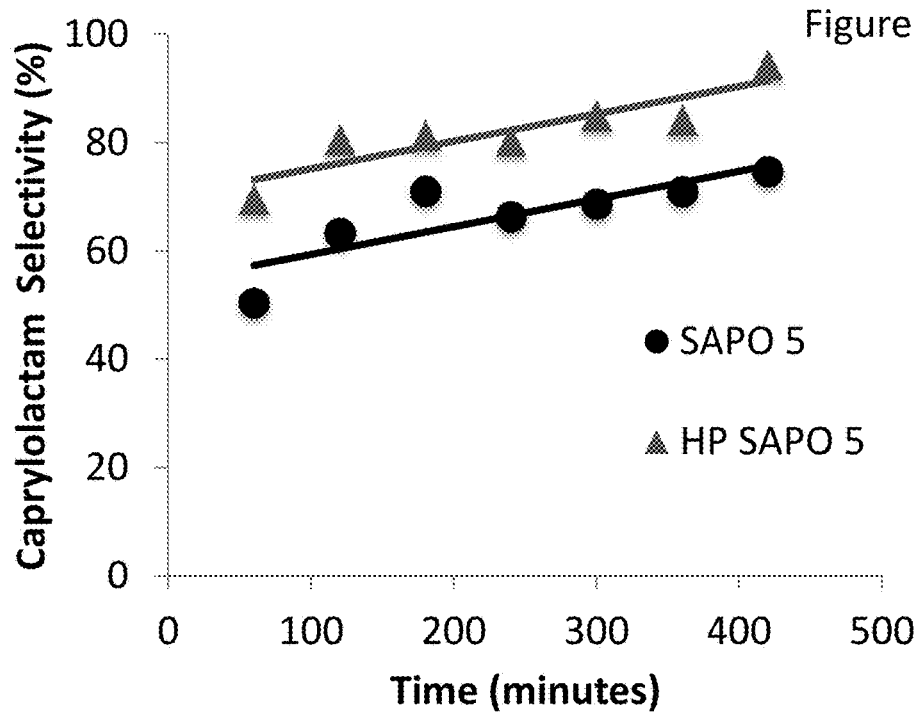
Figure 21C:
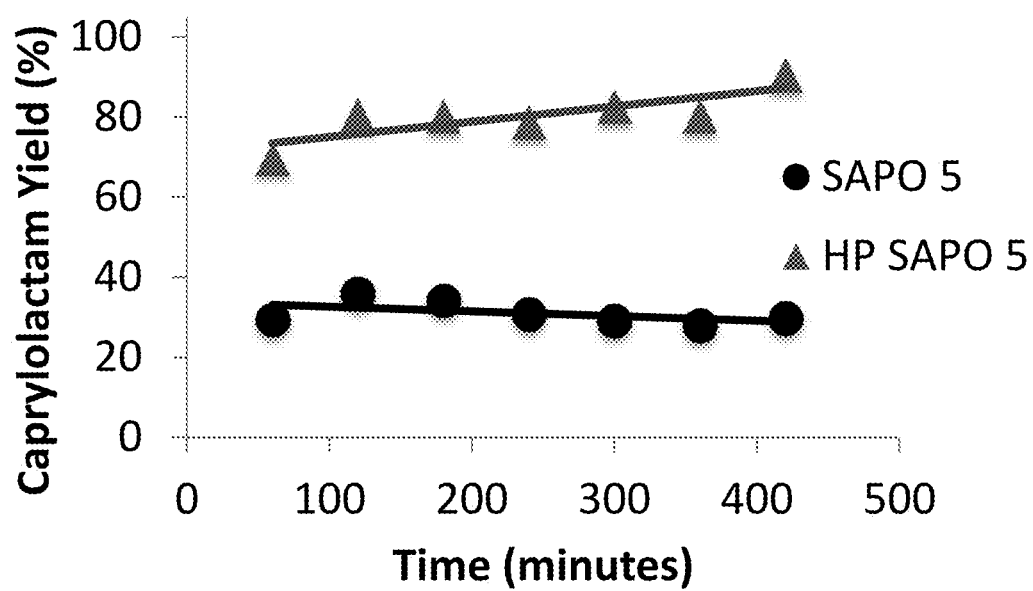

FIG. 21A shows the conversion of the microporous SAPO-5 and of the hierarchical HP SAPO-5, and FIG. 21B shows the selectivity for the desired lactam. FIG. 21C shows the corresponding yield for the reactions.

Figure 21D:
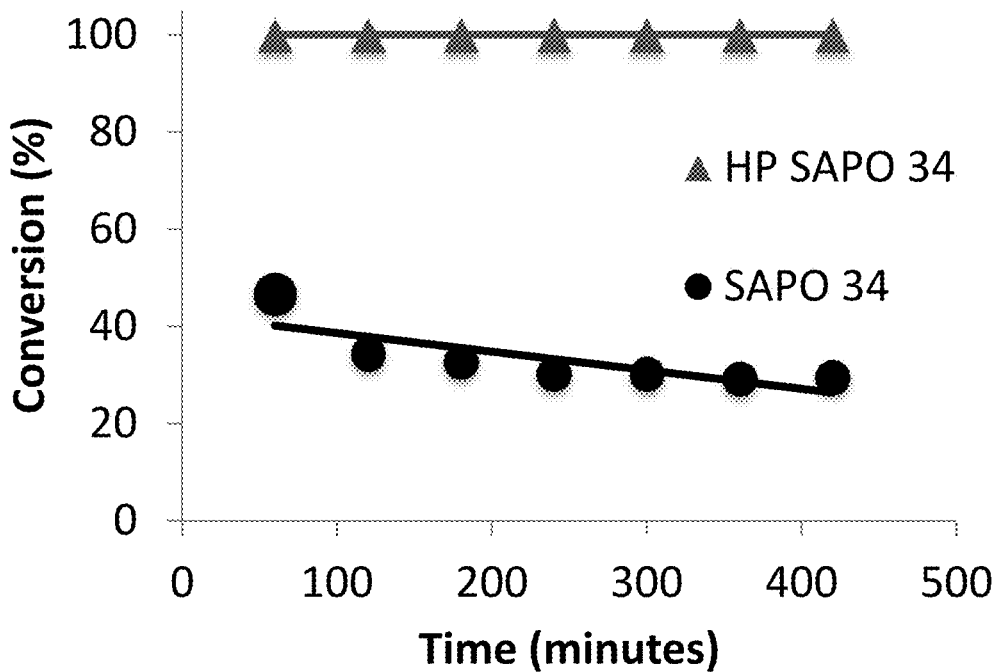
Figure 21E:
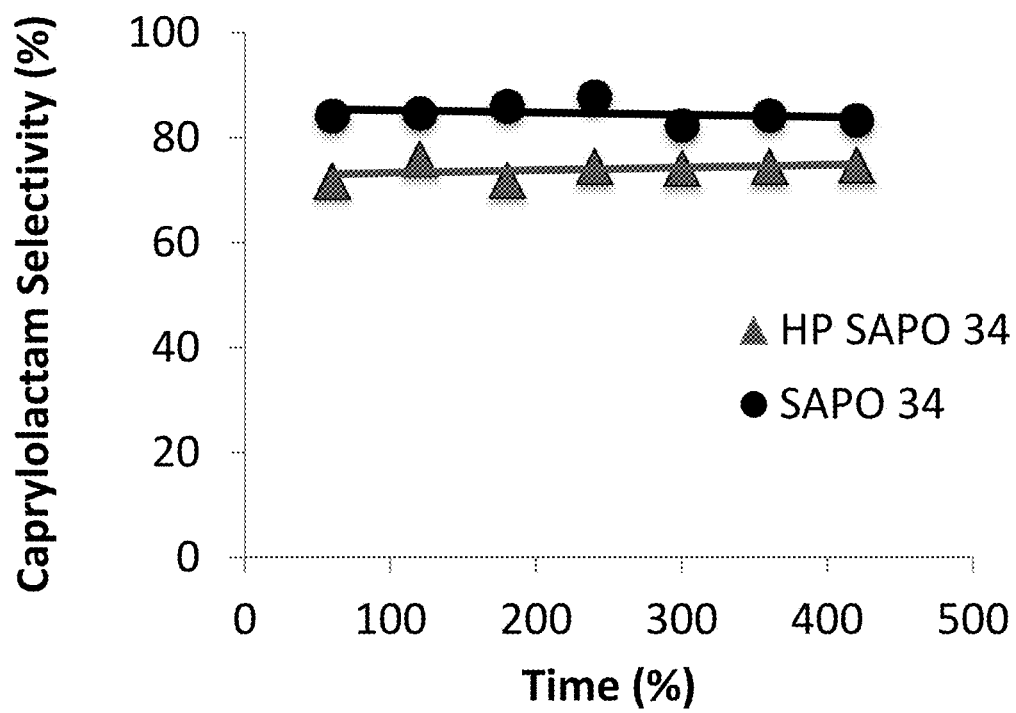
Figure 21F:
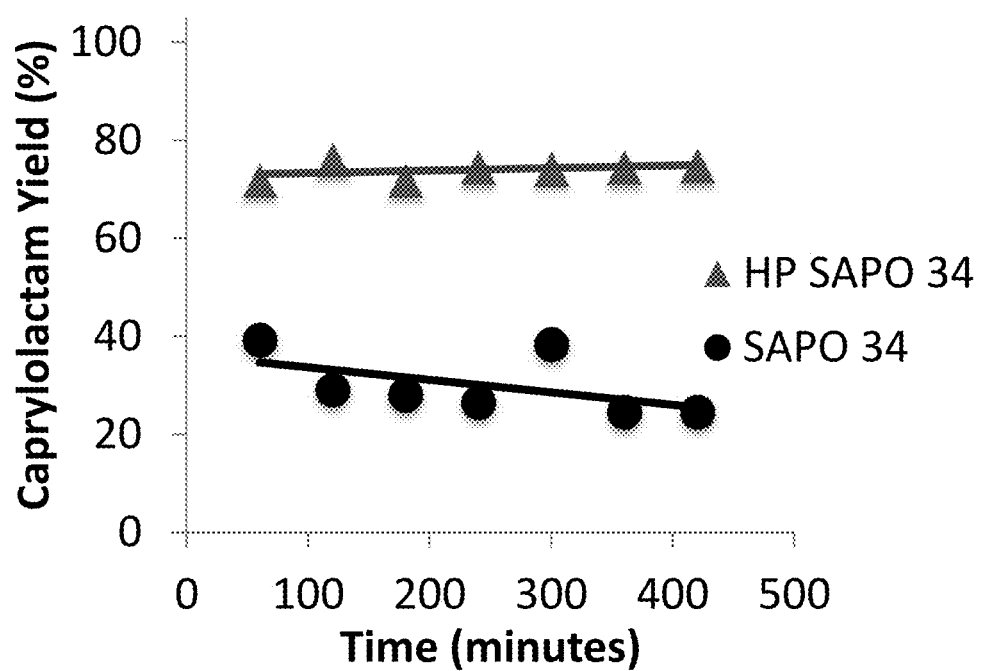

FIG. 21D shows the conversion of the microporous SAPO-34 and of the hierarchical HP SAPO-34, and FIG. 21E shows the selectivity for the desired lactam. FIG. 21F shows the corresponding yield for the reactions.

Figure 21G:
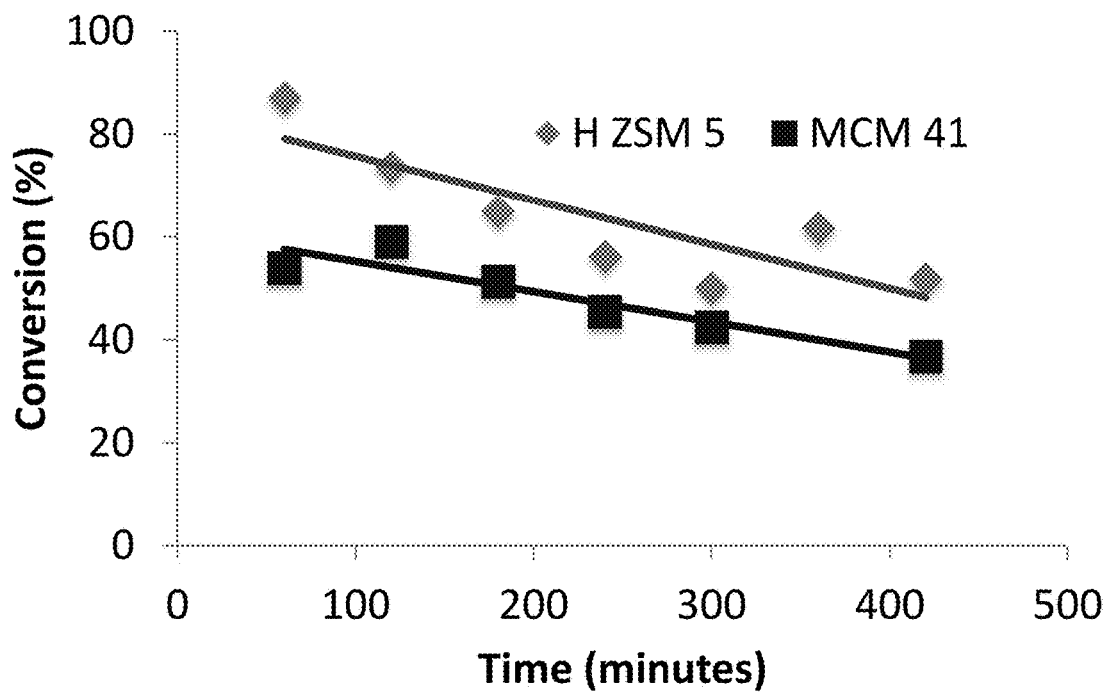
Figure 21H:
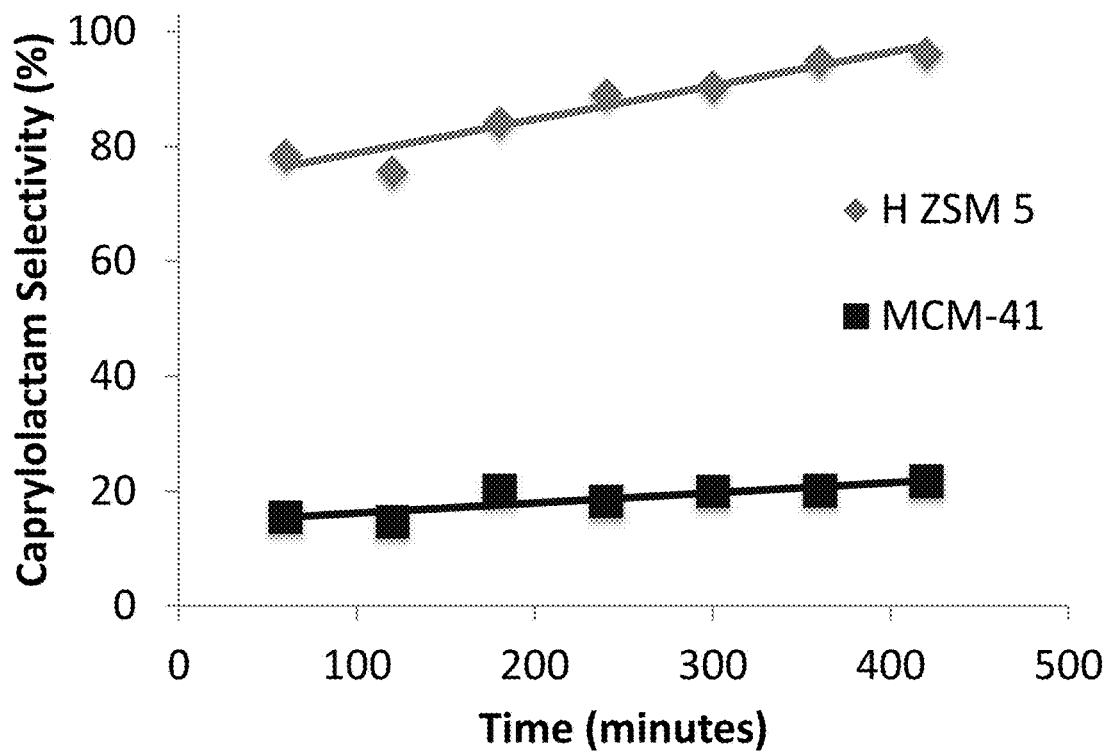
Figure 21I:
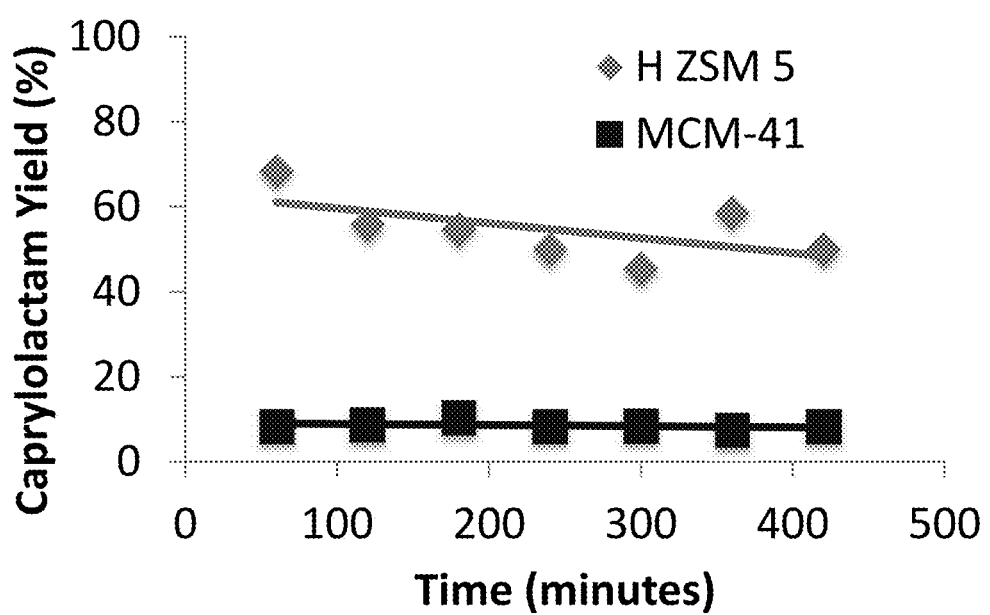

FIG. 21G shows the selectivity of the microporous H-ZSM-5 and the mesoporous MCM-41, and FIG. 21H shows the selectivity for the desired lactam. FIG. 20I shows the corresponding yield for the reactions.

For the cyclooctanone oxime reaction, both hierarchical catalysts provided relatively good selectivity.

With respect to SAPO-5 and HP SAPO-5, the selectivity was seen to increase over time. Without wishing to be held to any particular theory, this may suggest that that some of the original strong acid sites become blocked during the course of the reaction, leaving the desired weaker active sites to participate in the reaction more often, which in turn results in higher selectivity to the lactam. It is also possible that the acid sites are modified or modulated over the course of the reaction, thereby becoming more amenable/conducive to the desired selectivity over time. With respect to SAPO-34 and HP SAPO-34, the selectivity to the lactam remains fairly consistent during the course of the reaction.

As with the cyclohexanone oxime reaction, the hierarchical catalysts retained their high activities with cyclooctanone oxime over 7 hours, whereas the activities of the microporous catalysts were reduced significantly. In particular, the HP SAPO-34 is just as active in the rearrangement of cyclohexanone oxime as the rearrangement of cyclooctanone oxime, but the activity of the comparative microporous SAPO-34 in the rearrangement of cyclooctanone oxime is much lower, similar to H-ZSM-5.

Without wishing to be held to any particular theory, it is believed that this could be due to the reaction occurring in the pore mouth of the catalyst, which would be inaccessible to the larger cyclooctanone oxime. Hence by including mesopores into the catalyst it is possible to increase the accessibility of the active sites towards the bulky substrates resulting in higher conversions than the microporous analogues. Alternatively, or in addition to the above, the improvements seen in the hierarchical catalyst could be ascribed to the presence of the additional silanol sites, as these sites appear to be the common feature in both hierarchical catalysts. These silanols may attenuate the hydrophobic properties of the catalyst and this might result in the catalyst having protection against deactivation.

As shown in FIGS. 20 and 21, the hierarchical catalysts provided similar active sites compared to their microporous analogues, while retaining high conversion levels over the course of the observed reaction time.

Figure 22A:
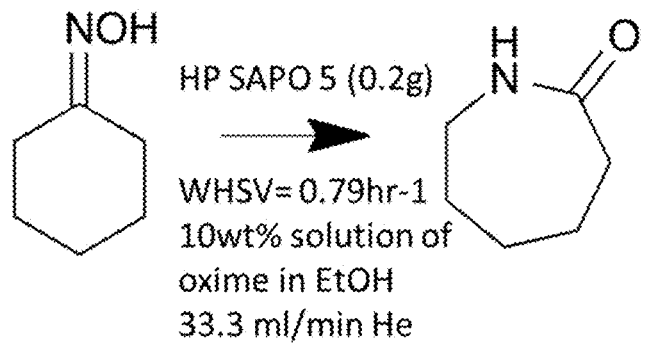
FIGS. 22A-22C are related to Example 5 and illustrate the conversion and selectivity for the gas-phase Beckmann rearrangement of cyclohexanone oxime with HP SAPO-5 at various temperatures.
Figure 22B:
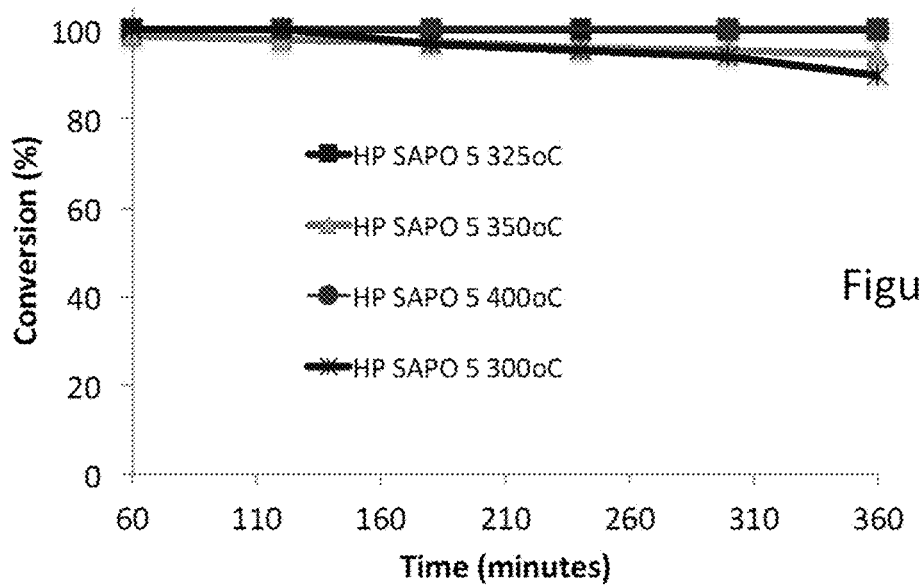
Figure 22C:
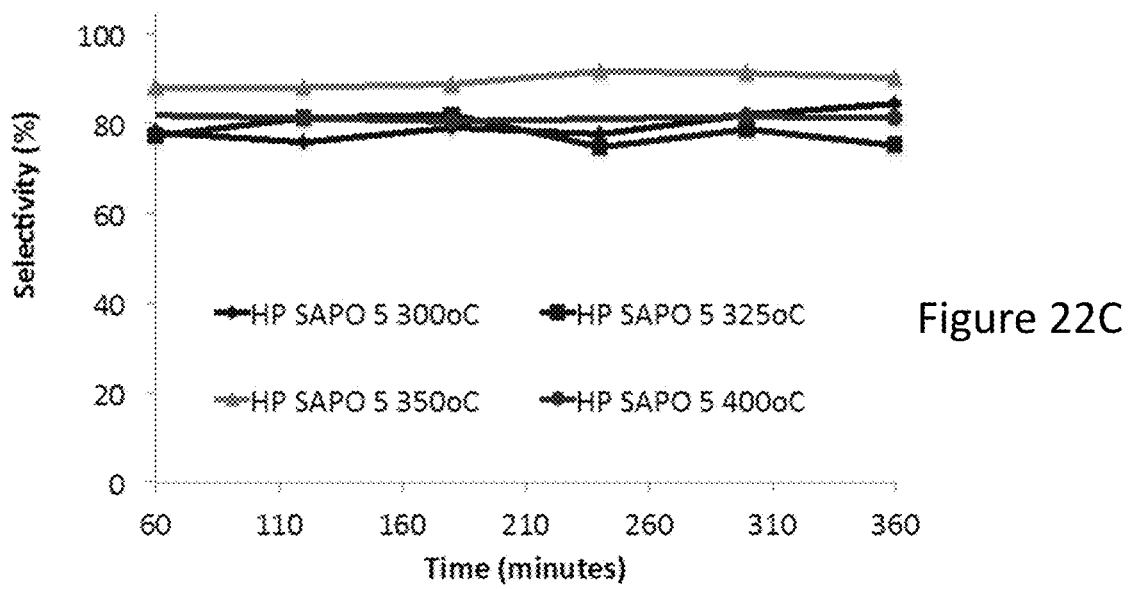

The effect on the reaction of temperature was investigated. As shown in FIG. 22A, a weight hourly space velocity (WHSV) of 0.79 $hr^{-1}$ cyclohexanone oxime were provided to a reactor containing 0.2 g of catalyst as a 10 wt. % solution of the oxime in ethanol. The reaction was run at 300° C., 325° C., 350° C., and 400° C. The conversion and selectivity of the reaction for ε-caprolactam as a function of time is shown in FIGS. 22B and 22C.

Figure 23A:
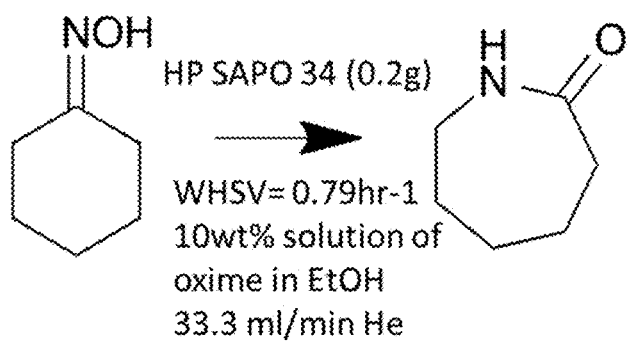
FIGS. 23A-23C are related to Example 5 and illustrate the conversion and selectivity for the gas-phase Beckmann rearrangement of cyclohexanone oxime with HP SAPO-34 at various temperatures.
Figure 23B:
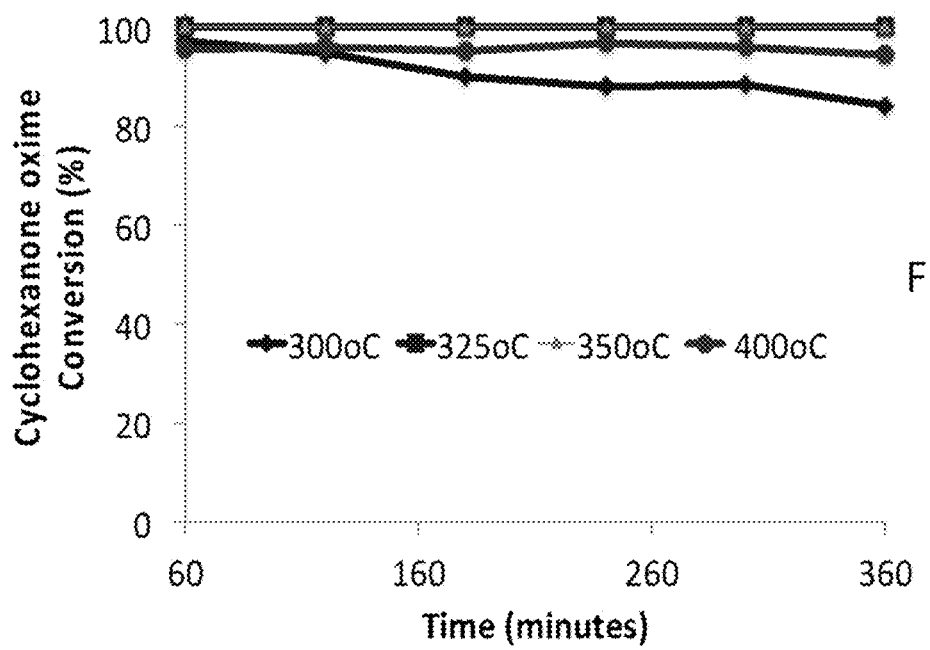
Figure 23C:
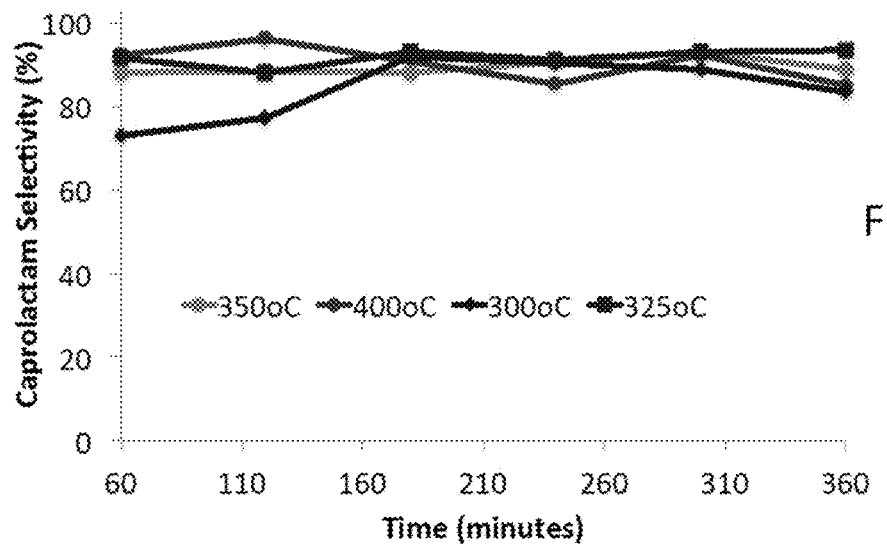

As shown in FIG. 23A, a similar experiment was conducted using HP SAPO-34 as the catalyst. The reaction was run at 300° C., 325° C., 350° C., and 400° C. The conversion and selectivity of the reaction for ε-caprolactam as a function of time is shown in FIGS. 23B and 23C.

As shown in FIGS. 22A-22C and 23A-23C, both HP SAPO-5 and HP SAPO-34 are stable in the vapor phase Beckmann rearrangement of cylcohexanone oxime over a range of temperatures. High selectivities and conversions are retained over the reaction time and structural integrity of the catalyst was also maintained.

Figure 24A:
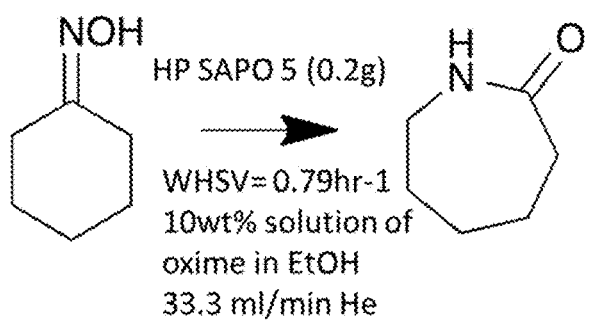
FIGS. 24A-24C are related to Example 5 and illustrate the conversion and selectivity for the gas-phase Beckmann rearrangement of cyclohexanone oxime with HP SAPO-5 at various WHSV.

The effect on the reaction of oxime concentration was investigated. As shown in FIG. 24A, cyclohexanone oxime was provided to a reactor containing 0.2 g of catalyst as a 10 wt. % solution of the oxime in ethanol. The reaction was run at 325° C.

Figure 24B:
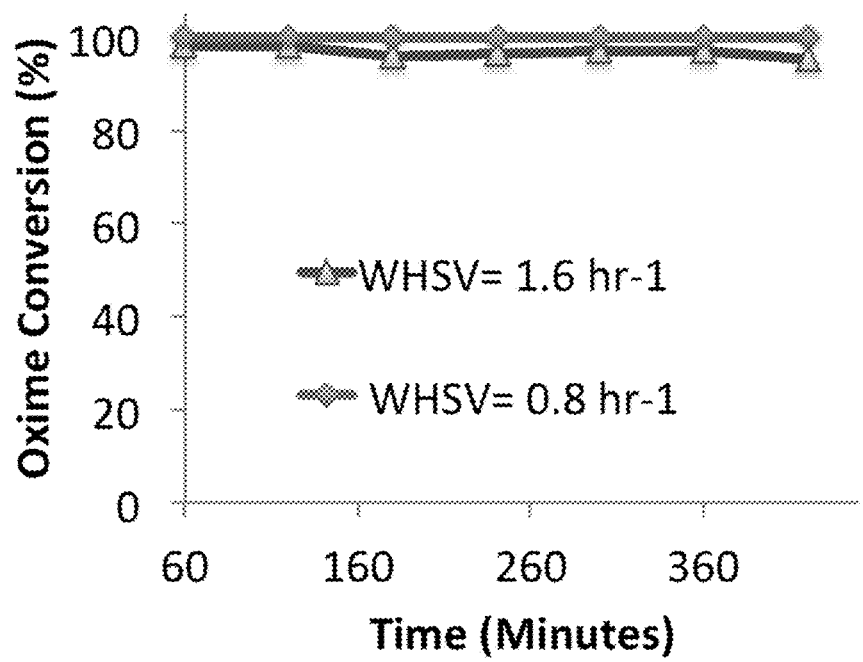
Figure 24C:
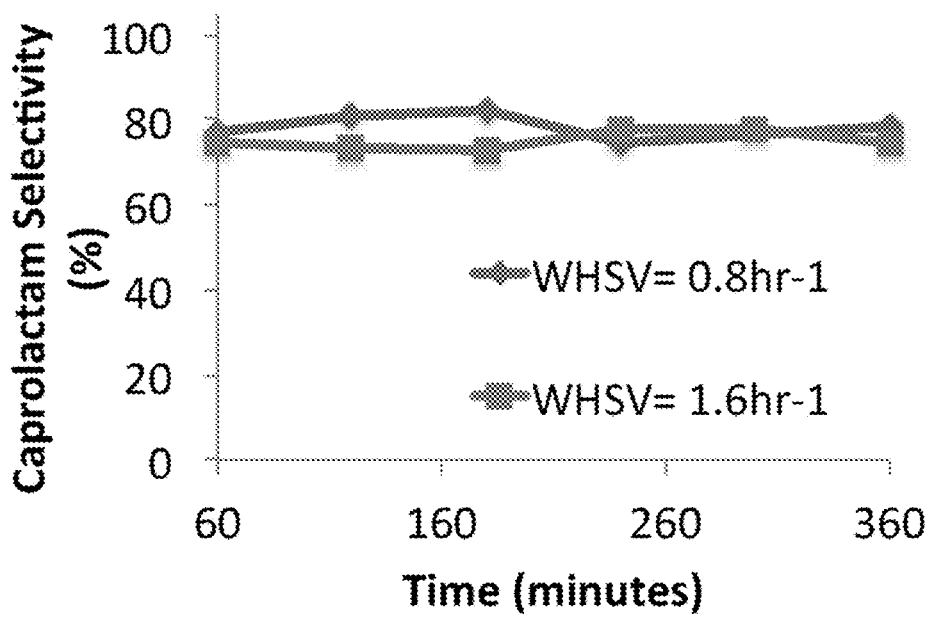

The flow rate of cyclohexanone oxime was varied between 0.8 $hr^{-1}$ and 1.6 $hr^{-1}$. The conversion and selectivity of the reaction for ε-caprolactam as a function of time is shown in FIGS. 24B and 24C.

As shown in FIG. 23A, a similar experiment was conducted using HP SAPO-34 as the catalyst. The reaction was run at 0.8 $hr^{-1}$, and 1.6 $hr^{-1}$ cyclohexanone oxime. The conversion and selectivity of the reaction for ε-caprolactam as a function of time is shown in FIGS. 25B and 25C.

Figure 25A:
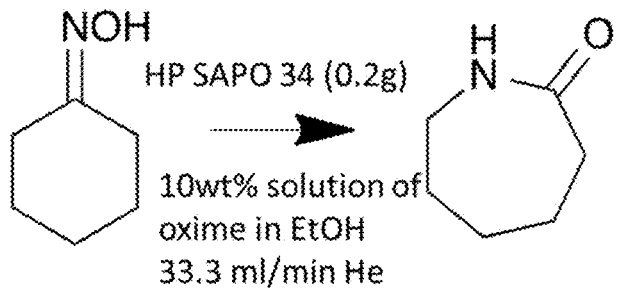
FIGS. 25A-25C are related to Example 5 and illustrate the conversion and selectivity for the gas-phase Beckmann rearrangement of cyclohexanone oxime with HP SAPO-34 at WHSV.
Figure 25B:
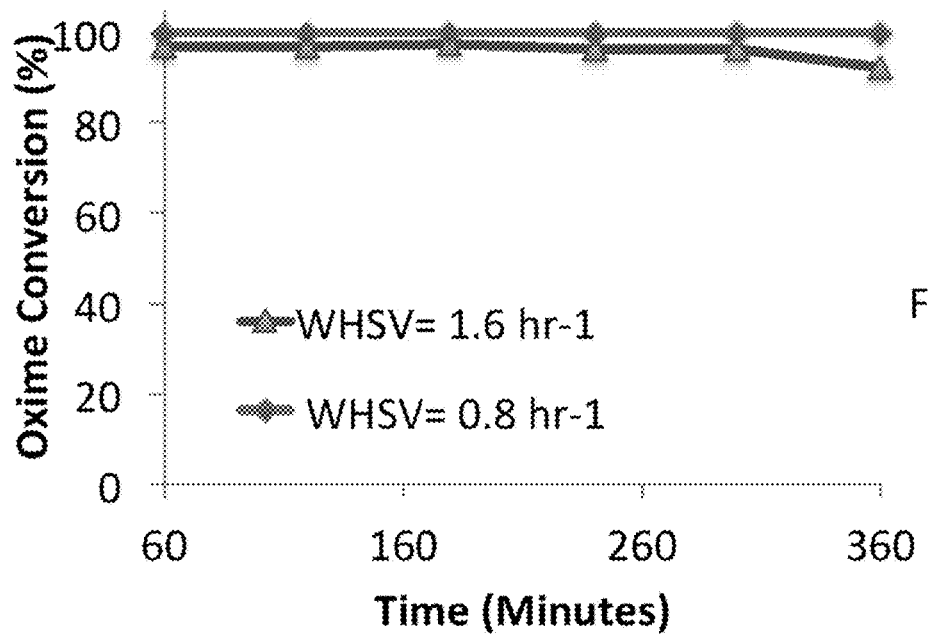
Figure 25C:
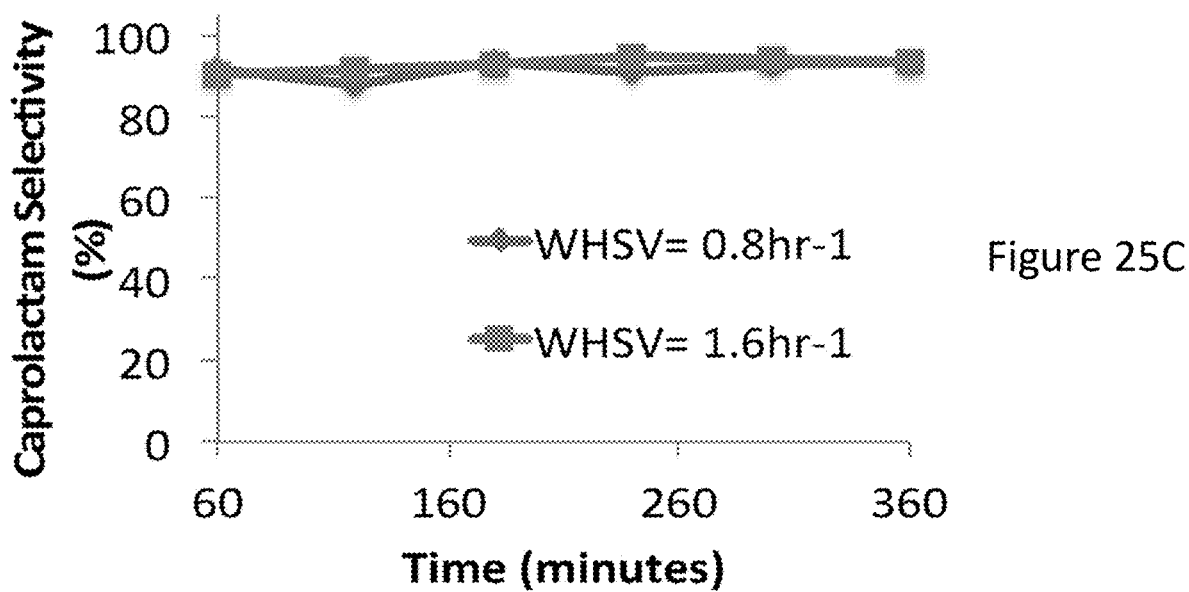

As shown in FIGS. 24 and 25, HP SAPO-5 and HP SAPO-34 maintain high conversion and selectivity over a range of WHSV values, further supporting the stability and versatility of the catalysts.

Example 6: Liquid Beckmann Rearrangement of Cyclohexanone Oxime and Cyclooctanone Oxime Cyclohexanone oxime (0.1 g), internal standard anhydrous chlorobenzene (0.1 g) and freshly calcined catalyst (0.1 g) were added to anhydrous benzonitrile (20 ml) in a 3-necked batch reactor flask at 130° C. under reflux and nitrogen. The resulting suspension was stirred magnetically at the reaction temperature. Over the course of the reaction aliquots of the reaction mixture were taken and analyzed via GC.

Figure 26:
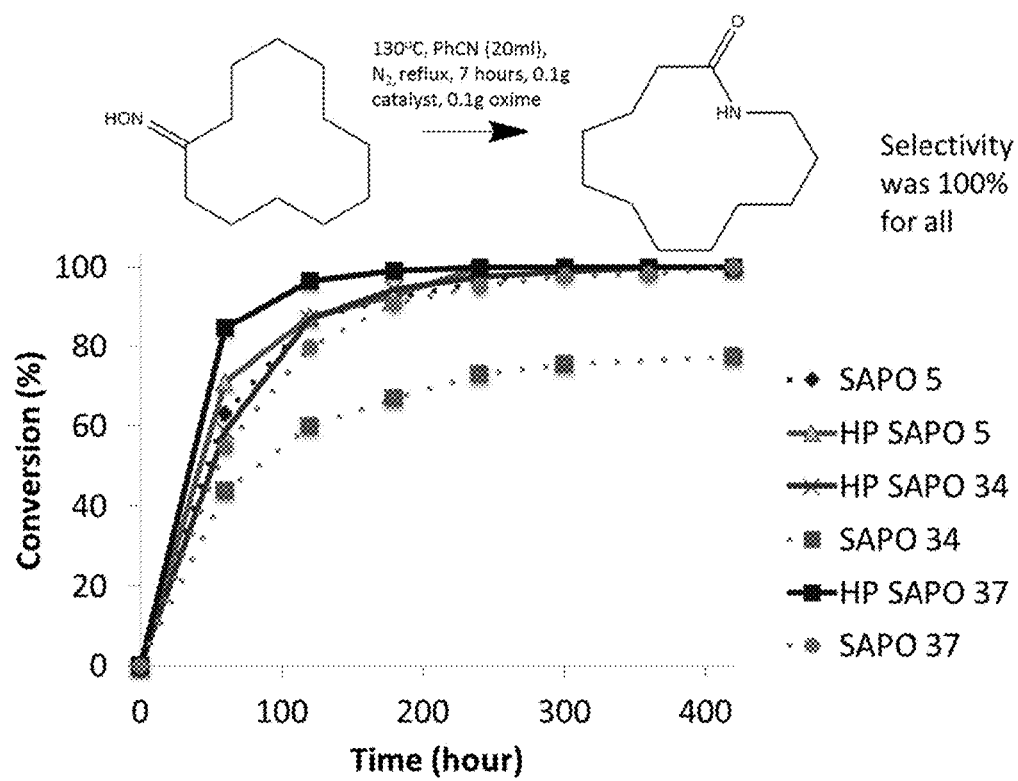
FIG. 26 is related to Example 6 and illustrates the conversion of cyclododecanone oxime with different catalysts.

The conversions of the HP SAPO-5, HP SAPO-34 and HP SAPO-37 catalysts in the liquid phase rearrangement of cyclododecanone oxime to laurolactam as a function of time are provided in FIG. 26. The reaction was run at 130° C. under nitrogen with PhCN (20 ml) as the solvent. 0.1 g of the catalyst was provided to the reactor along with 0.1 g of the oxime, and allowed to reflux for 7 hours.

As shown in FIG. 26, comparative performance of the microporous and hierarchical catalysts in the liquid-phase Beckmann rearrangement of cyclododecanone oxime, with the hierarchical analogues displaying enhanced rates at lower contact times. In addition, the smaller pore (3.8 Å) microporous SAPO-34 has a much inferior performance (mass-transfer and diffusion limitations) compared with its hierarchical analogue, thereby highlighting the catalytic potential of the latter with bulkier substrate molecules. HP SAPO-5, HP SAPO-34 and HP SAPO-37 are all active in the liquid phase Beckmann rearrangement of cycloddodecanone oxime to laurolactam. They each reach 100% conversion with 100% selectivity by 5 hours. All the HP SAPOs are more active than their microporous analogues, illustrating the benefits of having more accessible active sites within a hierarchically porous framework.

Figure 27A:
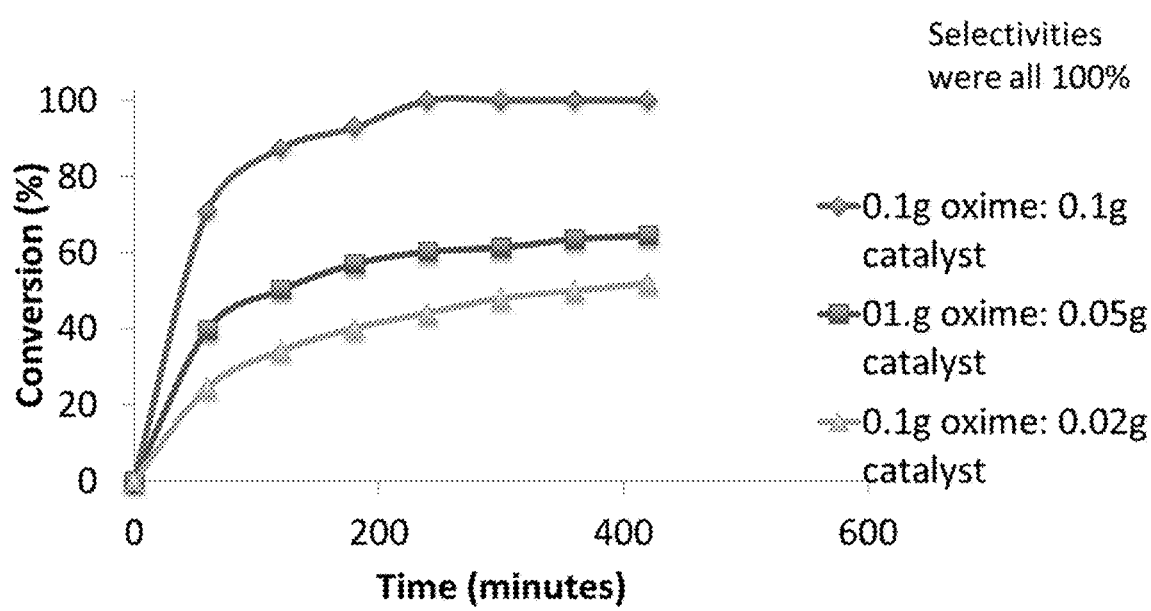
FIG. 27A is related to Example 6 and illustrates the conversion of cyclododecanone oxime in the liquid phase with HP SAPO-5 with different quantities of catalyst.
Figure 27B:
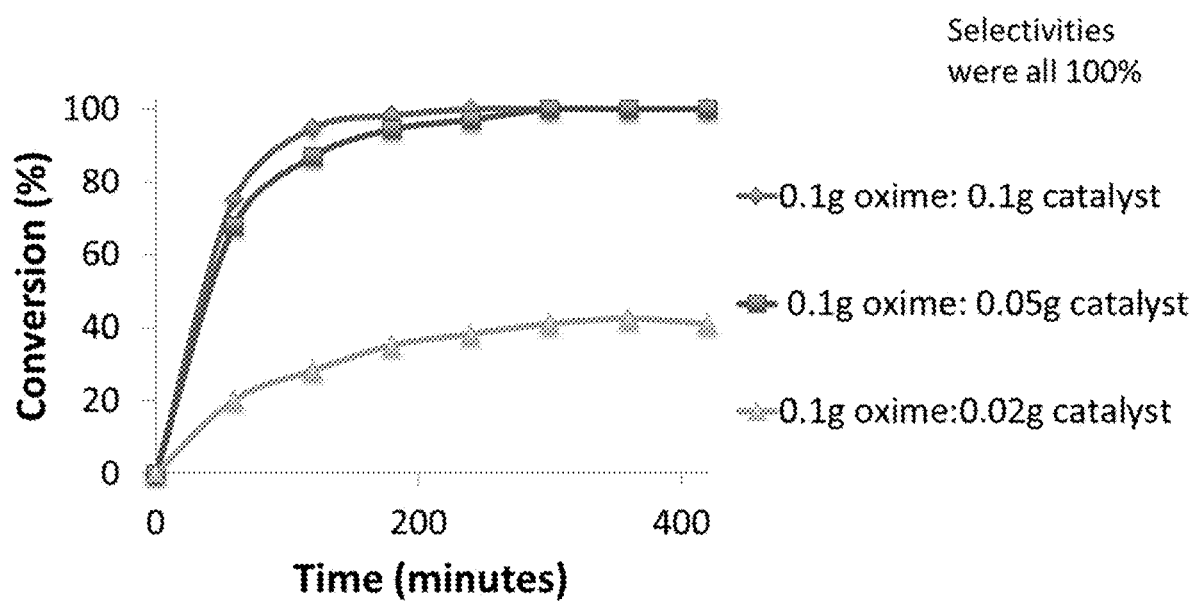
FIG. 27B is related to Example 6 and illustrates the conversion of cyclododecanone oxime in the liquid phase with HP SAPO-34 with different quantities of catalyst.
Figure 27C:
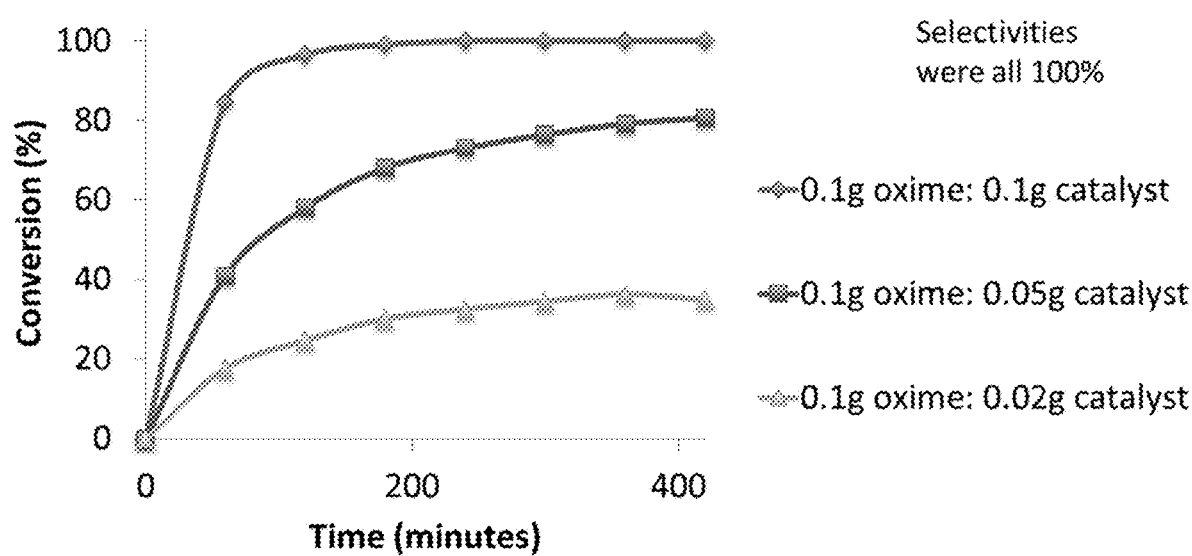
FIG. 27C is related to Example 6 and illustrates the conversion of cyclododecanone oxime in the liquid phase with HP SAPO-37 with different quantities of catalyst.

The effect on the reaction of cyclododecanone oxime of the amount of catalyst was investigated. As shown in FIGS. 27A-27C, the amount of catalyst was varied from 0.02 g catalyst per 0.1 g oxime to 0.1 g catalyst per 0.1 g oxime. FIG. 27A illustrates the results for HP SAPO-5. FIG. 27B illustrates the results for HP SAPO-34. FIG. 27C illustrates the results for HP SAPO-37.

The effect on the reaction of cyclododecanone oxime catalyzed with HP SAPO-34 of the temperature was investigated. The results are provided in Table 2.

TABLE 2

Conversion, selectivity, and yield of cyclododecanone oxime at various temperatures

| Temperature (° C.) | Time (minutes) | Conversion (mol %) | Selectivity (mol %) | Yield (mol %) |
|---|---|---|---|---|
| 110 | 60 | 26.3 | 100 | 26.3 |
| 110 | 120 | 44.2 | 100 | 44.2 |
| 110 | 180 | 56.4 | 100 | 56.4 |
| 110 | 240 | 67.8 | 100 | 67.8 |
| 110 | 300 | 74.0 | 100 | 74.0 |

TABLE 2-continued

Conversion, selectivity, and yield of cyclododecanone oxime at various temperatures

| Temperature (° C.) | Time (minutes) | Conversion (mol %) | Selectivity (mol %) | Yield (mol %) |
|---|---|---|---|---|
| 110 | 360 | 78.6 | 100 | 78.6 |
| 110 | 420 | 83.0 | 100 | 83.0 |
| 130 | 60 | 58.6 | 100 | 58.6 |
| 130 | 120 | 86.9 | 100 | 86.9 |
| 130 | 180 | 94.4 | 100 | 94.4 |
| 130 | 240 | 97.7 | 100 | 97.7 |
| 130 | 300 | 98.8 | 100 | 98.8 |
| 130 | 360 | 100 | 100 | 100 |
| 130 | 420 | 100 | 100 | 100 |
| 150 | 60 | 82.1 | 100 | 82.1 |
| 150 | 120 | 94.9 | 100 | 94.9 |
| 150 | 180 | 98.4 | 100 | 98.4 |
| 150 | 240 | 100 | 100 | 100 |
| 150 | 300 | 100 | 100 | 100 |
| 150 | 360 | 100 | 100 | 100 |
| 150 | 420 | 100 | 100 | 100 |

As shown in Table 2, HP SAPO-34 has been tested over a range of reaction temperatures including 110° C., 130° C. and 150° C. The rate of reaction improved significantly as a function of increasing temperature. Under all the conditions the catalyst reaches maximum conversion with 100% selectivity to the desired lactam.

Figure 28A:
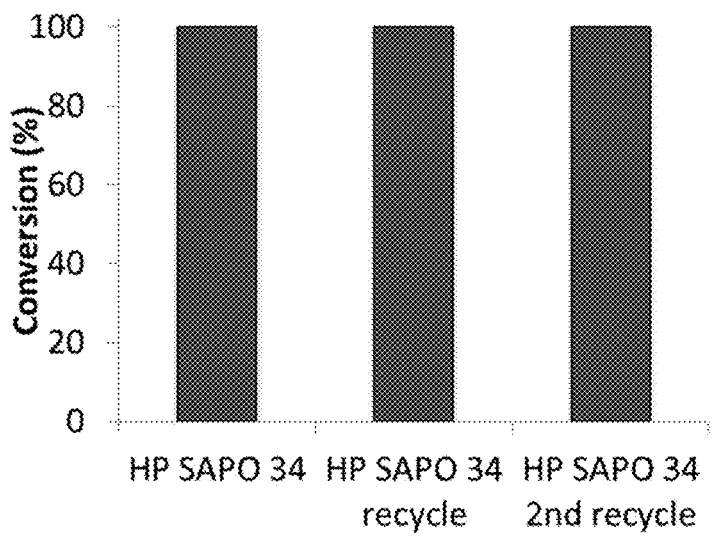
FIGS. 28A-28C are related to Example 6 and illustrate the conversion of HP SAPO-34, HP SAPO-5, and HP SAPO-37, respectively, using a liquid recycle set-up.
Figure 28B:
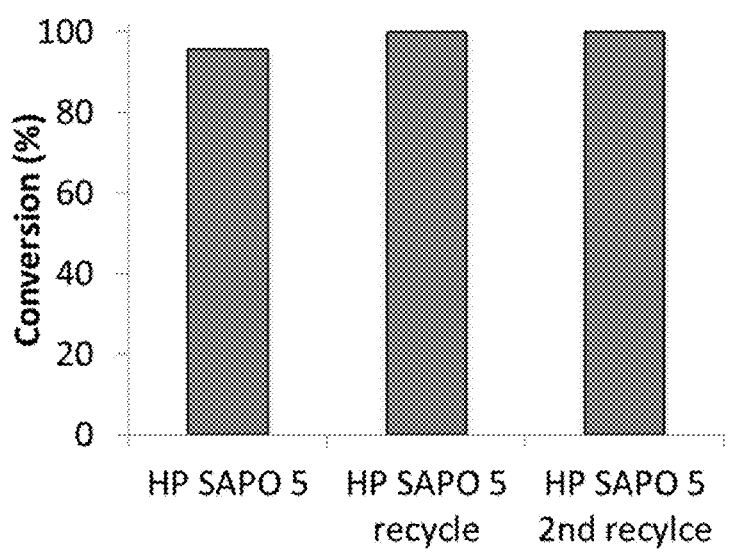
Figure 28C:
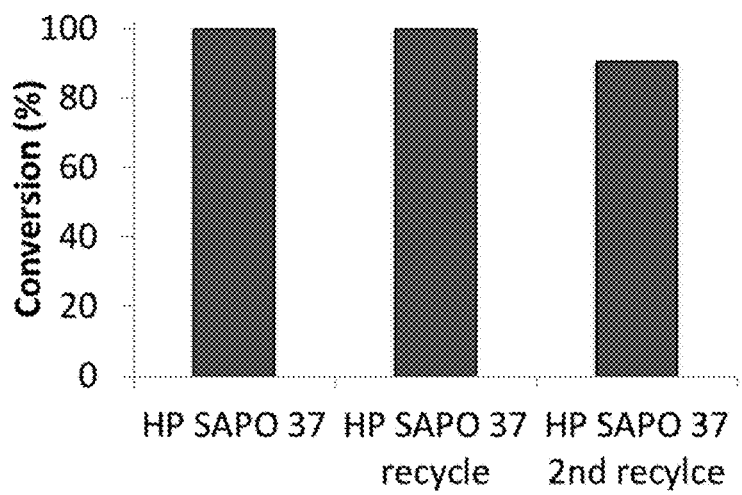

Referring next to FIGS. 28A-28C, a recycle experiment was conducted for each catalyst for the Beckmann rearrangement of cyclododecanone oxime. Cyclohexanone oxime, internal standard anhydrous chlorobenzene, and freshly calcined recovered catalyst were added to anhydrous benzonitrile in a 3-necked batch reactor, with a 1:1:1:30.6 weight ratio respectively, at 130° C. under reflux and nitrogen. The resulting suspension was stirred magnetically at the reaction temperature. Over the course of the reaction aliquots of the reaction mixture were taken and analyzed via GC. Conversion was determined after 7 hours. FIG. 28A illustrates the change in percent conversion for each recycle using the HP SAPO-34 catalyst. FIG. 28B illustrates the change in percent conversion for each recycle using the HP SAPO-5 catalyst. FIG. 28C illustrates the change in percent conversion for each recycle using the HP SAPO-34 catalyst.

As illustrated in FIGS. 28A-28C, HP SAPO-5, HP SAPO-34 and HP SAPO-37 all retain structural integrity and demonstrated sustained catalytic performance (near 100% conversion) after the recycle tests.

Example 7: Characterization of Catalysts Acidic Properties

From Example 4, it was observed that the hierarchical catalysts exhibited improved longevity in the reactions. This suggests minimal coking is occurring in these systems. Coking can occur if acid sites are too strong and therefore, do not permit the desorption of the product, or it can occur if diffusion is hindered therefore preventing the egress of products. Without wishing to be bound by any particular theory, it is believed that the hierarchical catalysts acidity is attenuated by the presence of mesopores and that the mesopores are aiding the mass transport of substrates and products.

Therefore to further establish the origin of these improvements, the structural properties ($N_2$ adsorption desorption isotherms and electron microscopy) and acidic properties (NMR, TPD-$NH_3$ FT-IR using CO and collidine as a probe molecule) of the catalysts were further investigated.

Solid State NMR

Figure 29A:
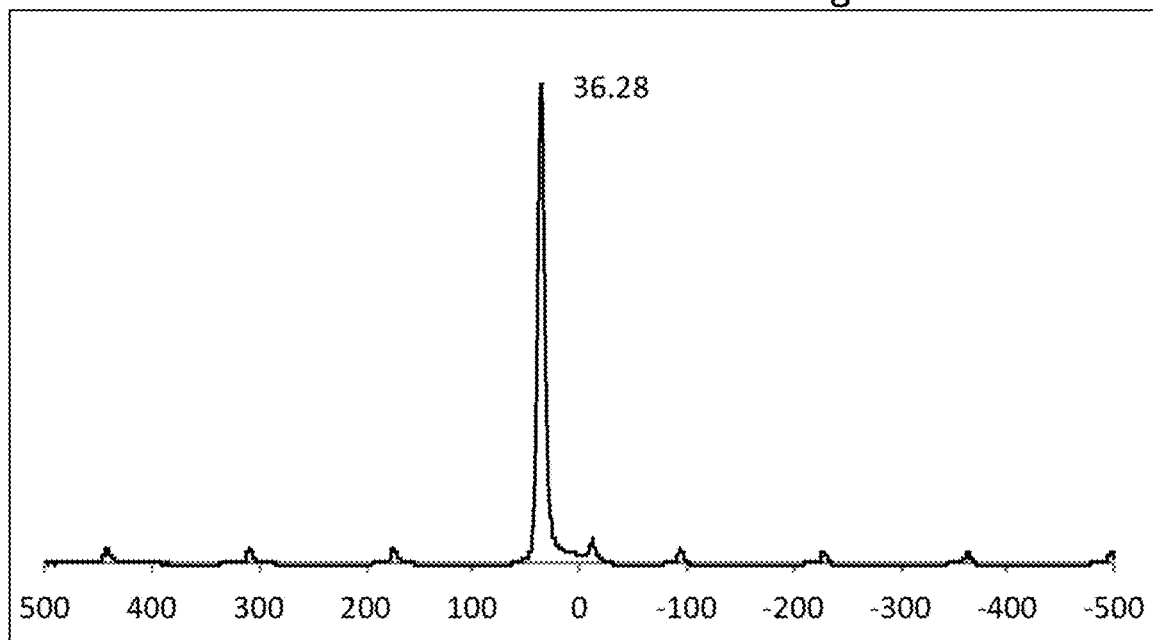
FIGS. 29A-29E are related to Example 7 and illustrate NMR spectra for SAPO-5 and HP SAPO-5.
Figure 29B:
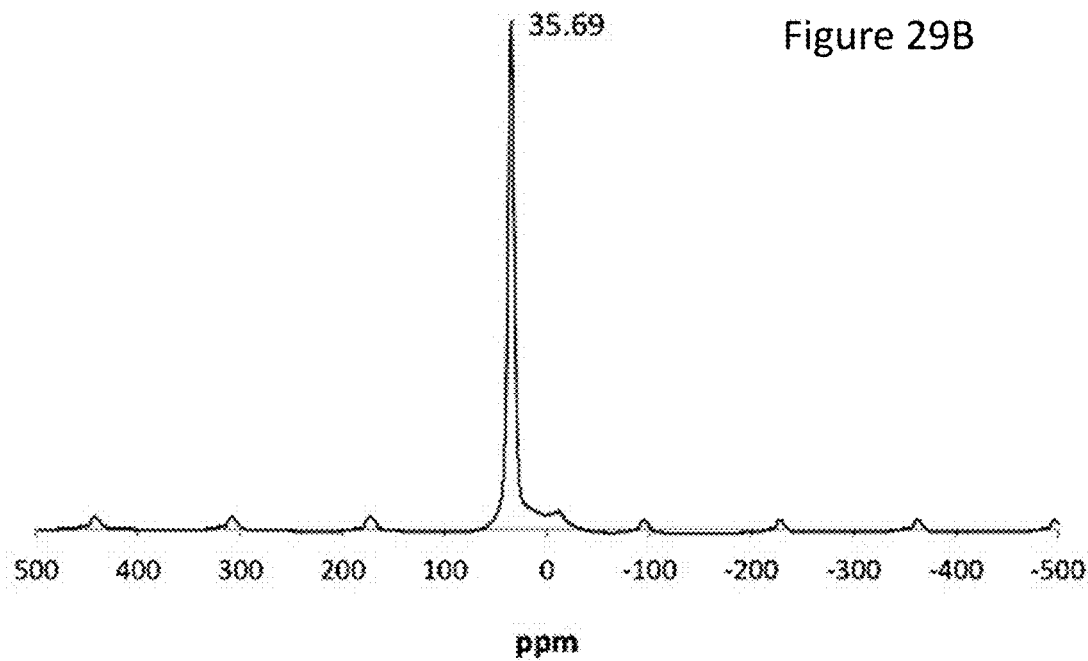

FIG. 29A illustrates the $^{27}Al$ MAS NMR spectra of SAPO-5. FIG. 29B illustrates the $^{27}Al$ MAS NMR spectra of HP SAPO-5. FIG. 30A illustrates the $^{27}Al$ MAS NMR spectra of SAPO-34. FIG. 30B illustrates the $^{27}Al$ MAS NMR spectra of HP SAPO-34.

Figure 29C:
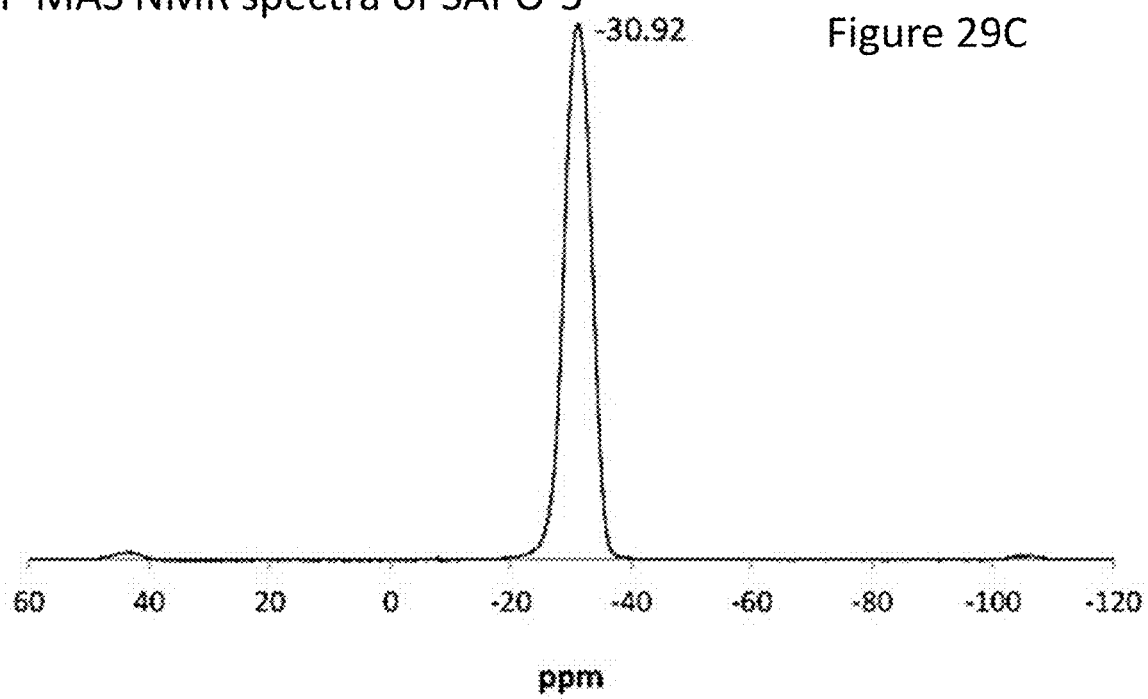
Figure 29D:
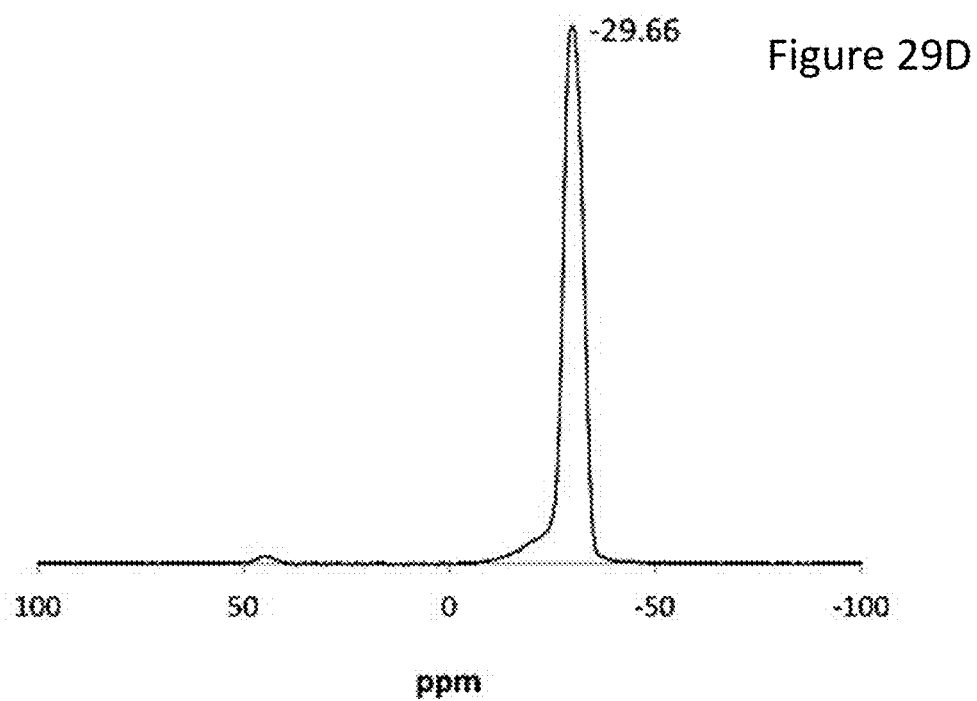
Figure 30C:
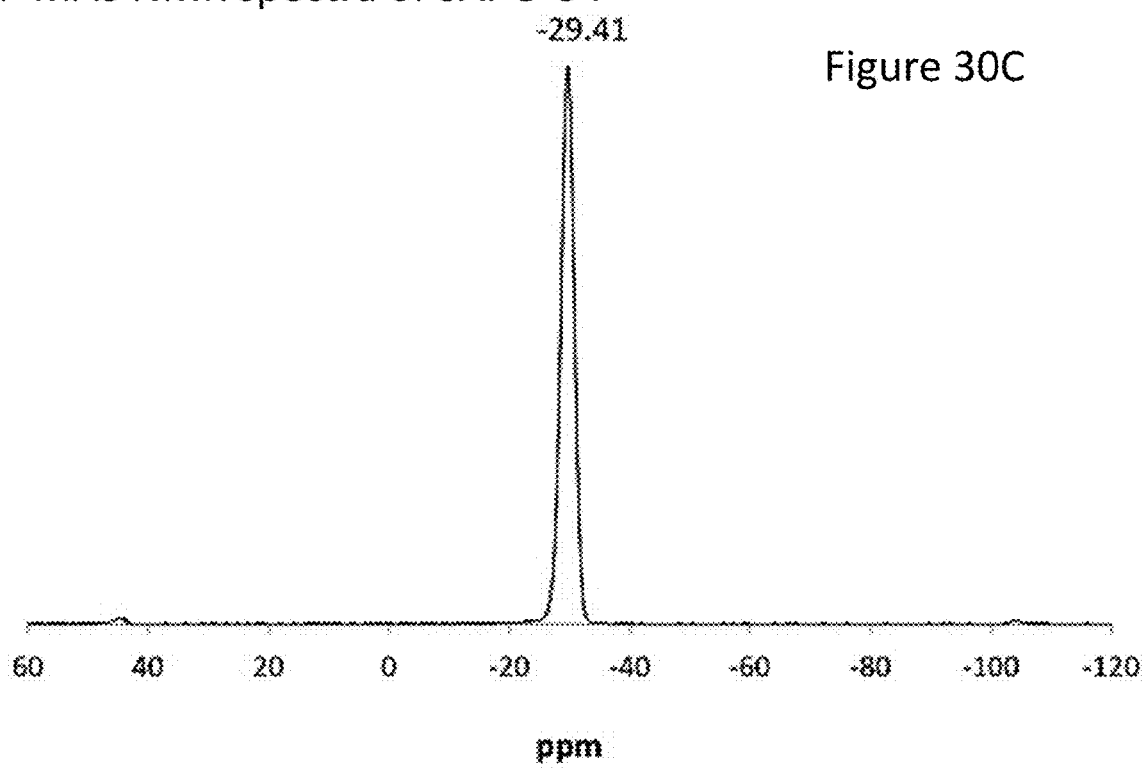
Figure 30D:
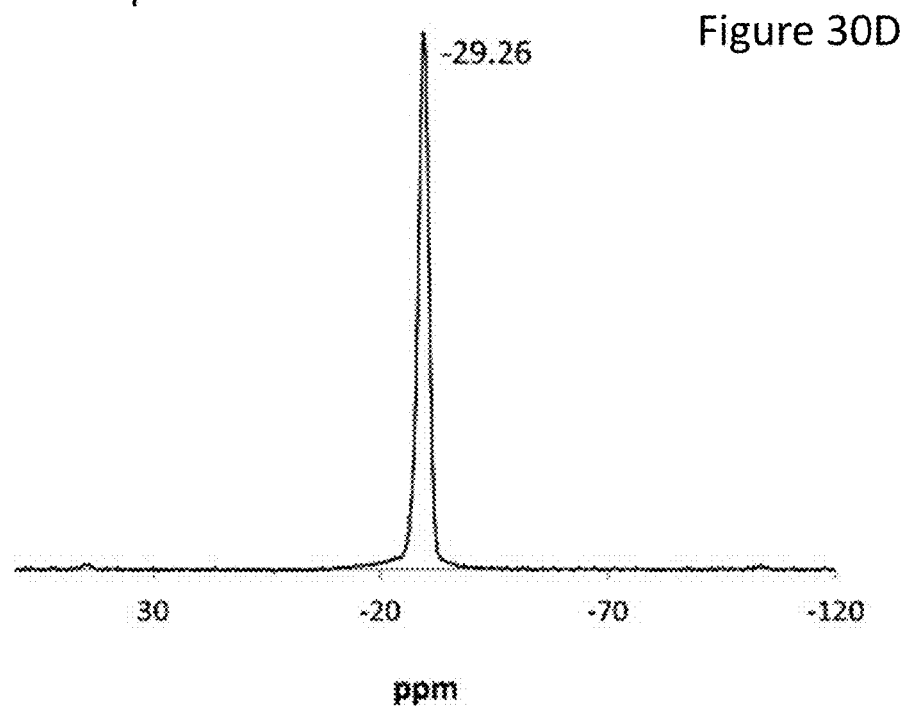

FIG. 29C illustrates the $^{31}P$ MAS NMR spectra of SAPO-5. FIG. 29D illustrates the $^{31}P$ MAS NMR spectra of HP SAPO-5. FIG. 30C illustrates the $^{31}P$ MAS NMR spectra of SAPO-34. FIG. 30D illustrates the $^{31}P$ MAS NMR spectra of HP SAPO-34.

The $^{27}Al$ and $^{31}P$ MAS NMR support the formation of a fully condensed crystalline AlPO framework. The $^{27}Al$ MAS/NMR has a strong signal at around −35 to −37 ppm indicating the presence of tetrahedral aluminium. Although there are weaker signals at around −16 and 8 ppm indicating the presence of hydrated aluminium centres which are octahedral and five coordinate respectively.

Figure 29E:
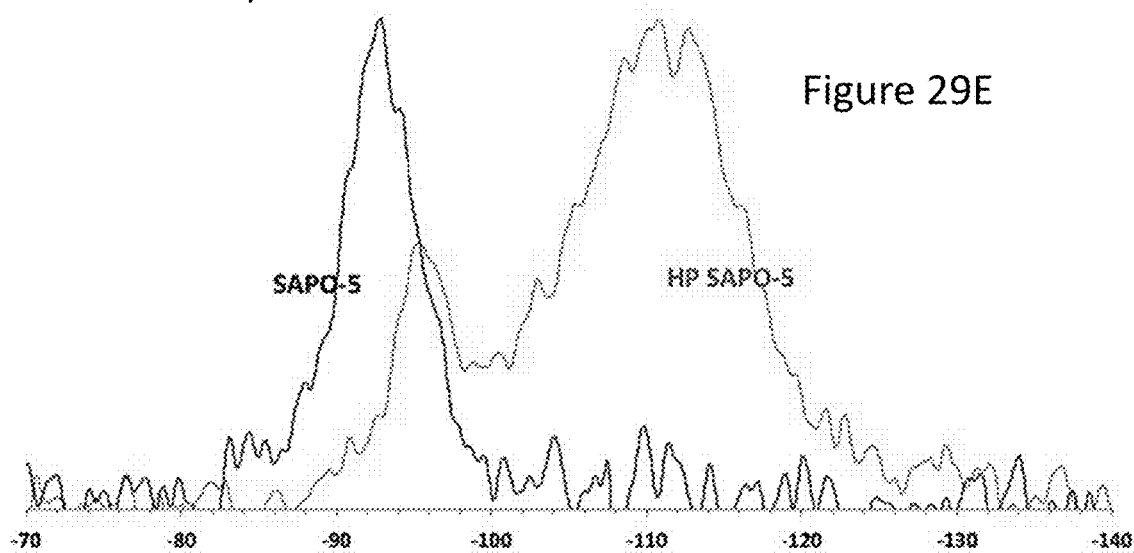

FIG. 29E illustrates the $^{29}Si$ MAS NMR spectra of SAPO-5 and HP SAPO-5. The spectra may suggest that the presence of the surfactant encourages the formation of silicon islands and results in silica nests, which are absent in the microporous system.

FIG. 30E illustrates the $^{29}Si$ MAS NMR spectra of SAPO-34 and HP SAPO-34. The Si NMR supports the formation of isolated silicon sites which are comparable to the microporous analogue.

Figure 31A:
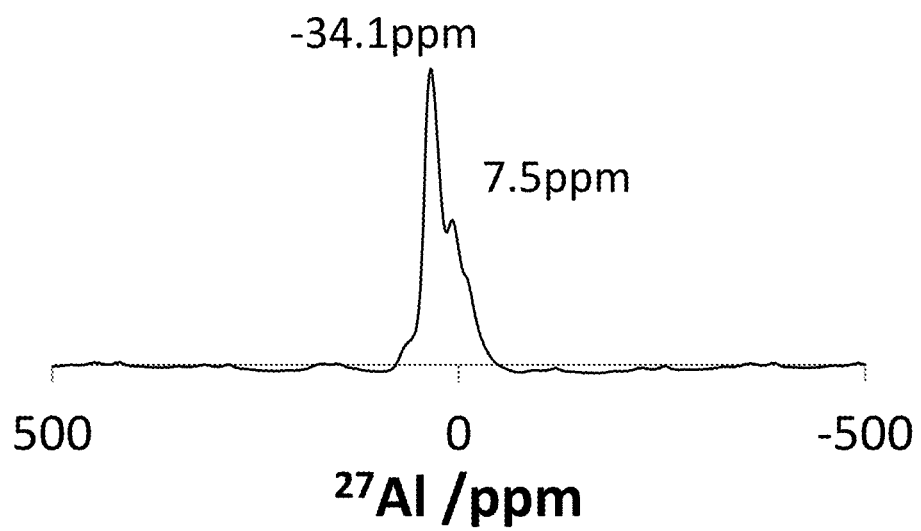
FIGS. 31A-31C are related to Example 7 and illustrate NMR spectra for HP SAPO-37.
Figure 31B:
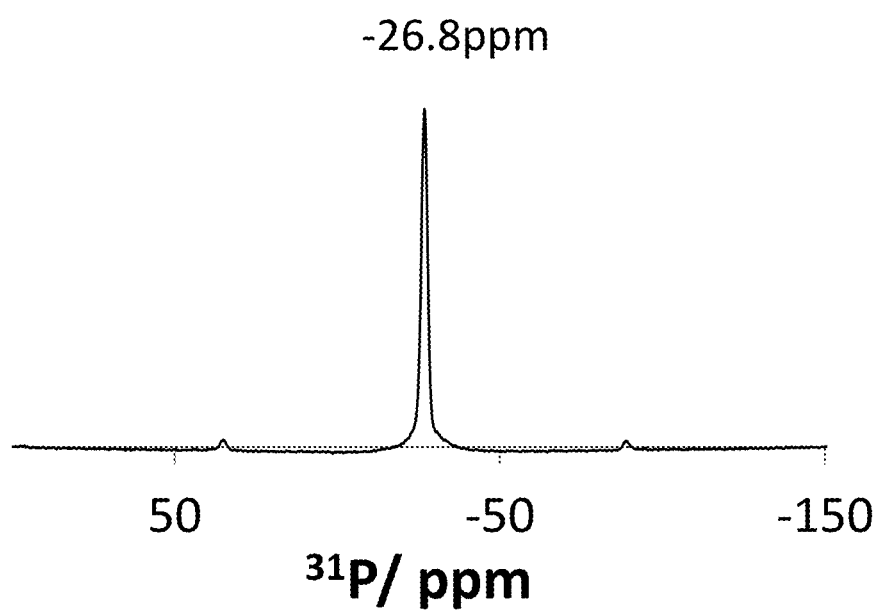
Figure 31C:
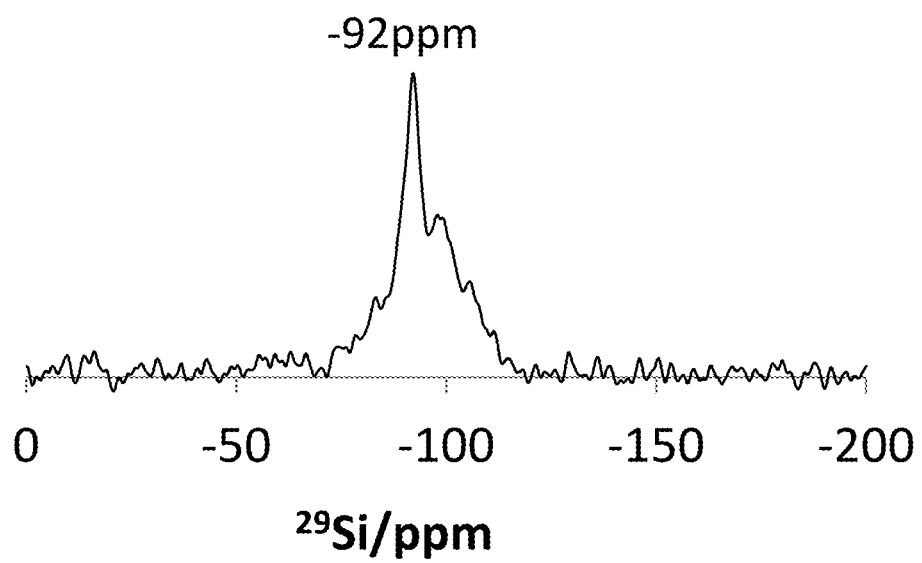

FIG. 31A illustrates the $^{27}Al$ MAS NMR spectra of HP SAPO-37. FIG. 31B illustrates the $^{31}P$ MAS NMR spectra of SAPO-37. FIG. 31C illustrates the $^{29}Si$ MAS NMR spectra of SAPO-37.

FT-IR, $NH_3$, CO and Collidine Probes

To further investigate the acidic properties of the resulting hierarchical catalysts FT-IR with probe molecules (CO and collidine) was used. FT-IR permitted direct observation of the hydroxyl region of the hierarchical SAPOs.

Figure 32A:
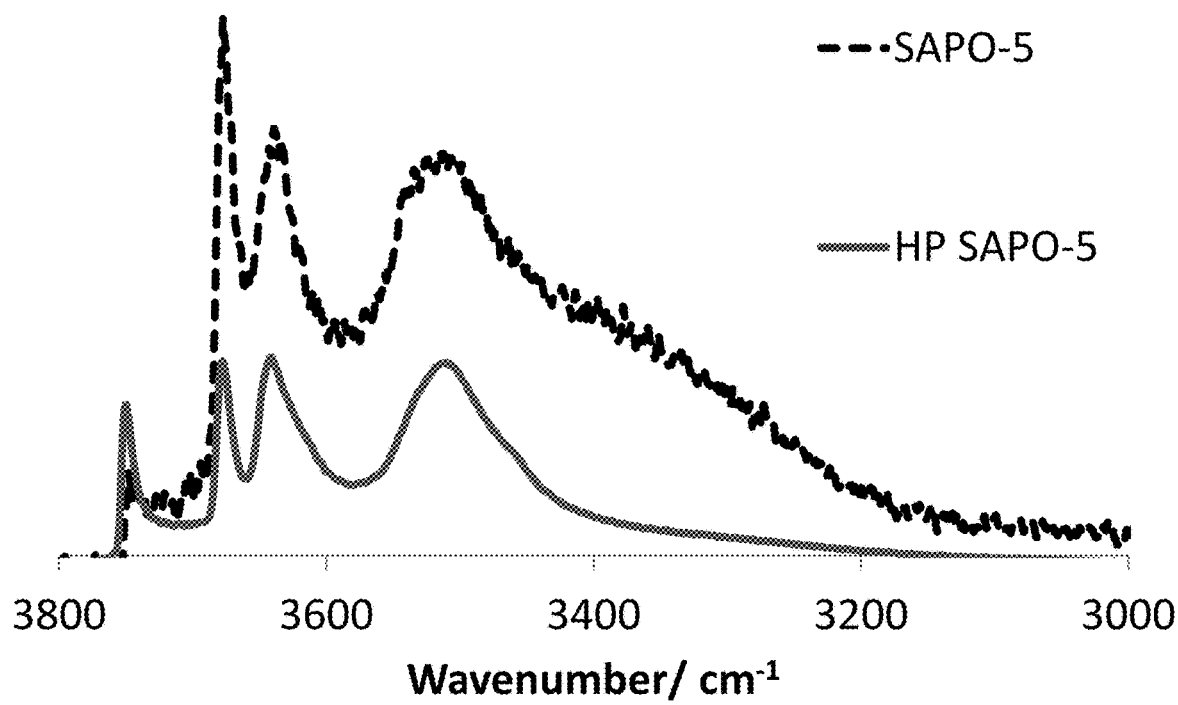
FIG. 32A is related to Example 7 and illustrates the FT-IR spectra of SAPO-5 and HP SAPO-5.
Figure 32B:
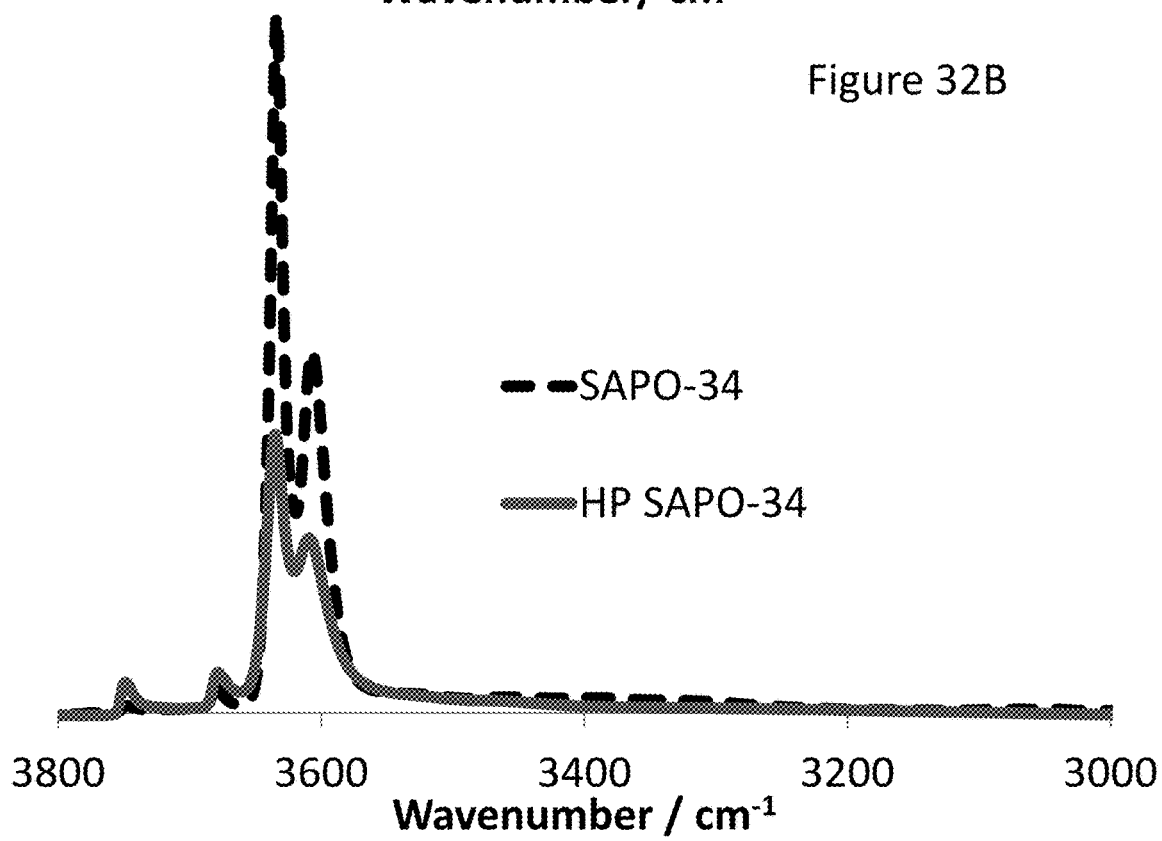
FIG. 32B is related to Example 7 and illustrates the FT-IR spectra of SAPO-34 and HP SAPO-34.

The FT-IR spectra of SAPO-5 and HP SAPO-5 are presented in FIG. 32A, and the FT-IR spectra of SAPO-34 and HP SAPO-34 are presented in FIG. 32B. Both catalysts had bands attributable to POH/AlOH (3678 cm$^{-1}$) defect sites and bands (3628-3600 cm$^{-1}$) arising from the substitution of silicon into the framework (Si—OH—Al). There was also an additional band at 3746 cm$^{-1}$ that were assigned to defect Si—OH groups which were marginal in the FT-IR of the microporous catalysts indicating that these silanol sites were formed via the calcination of the surfactant.

Figure 32C:
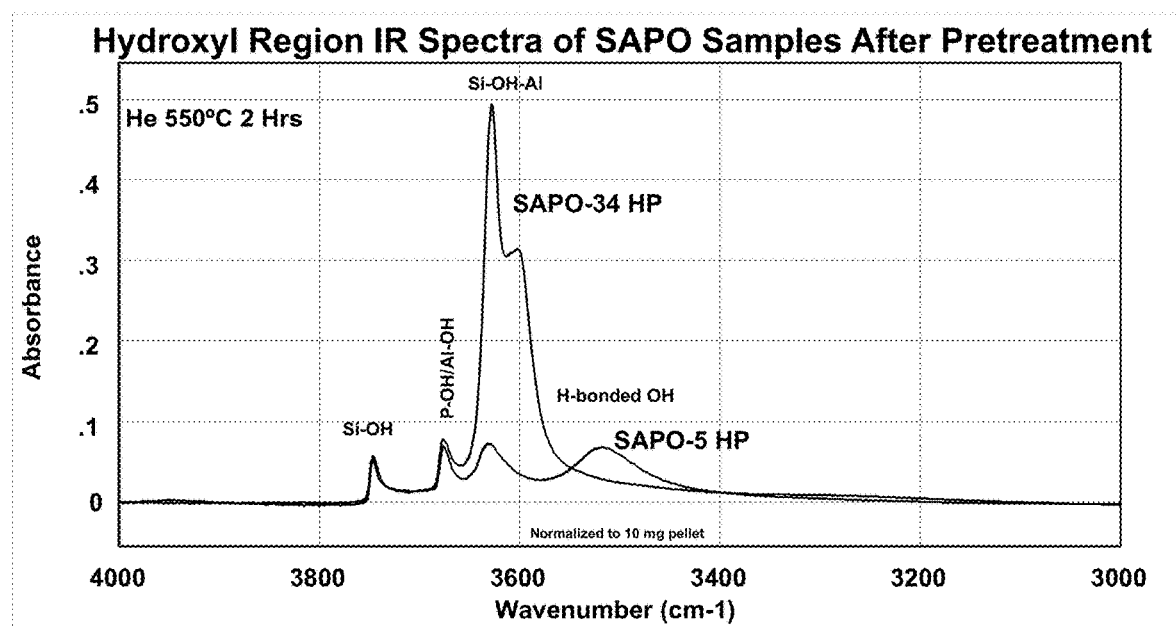
FIG. 32C is related to Example 7 and illustrates a comparison of the FT-IR spectra of HP SAPO-5 and HP SAPO-34.

A comparison of the FT-IR spectra for HP SAPO-5 and HP SAPO-34 is presented in FIG. 32C. As shown in FIG. 32C, the hierarchical porous materials share a common Si—OH peak (~3750 cm$^{-1}$) that is significantly greater than in the spectra of the corresponding microporous SAPO-5 and SAPO-34 (see FIGS. 32A and 32B).

Figure 33A:
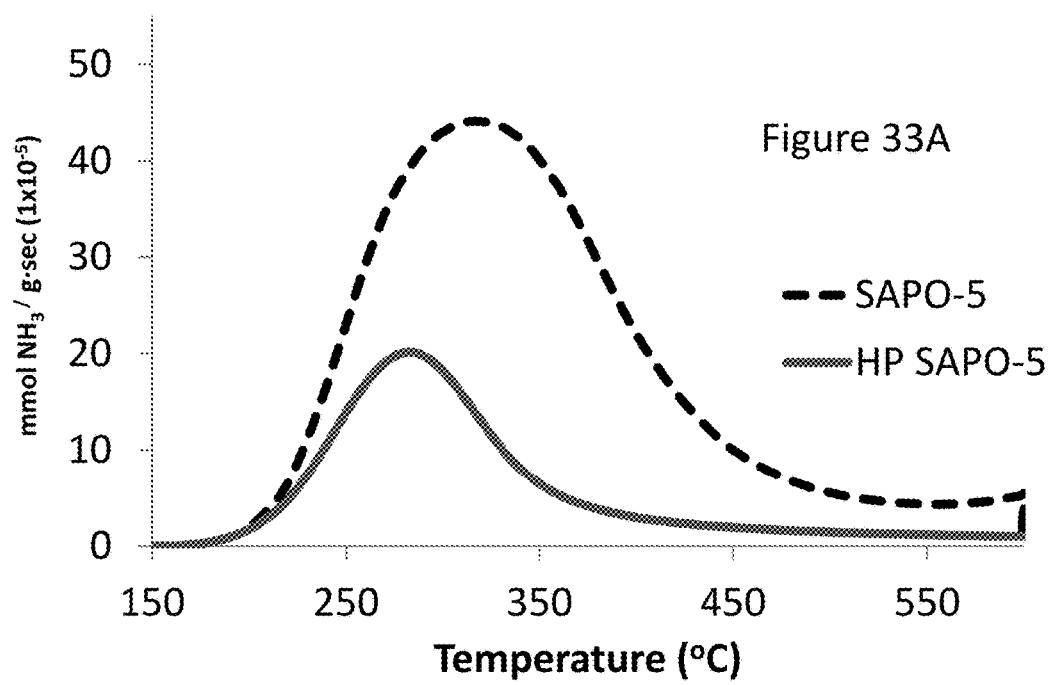
FIG. 33A is related to Example 7 and illustrates the TPD-NP$_3$ results of SAPO-5 and HP SAPO-5.
Figure 33B:
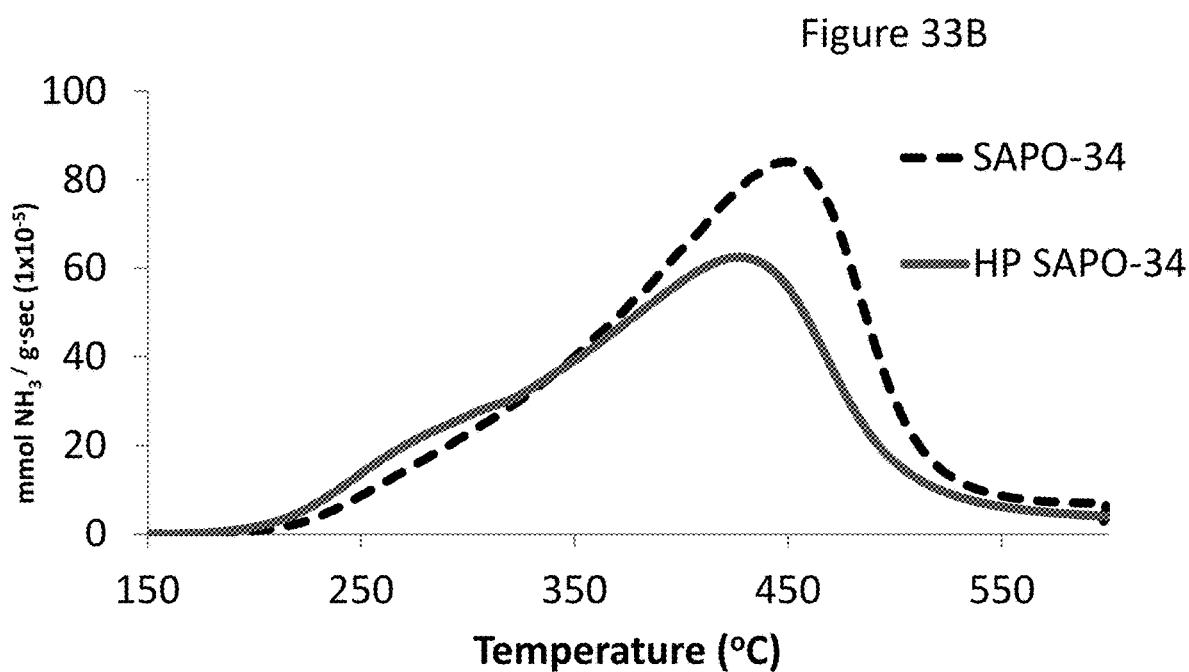
FIG. 33B is related to Example 7 and illustrates the TPD-NP$_3$ results of SAPO-34 and HP SAPO-34.
Figure 33C:
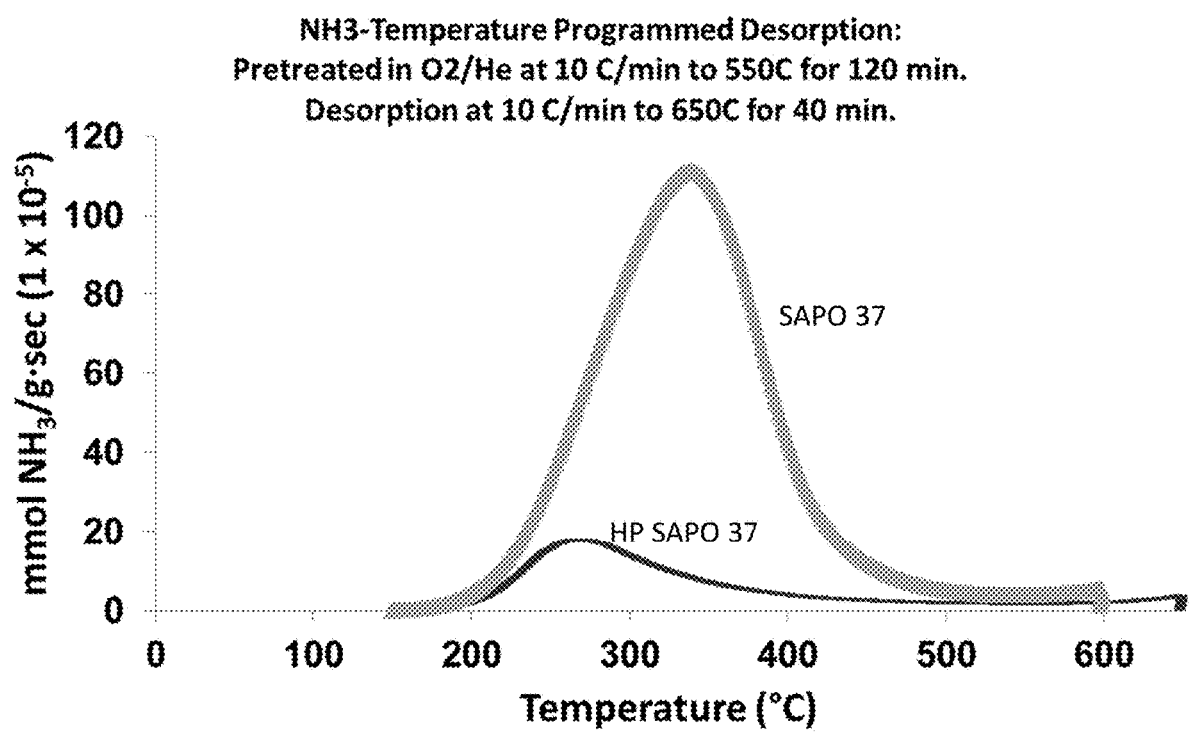
FIG. 33C is related to Example 7 and illustrates the TPD-NP$_3$ results of SAPO-37 and HP SAPO-37.

The quantity and strength of acid sites was investigated using a programmed temperature desorption of ammonia (TPD) for SAPO-5 and HP SAPO-5, the results of which are presented in FIG. 33A, for SAPO-34 and HP SAPO-34, the results of which are presented in FIG. 33B, and for SAPO-37 and HP SAPO-37, the results of which are presented in FIG. 33C.

All TPD measurements were performed on a custom built system using TCD detectors to monitor ammonia concentration. Samples were pre-treated by heating at 10° C./min to 550° C. in a 20% $C_2$/Helium mixture for 2 hours. The samples were exposed to ammonia and allowed to equilibrate at 150° C. for 8 hours. Desorption was performed in flowing at 10° C./min to 600° C. and held for 40 minutes at 600° C.

The results indicated similar acid strength between SAPO-5 and HP SAPO-5 (see FIG. 33A), between SAPO-34 and HP SAPO-34 (see FIG. 33B), and between SAPO-37 and HP SAPO-37 (see FIG. 33C). Without wishing to be held to any particular theory, it is believed that the slight additional feature in FIG. 33B at 250-300° C. may be attributable to the weakly acidic silanol sites and further allude to the presence of the SiOH sites in the hierarchical catalysts.

While the FT-IR spectra provided information about the types of hydroxyl groups present, it did not discriminate regarding the strength and type of acid sites present in the hierarchically porous materials. The acid strength of these materials is believed to be related to the ensuing catalytic properties of the materials. Without wishing to be held to any particular theory, the Beckmann rearrangement with solid acid catalysts is believed to rely on a subtle balance of acidity within the active site; it needs to be strong enough to permit the reaction to perform but weak enough to enable the basic lactam to desorb before over reacting, coke formation and deactivation.

Figure 34A:
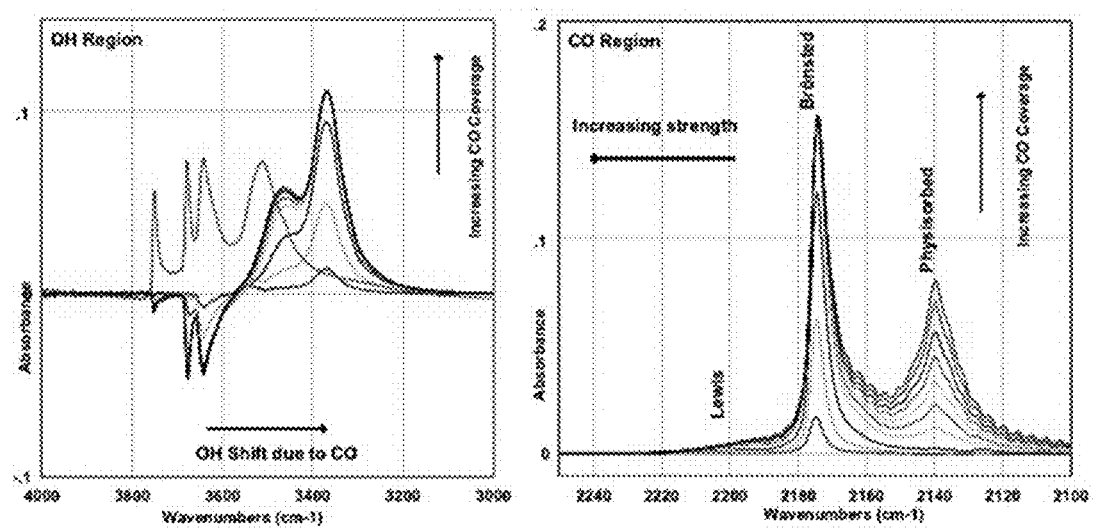
FIG. 34A is related to Example 7 and illustrates the CO adsorption results of HP SAPO-5.
Figure 34B:
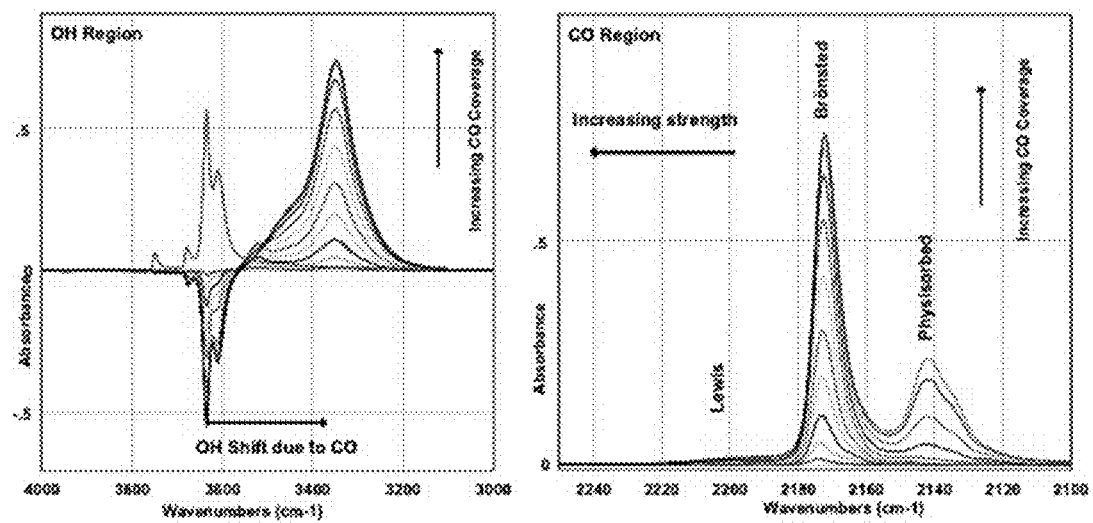
FIG. 34B is related to Example 7 and illustrates the CO adsorption results of HP SAPO-34.

Characterization of the strength of the acid sites was investigated using probe molecules such as CO and 2,4,6-trimethylpyridine (collidine) with the FT-IR to indirectly study the acidity of the material. The absence of absorption 2190 cm$^{-1}$ in FIGS. 34A and 34B indicates that no Lewis acidity was observed in either the HP SAPO-5 or the HP SAPO-34 materials, and that only Brønsted acid sites were present. Evaluation of the band shift of the Brønsted acid sites between 260 and 286 cm$^{-1}$ upon interaction with CO revealed that both samples primarily consisted of moderate strength Brønsted acid sites. By integrating the area of the Brønsted acid peaks it was possible to ascertain that the HP SAPO-34 has more total Brønsted acidity, as well as some stronger acid sites (larger peak shift) compared the HP SAPO-5 sample. These results were similar to the ammonia temperature programmed desorption results shown in FIGS. 33A and B, and the FT-IR collidine data shown in FIGS. 35A and 35B. The strength of acidity of the hierarchical catalysts was similar to the acid strength of microporous catalysts, indicating that the hierarchical porous material has similar active sites to those of the corresponding microporous materials.

FT-IR with CO demonstrated that in both HP SAPO-5 (see FIG. 34A) and HP SAPO-34 (see FIG. 34B) no Lewis acidity was observed, characterized by an absence of absorption 2190 cm$^{-1}$. Instead only Brønsted acid sites were present. Evaluation of the band shift of the Brønsted acid sites between 260-286 cm$^{-1}$ upon interaction with CO (Table 2) revealed that both samples primarily consisted of moderate strength Brønsted acid sites. Table 3 provides the position of maxima of OH Brønsted sites and their shifts ($\Delta v_{OH}$) upon CO Adsorption at 80K on HP SAPO-34, HP SAPO-5 and their microporous analogues.

TABLE 3

Position of Maxima of OH Brønsted sites

| Catalysts | | $v_{OH}$ (cm$^{-1}$) | $v_{OH...CO}$ (cm$^{-1}$) | $\Delta v_{OH}$ (cm$^{-1}$) |
|---|---|---|---|---|
| SAPO-5 | OHA | 3638 | 3368 | 270 |
| HP SAPO-5 | OHA | 3637 | 3369 | 268 |
| SAPO-34 | OHA | 3633 | 3347 | 286 |
| | OHB | 3610 | 3281 | 329 |
| HP SAPO-34 | OHA | 3633 | 3347 | 286 |
| | OHB | 3612 | 3281 | 331 |

By integrating the area of the Brønsted acid peaks it was possible to ascertain that the HP SAPO-34 has more total Brønsted acidity, as well as some stronger acid sites (larger peak shift) compared the HP SAPO-5 sample. This trend was in good agreement with the ammonia temperature programme desorption results (FIGS. 33A and 33B). The results in Table 3 further indicated that the hierarchical catalysts have active sites that are similar to those in the corresponding microporous catalysts.

In order to further explore the acid sites within the hierarchical SAPOs, collidine was used as a probe with FT-IR. Collidine was chosen for three key reasons: i) It is a sterically demanding probe and therefore provides insight into the accessibility of the acidic sites, ii) It can assess the strength of interaction between the OH . . . N, by quantifying the bands at 1652 cm$^{-1}$ and 1637 cm$^{-1}$, hence allude to the strength of interaction between the substrates in the Beckmann rearrangement and finally iii) It is stable at high temperatures and therefore the strength of interaction can be screened over temperatures typical of the reaction conditions.

Figure 35A:
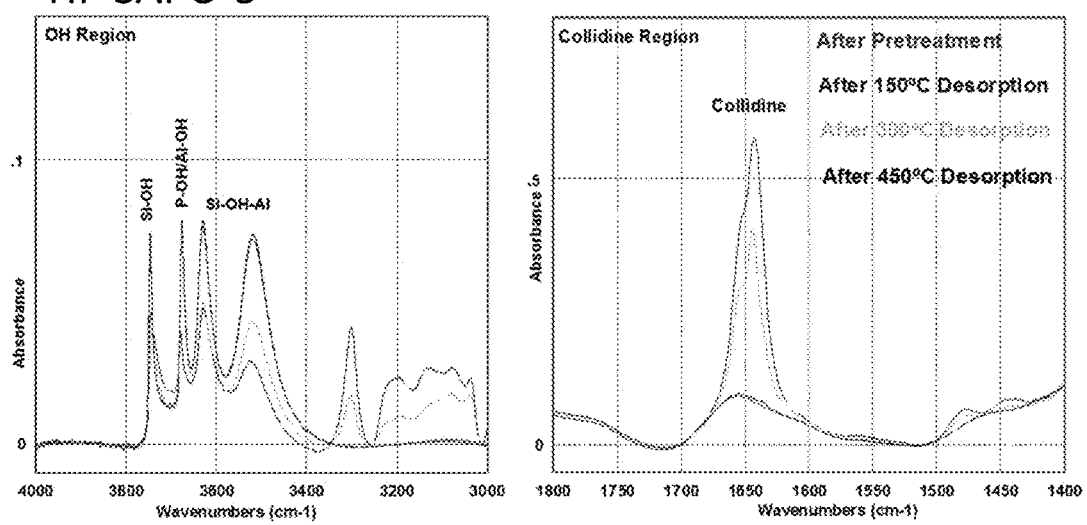
FIG. 35A is related to Example 7 and illustrates the collidine adsorption results of HP SAPO-5.
Figure 35B:
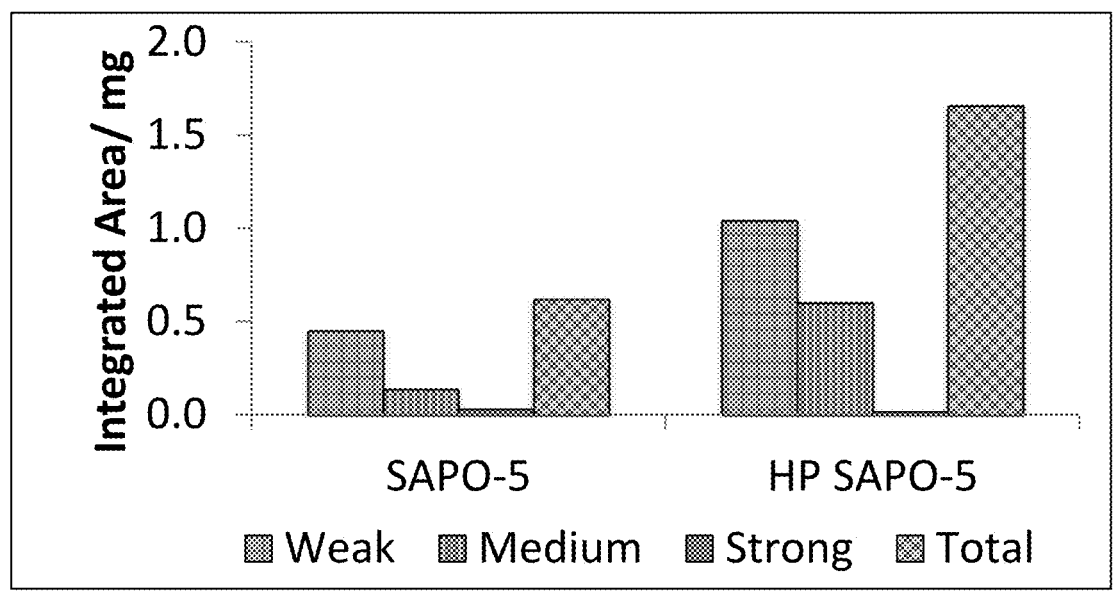
FIG. 35B is related to Example 7 and compares the distribution of acid sites in the SAPO-5 and HP SAPO-5 materials.

FIG. 35A illustrates the results of the collidine adsorption on HP SAPO-5. The collidine interacts with all of the OH group types after 150° C. desorption. Essentially all the collidine is desorbed by 450° C. FIG. 35B illustrates the distribution of weak, medium, and strong acid sites in the SAPO-5 and HP SAPO-5 catalysts. As shown in FIG. 35B, the HP SAPO-5 catalyst generally contains a greater number of weak, medium, and total acid sites than the SAPO-5 catalyst. In the case of the HP SAPO-5 the collidine is able to interact with all the OH group types (Si—OH, P—OH, Si—OH—Al and the H-bonded) after 150° C. desorption and their accessibility is greatly enhanced in comparison to the microporous analog SAPO-5.

FIG. 36A illustrates the results of the collidine adsorption on HP SAPO-34. The collidine interacts primarily with the Si—OH and P—OH groups after 150° C. desorption. FIG. 36B illustrates the distribution of weak, medium, and strong acid sites in the SAPO-34 and HP SAPO-34 catalysts. As shown in FIG. 36B, the HP SAPO-34 catalyst has a similar distribution of acid sites compared to the SAPO-5 catalyst. As shown in FIG. 36A, similar to the microporous structure only a small fraction of the bridging OH groups are accessible to collidine as there is very minimal attenuation of the bridging hydroxy groups.

The differences between the accessibility of the two hierarchical catalysts active sites could be explained by their very different microporous structures (see FIGS. 4A and 4B). SAPO-5 has much larger pores, 7.3 Å, than SAPO-34, 3.8 Å. As the hierarchical materials are largely microporous, it is likely that not all the mesopores are accessible owing to them being surrounded by the microporous system, and therefore the FT-IR-collidine may not truly represent all the types of acid sites that are present. In both cases all the collidine is desorbed by 450° C. Similar to the FT-IR-CO results, the collidine adsorption indicates that the collidine largely adsorbs onto moderate to weak acid sites.

The hierarchical catalysts, such as HP SAPO-5 and HP SAPO-34, had comparable acidity to their corresponding microporous analogues, but provided improvements in one or more of lifetime, activity and substrate versatility in the Beckmann rearrangement, whilst not compromising selectivity. Without wishing to be held to any particular theory, it is believed that the inclusion of the mesopores has resulted in increased access of the substrates to the active sites, as well as the formation of additional active sites (silanols) that may participate in the reaction.

Example 8: Synthesis and Characterization of Additional Hierarchical Porous AlPO Catalysts Aluminum isopropoxide (6.807 g, Aldrich) was added to a Teflon beaker with phosphoric acid (2.28 ml, 85% in $H_2O$, Aldrich) and water (10 ml) and vigorously stirred for 1.5 hours until a homogeneous solution was formed. dimethyloctadecyl[(3-(trimethoxysilyl)propyl]ammonium chloride (DMOD) (1.2 ml, 72% in $H_2O$, Aldrich) was added drop wise, followed immediately by the addition of triethylamine (3.7 ml, Aldrich) drop wise and then water (20 ml). The resulting thicker solution was stirred for one hour. The metal precursors as shown in Table 4 were added drop wise and the gel was stirred for a further 1.5 hours.

A microporous analog was formed using the same method, but without the inclusion of the DMOD.

TABLE 4

Gel composition

| Catalyst | Gel Composition (wt. %) |
| --- | --- |
| HP Co AlPO-5 | 1Al:1.3P:0.8SDA:0.1DMOD:50$H_2O$:0.03Co |
| HP Ti AlPO-5 | 1Al:1.3P:0.8SDA:0.1DMOD:50$H_2O$:0.03Ti |
| HP Co Ti AlPO-5 | 1Al:1.3P:0.8SDA:0.1DMOD:50$H_2O$:0.03Co:0.03Ti |

The contents of the gel were divided between three 23 ml Teflon-lined stainless-steel autoclaves that were transferred to a pre heated fan assisted oven (WF-30 Lenton) at 200° C. for 24 hours. The solid product from each autoclave was collected via filtration and washed with 500 ml of deionized water. The product was left to dry at 80° C. overnight. The as-synthesized catalyst was calcined in a tube furnace under a flow of air at 550° C. for 16 hours to produce a white solid.

The effect of different metal combinations within the multi-metallic hierarchically porous (HP) catalysts was investigated using an array of spectroscopic techniques. All the multi-metallic HP catalysts were synthesized using the same soft-templating technique, which employed the organosilane surfactant, dimethyloctadecyl[(3-(trimethyoxysilyl)propyl]ammonium chloride (DMOD) to direct the formation of the mesopores and triethylamine to direct the formation of the micropores. DMOD was chosen as an appropriate surfactant owing to its silicon containing hydrophilic head and the high propensity for Si—O—Si and Si—O—Al bonds to form, therefore promoting the formation of mesopores throughout the AlPO framework. In order to assess the impact of different metal combinations on the intrinsic nature of the active site identical synthesis procedure was used for the catalysts. The catalysts will contain silicon in the framework too due to the nature of the synthesis.

Figure 37:
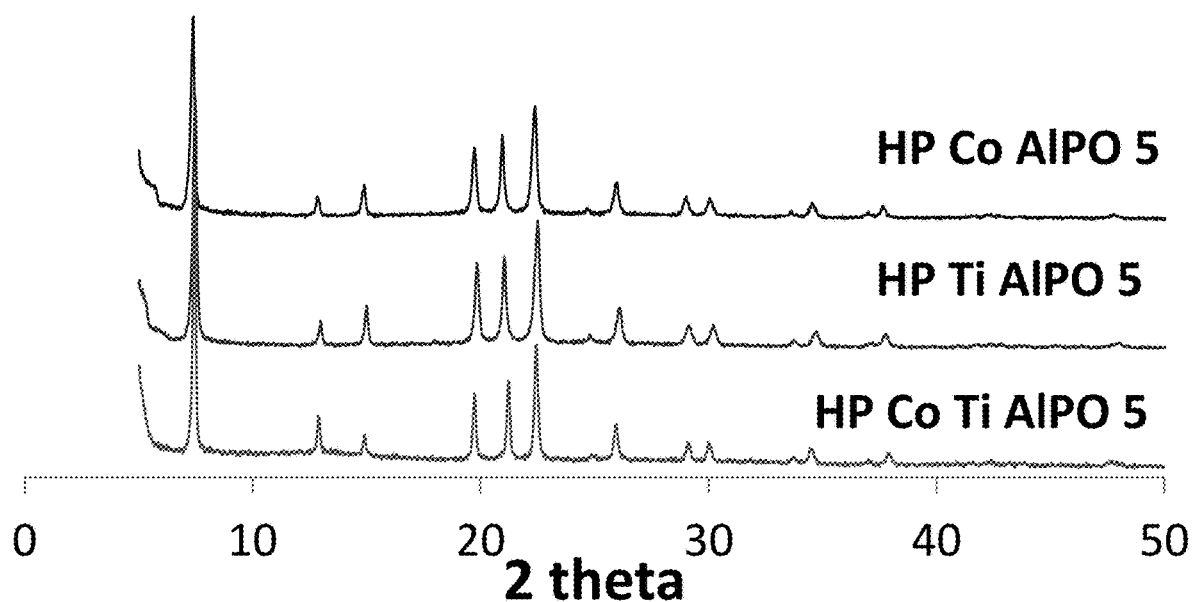
FIG. 37 is related to Example 8 and illustrates the powder X-ray diffraction spectra for HP Co AlPO-5, HP Ti AlPO-5, and HP Co Ti AlPO-5.

As shown in the powder X-ray diffraction patterns illustrated in FIG. 37, the various metal combinations, cobalt, titanium as well as cobalt and titanium, within the HP AlPO-5 framework did not result in any structural or phase imperfects and the intended crystalline AFI framework was yielded.

Figures 38A, 38B, 38C:
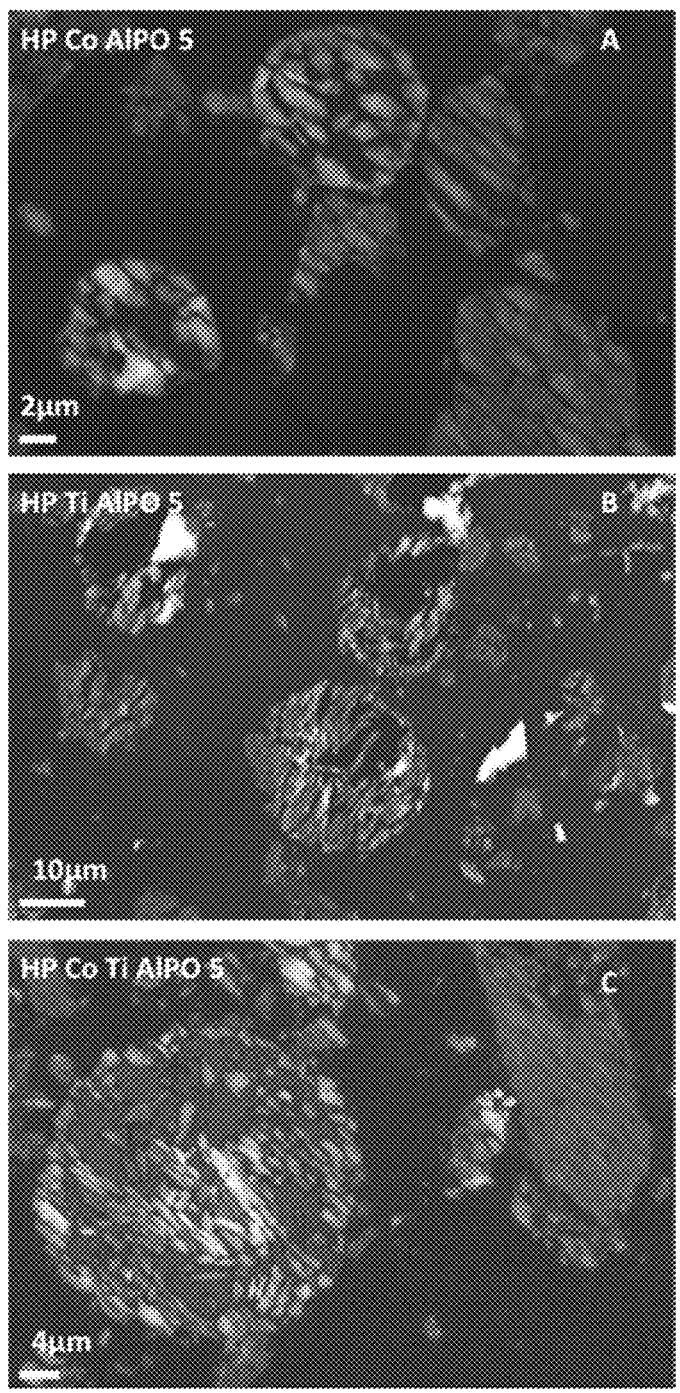
FIG. 38A is related to Example 8 and illustrates an SEM image of HP Co AlPO-5.
FIG. 38B is related to Example 8 and illustrates an SEM image of HP Ti AlPO-5.
FIG. 38C is related to Example 8 and illustrates an SEM image of HP Co Ti AlPO-5.

FIG. 38A is an SEM image of HP Co AlPO-5, FIG. 38B is an SEM image of HP Ti AlPO-5, and FIG. 38C is an SEM image of HP Co Ti AlPO-5. As shown in FIGS. 38A-38C, scanning electron microscopy revealed the expected spherical AlPO-5 particles I the region of 5-30 microns further substantiating the successful synthesis of the AlPO-5 framework.

Figure 39A:
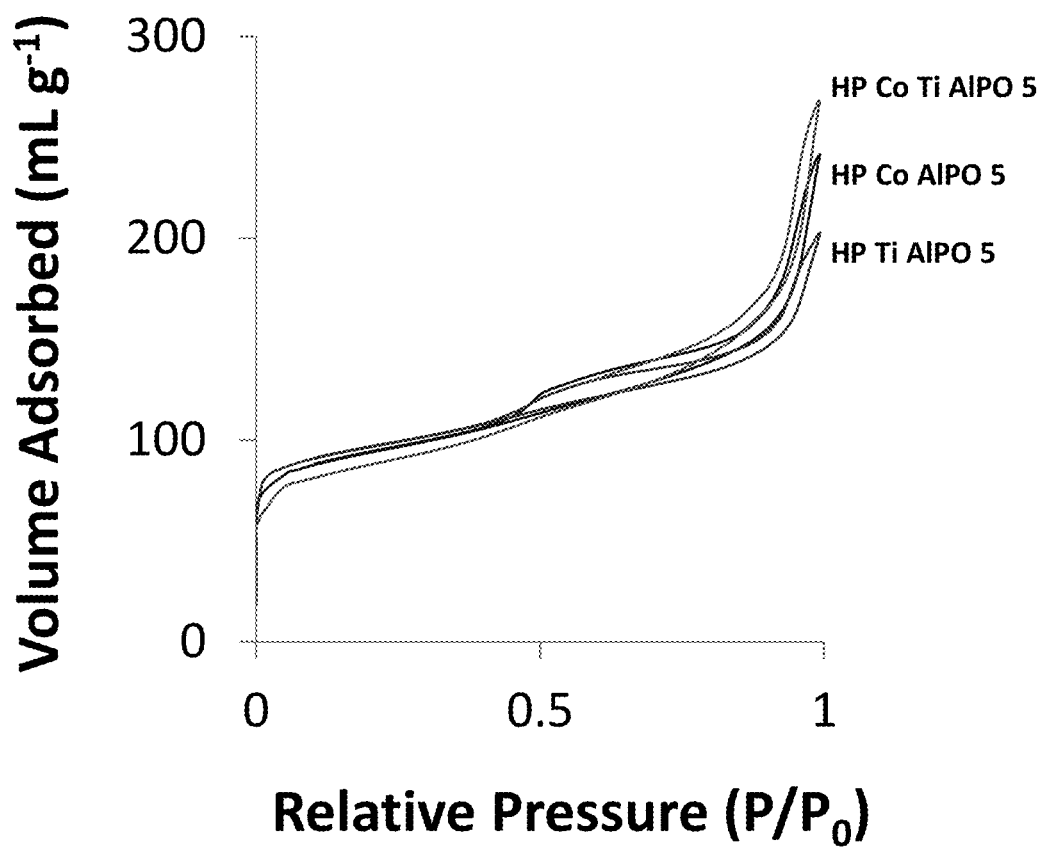
FIG. 39A is related to Example 8 and illustrates the nitrogen adsorption isotherm for HP Co AlPO-5, HP Ti AlPO-5, and HP Co Ti AlPO-5.
Figure 39B:
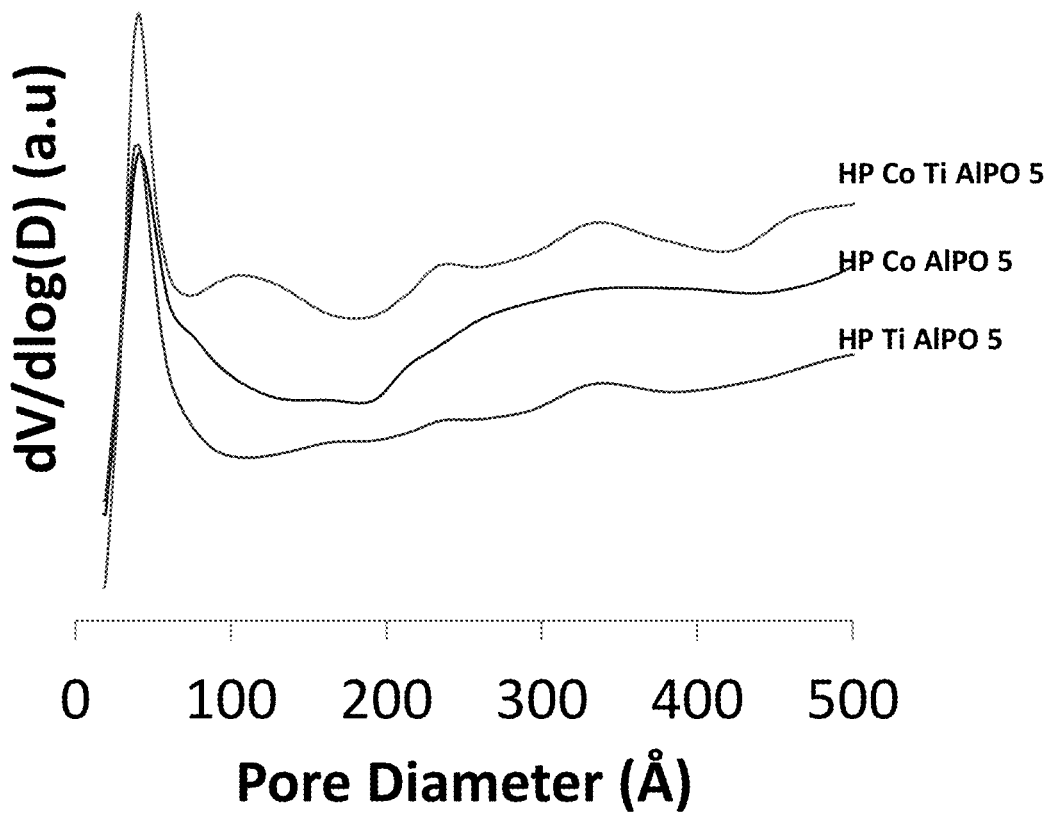
FIG. 39B is related to Example 8 and illustrates the BJH pore distribution curves for HP Co AlPO-5, HP Ti AlPO-5, and HP Co Ti AlPO-5.

BET measurements were performed to assess the efficacy of our design strategy in the generation of hierarchically porous catalysts. FIG. 39A illustrates the nitrogen adsorption isotherm for each catalyst. FIG. 39B illustrates the BJH pore distribution curves for each catalyst. All the hierarchically porous samples exhibited a type IV isotherm, indicating the presence of mesopores within the catalyst.

TABLE 5

BET measurements for microporous and HP $M^{II}M^{III}$ AlPO-5 catalysts

| Catalyst | BET Surface Area (m$^2$/g) | Mesopore and External Surface area (m2/g) | Micropore volume (cm$^3$/g) | Mesopore volume (cm$^3$/g) |
| --- | --- | --- | --- | --- |
| Co AlPO-5 | 192.2 | 30.3 | 0.08 | 0.11 |
| Ti AlPO-5 | 200.7 | 22.7 | 0.09 | 0.05 |
| Co Ti AlPO-5 | 165.6 | 43.7 | 0.06 | 0.08 |
| HP Co AlPO-5 | 306.2 | 111.8 | 0.08 | 0.30 |
| HP Ti AlPO-5 | 312.2 | 106.3 | 0.09 | 0.23 |
| HP Co Ti AlPO-5 | 288.8 | 115.56 | 0.07 | 0.35 |

The BJH adsorption pore distribution curves further demonstrated that all the HP catalysts contained mesopores that are approximately 40 Å in diameter. As shown in Table 5, all the HP catalysts had larger total surface areas and mesopore volumes than their microporous analogues, whilst still retaining similar microporous surface areas and micropore volumes. The BET data strongly indicates the successful incorporation of mesopores into the hierarchically porous frameworks.

Figure 40A:
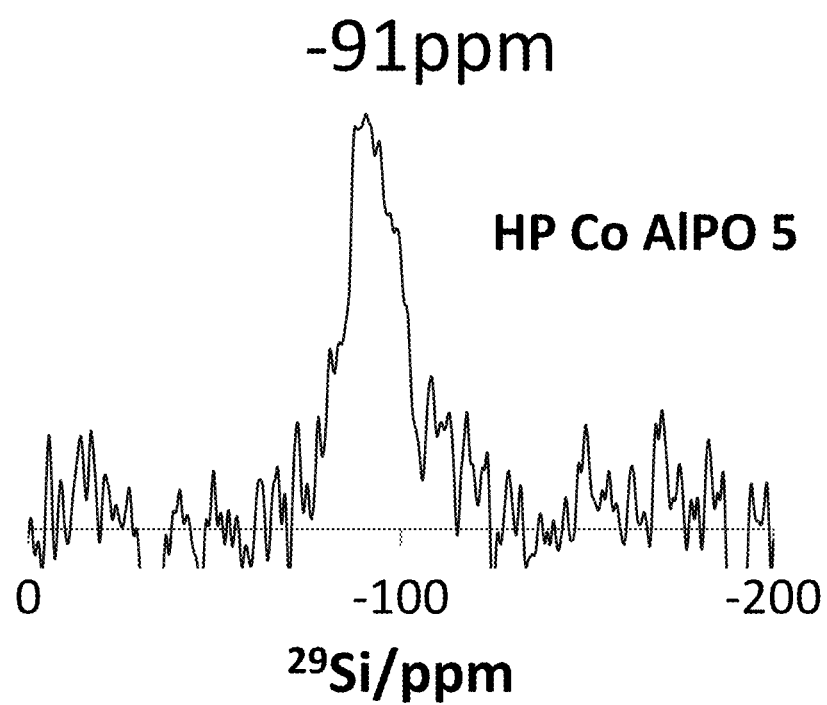
FIG. 40A is related to Example 8 and illustrates the $^{29}$Si MAS NMR of HP Co AlPO-5.
Figure 40B:
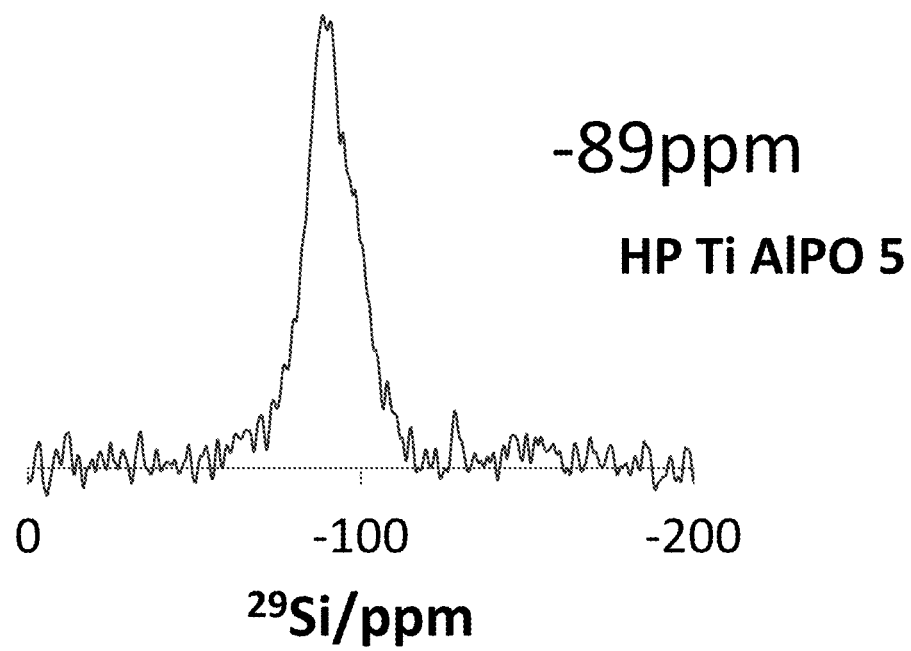
FIG. 40B is related to Example 8 and illustrates the $^{29}$Si MAS NMR of HP Ti AlPO-5.
Figure 40C:
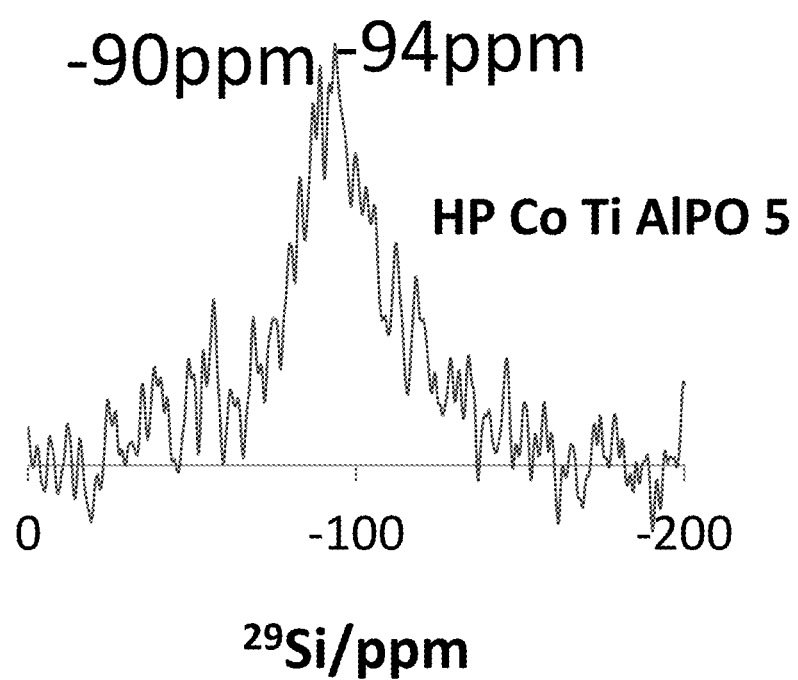
FIG. 40C is related to Example 8 and illustrates the $^{29}$Si MAS NMR of HP Co Ti AlPO-5.

In order to investigate the local coordination geometry of the Al(III), P(V) and Si(IV) sites MAS NMR was deployed. FIG. 40A illustrates the $^{29}$Si MAS NMR of HP Co AlPO-5. FIG. 40B illustrates the $^{29}$Si MAS NMR of HP Ti AlPO-5. FIG. 40C illustrates the $^{29}$Si MAS NMR of HP Co Ti AlPO-5. The $^{29}$Si MAS NMR of the three hierarchically porous catalysts further confirmed the incorporation of the silicon into the framework due to the utilization of the organosilane in the synthesis procedure. The signals in the $^{29}$Si MAS NMR is broad for all three of the HP catalysts, which indicates that there is an element of silicon zoning, which would be expected due nature of the synthesis. Although the main peak observed for the HP catalysts was at about −90 ppm, this is often assigned to isolated acidic Si(OAl)$_4$ sites which are isolated sites formed via type II substitution. This is actually unusual for Si AlPO-5 frameworks; typically one would expect a much broader signal with a lower ppm near to −100 ppm.[7] Therefore this is very interesting catalytically and synthetically as the HP catalysts represent a way as to generate isolated silicon sites within an AFI aluminophosphates framework that are otherwise difficult to form.

Figure 41:
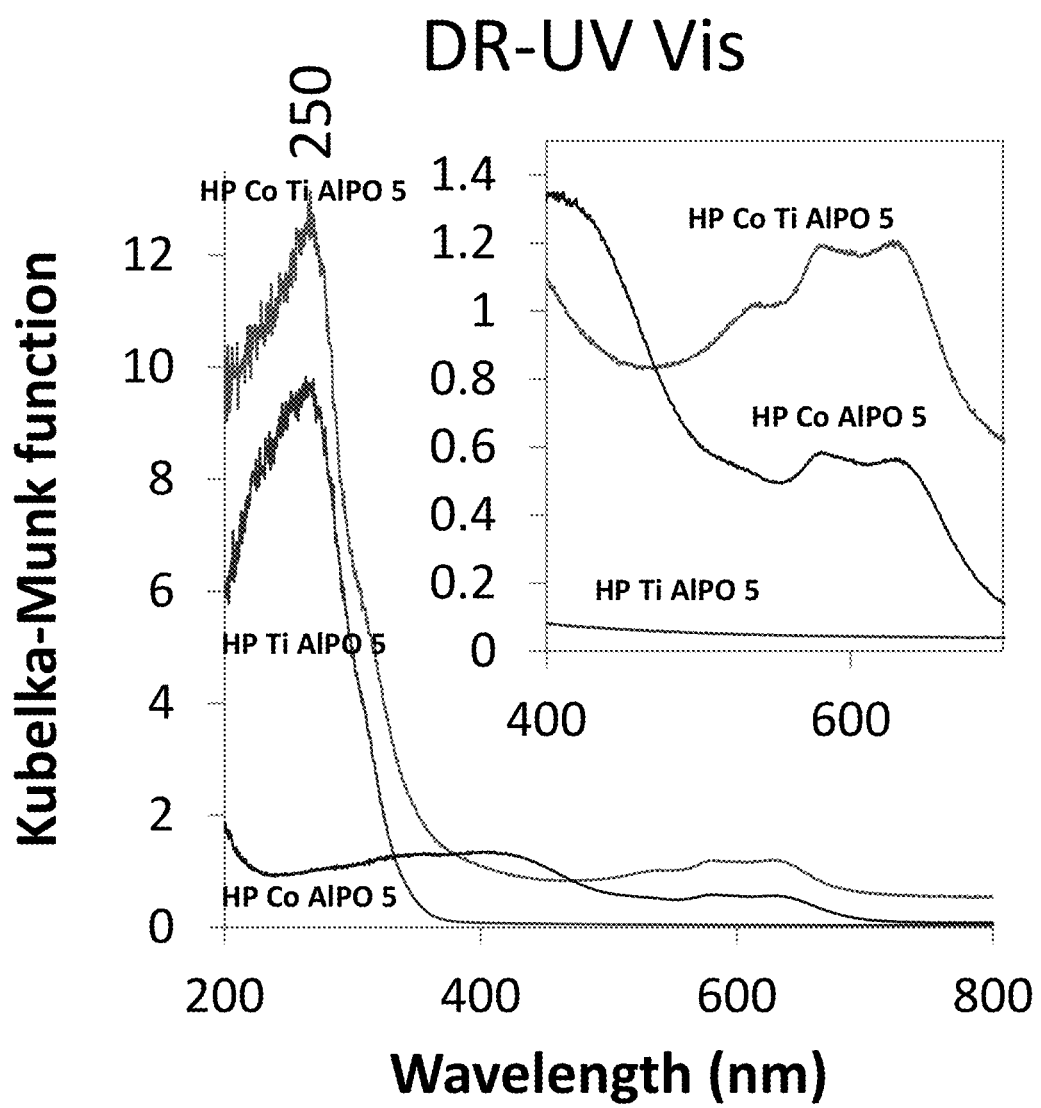
FIG. 41 is related to Example 8 and illustrates the DR UV/vis spectra of the HP Co AlPO-5, HP Ti AlPO-5, and HP Co Ti AlPO-5.

To elucidate the nature of the cobalt and titanium metallic sites in the substituted HP AlPO-5 catalysts diffuse reflectance (DR) UV/vis was employed. FIG. 41 illustrates the DR UV/vis spectra of the HP Co AlPO-5, HP Ti AlPO-5, and HP Co Ti AlPO-5. Diffuse reflectance UV Vis measurements enabled the molecular environments of the substituted cobalt and titanium ions within the AlPO framework to be investigated. The DR UV/vis of the reduced cobalt containing HP AlPOs have triplet bands in the visible region between 500 and 700 nm which can be attributed to the d-d transitions of Co(II) ions in tetrahedral coordination. The DR UV-Vis spectrum of reduced HP Co Ti ALPO-5 and HP Ti AlPO-5 show one strong absorption band in the 200-250 nm range due to tetrahedral Ti(IV) LMCT transitions with the framework oxygen ligands. The broad nature of this band indicates that the titanium isn't purely tetrahedral. Rather, the titanium centres are likely to be a mix between the tetrahedral and octahedral Ti (IV) sites this is often commonly seen within titanium substituted AlPOs. Although it should be noted that the Ti(IV) band in the HP Co Ti AlPO-5 is sharper than in HP Ti AlPO-5, indicating that the Ti (IV) ions are more tetrahedral in nature in the cobalt containing catalyst. This phenomenon can be attributed to 'support synergy' in which a second metal can help direct the titanium into the framework and has been observed in the microporous analogues previously.

Figure 42:
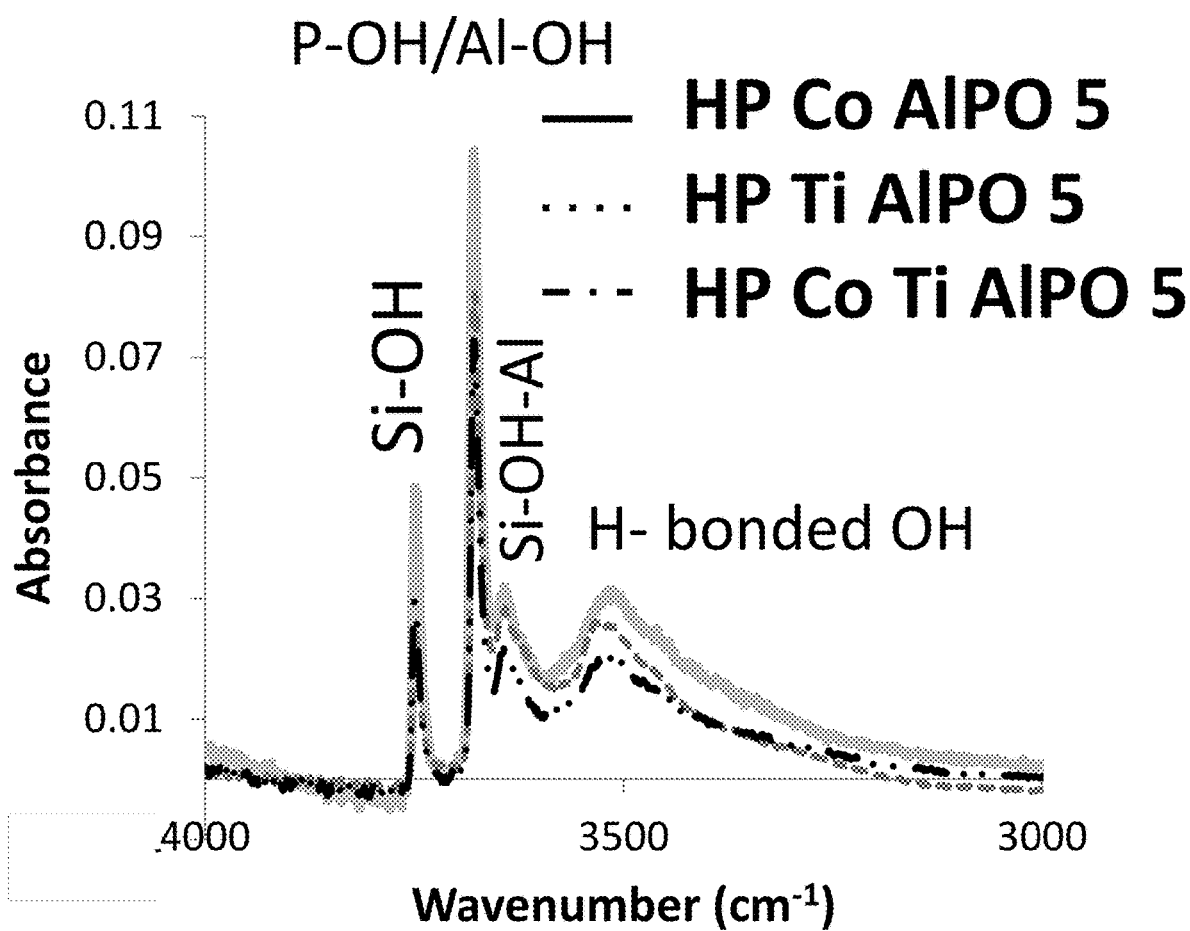
FIG. 42 is related to Example 8 and illustrates the FTIR spectra of the OH-stretching region for HP Co AlPO-5, HP Ti AlPO-5, and HP Co Ti AlPO-5.

The isomorphous substitution of Co(II) via type I substitution and Ti(IV) via type II substitution will both lead to an acid site being generated as will the incorporation of the Si(IV), and the strength, type and quantity of these sites will be intimately related to the catalysts activity. Therefore FT-IR was utilised to probe the acidity of the hierarchically porous frameworks further, as provided in FIG. 42. FIG. 42 illustrates the FTIR spectra of the OH-stretching region for HP Co AlPO-5, HP Ti AlPO-5, and HP Co Ti AlPO-5. Direct observation of the O—H stretching region indicated that the spectra was very similar for all three of the catalysts. Each contained bands due to Al—OH and P—OH defects as well as bands owing to silicon incorporation into the AlPO framework. There was a band at about 3640 cm$^{-1}$ in all three hierarchically porous frameworks that corresponds to Brønsted acid sites within the catalysts owing to the silicon being isomorphously substituted into the framework via type 2 or type 3 substitutions or a combination of both. There was also an additional band at 3750 cm$^{-1}$, this is attributed to the silanol sites in the catalysts which originate from the calcination of the surfactant in the mesopores. The FTIR data therefore indicates, as did the $^{29}$Si MAS NMR (see FIG. 40A-40C), that the surfactant has been successfully incorporated into the frameworks.

Figure 43A:
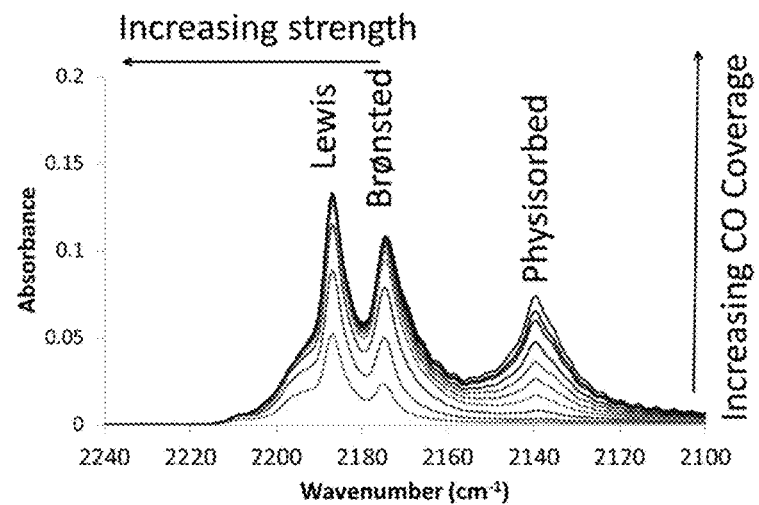
FIG. 43A is related to Example 8 and illustrates the FTIR spectra of CO adsorbed at 80 k on calcined HP Co AlPO-5.
Figure 43B:
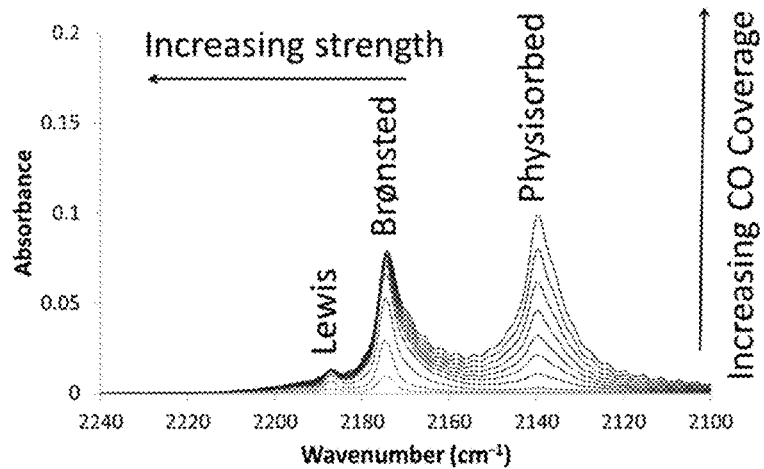
FIG. 43B is related to Example 8 and illustrates the FTIR spectra of CO adsorbed at 80 k on calcined HP Ti AlPO-5.
Figure 43C:
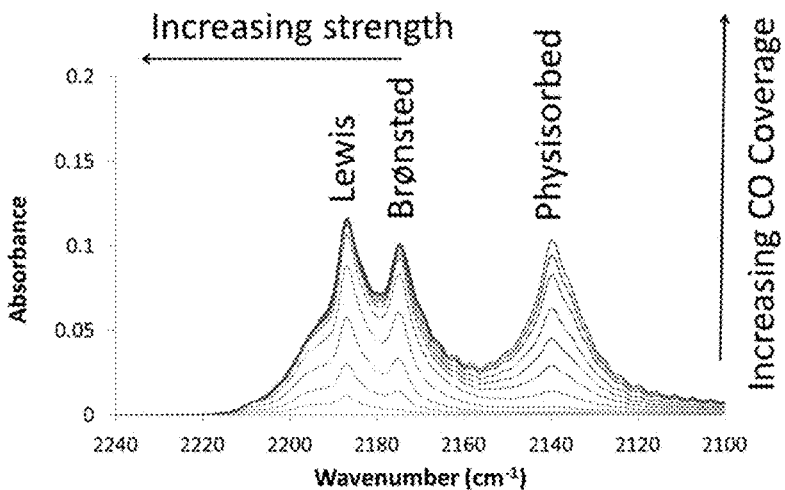
FIG. 43C is related to Example 8 illustrates the FTIR spectra of CO adsorbed at 80 k on calcined HP Co Ti AlPO-5.

FTIR spectroscopy coupled with the small basic CO probe molecule enabled the elucidation of the type and strength of acid sites present in the frameworks, as shown in FIGS. 43A-C. FIG. 43A illustrates the FTIR spectra of CO adsorbed at 80 k on calcined HP Co AlPO-5. FIG. 43B illustrates the FTIR spectra of CO adsorbed at 80 k on calcined HP Ti AlPO-5. FIG. 43C illustrates the FTIR spectra of CO adsorbed at 80 k on calcined HP Co Ti AlPO-5. Observation of the CO region of the FTIR spectra revealed that the cobalt containing catalysts (HP Co AlPO-5 and HP Co Ti AlPO-5) contained Lewis acid sites as well as Brønsted acid sites. The HP Ti AlPO-5 also had absorbance bands due to CO coordinated with both Lewis and Brønsted acid sites, although it was observed with much lower CO adsorption on Lewis acid sites compared to the cobalt containing samples, hence indicating that the HP Ti AlPO-5 has much less Lewis acidity than the cobalt containing frameworks.

Figure 44A:
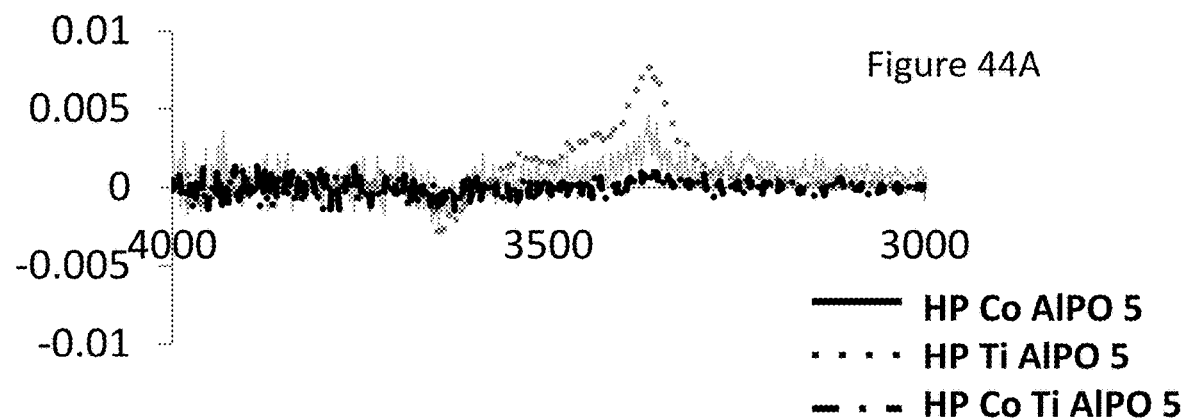
FIG. 44A is related to Example 8 and illustrates the FTIR spectra of 0.02 cc of CO adsorbed at 80K on calcined HP Co AlPO-5, calcined HP Ti AlPO-5 and calcined HP Co Ti AlPO-5.
Figure 44B:
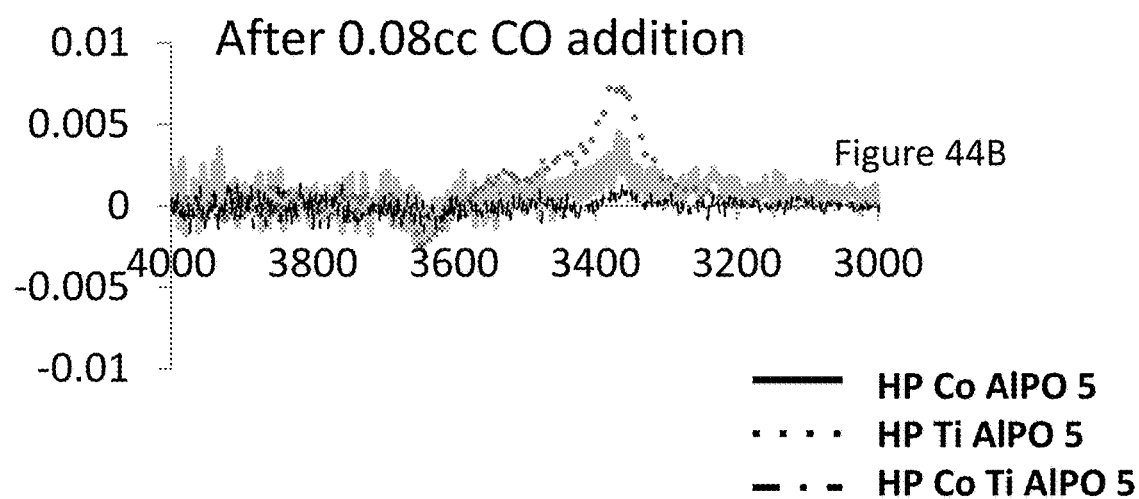
FIG. 44B is related to Example 8 and illustrates the FTIR spectra of 0.08 cc of CO adsorbed at 80K on calcined HP Co AlPO-5, calcined HP Ti AlPO-5 and calcined HP Co Ti AlPO-5.
Figure 44C:
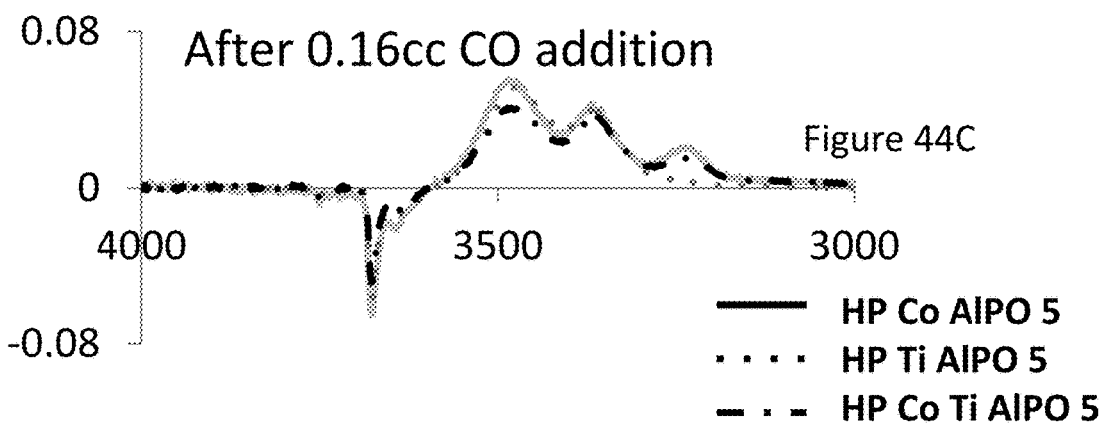
FIG. 44C is related to Example 8 and illustrates the FTIR spectra of 0.16 cc of CO adsorbed at 80K on calcined HP Co AlPO-5, calcined HP Ti AlPO-5 and calcined HP Co Ti AlPO-5.

FIGS. 44A-44C illustrate the FTIR spectra after the addition of 0.02 cc, 0.08 cc and 0.16 cc, respectively, of CO adsorbed at 80K on calcined HP Co AlPO-5, HP Ti AlPO-5, and HP Co Ti AlPO-5. As shown in FIGS. 44A-44C and Table 6, in the OH region CO adsorption resulted in a shift of the Si—OH, P—OH and Si—OH—Al bands to lower frequency.

TABLE 6

BET measurements for microporous and HP M$^{II}$M$^{III}$ AlPO-5 catalysts

| Catalyst | Bridging OH | | | | | CO Area (AU) (0.18 cc added) |
|---|---|---|---|---|---|---|
| | Before CO | After CO | Shift | After CO | Shift | |
| HP Co AlPO-5 | 3644 | 3366 | 278 | 3236 | 408 | 2.082 |
| HP Ti AlPO-5 | 3641 | 3366 | 275 | | | 0.586 |
| HP Co Ti AlPO-5 | 3642 | 3364 | 278 | 3232 | 410 | 2.098 |

As shown in FIGS. 44A-44C and Table 6, at low CO coverage all samples showed a shifted Si—OH—Al band around 3365 cm$^{-1}$ in the hydroxyl region. This resulted in a band shift between 275 and 278 cm$^{-1}$ which is typical for a SAPO catalyst. The two cobalt-containing samples also had an additional band around 3235 cm$^{-1}$ with a shift of >400 cm-1 which is attributed to the CO interacting with stronger Brønsted acid sites. At higher CO coverage ((0.08 cc), the three catalysts had an additional shifted OH band around 3470 cm$^{-1}$ due to interaction of the CO with the P—OH defect groups. At even higher CO coverage (0.16 cc) there is a small amount of attenuation of the Si—OH bands around 3745 cm$^{-1}$ for the three samples. The FTIR-CO revealed that the cobalt containing HP AlPO-5s contained considerable stronger and more acid sites than the HP Ti AlPO-5.

Figure 45:
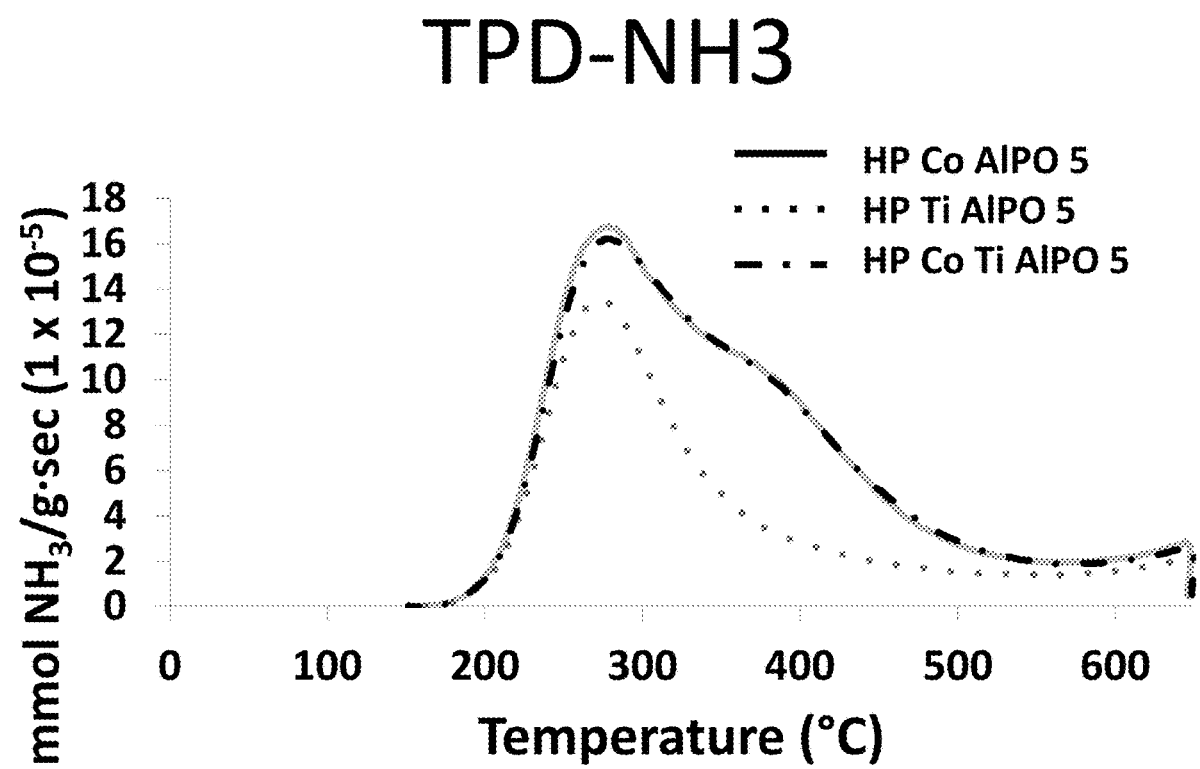
FIG. 45 is related to Example 8 and illustrates the TPD nitrogen adsorption results for HP Co AlPO-5, HP Ti AlPO-5, and HP Co Ti AlPO-5.

FIG. 45 illustrates the TPD nitrogen adsorption results for HP Co AlPO-5, HP Ti AlPO-5, and HP Co Ti AlPO-5. FIG. 45 further supports the observation above and indicates that the Cobalt containing catalysts have essentially identical acid site number and strength distributions, whereas the HP Ti AlPO-5 catalyst has significantly lower total acidity and fewer stronger sites. This is very revealing, as from $^{29}$Si NMR the local environmental of the silicon is essentially the same for the three catalysts (FIGS. 40A-40C) and from BET (FIGS. 39A and 39B) and SEM (FIG. 38A-38C) the porosity and particle sizes were ascertained to be extremely similar. Therefore these differences in acid strength and type must be originating from the dopant metals, hence highlighting the real possibilities of tuning the active sites for particular reactions.

Figure 46:
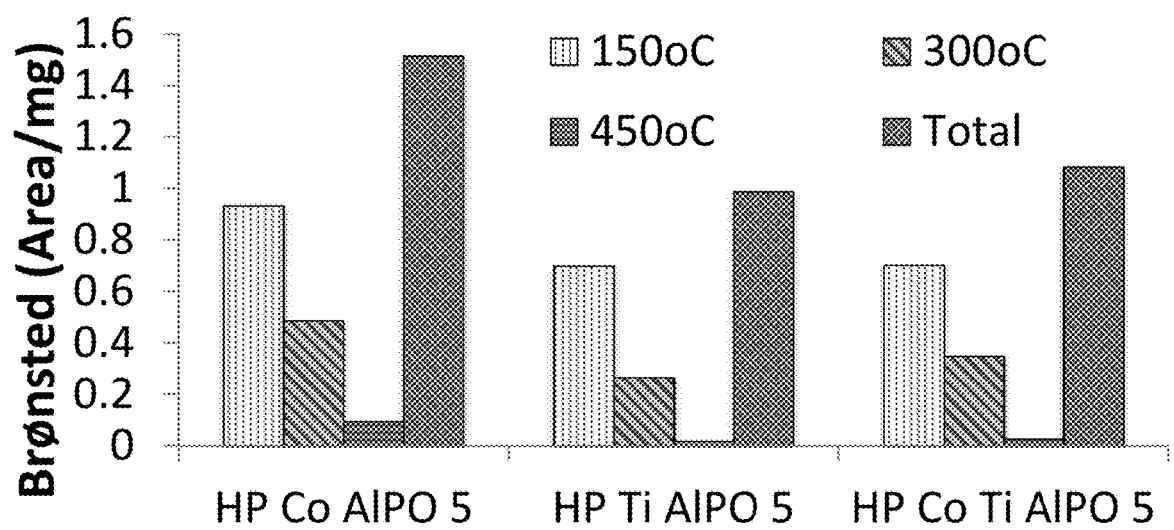
FIG. 46 is related to Example 8 and illustrates a summary of an FTIR collidine probe for HP Co AlPO-5, HP Ti AlPO-5, and HP Co Ti AlPO-5.

FIG. 46 illustrates the results of a probe with a bulkier basic probe, collidine. As shown in FIG. 46, the FTIR with a bulkier basic probe, collidine enabled the accessibility of the Brønsted acid sites as well as their strength and quantity to be assessed. Each catalyst was loaded with collidine and then heated to a certain temperature in order to investigate the strength of the acid sites. Observation of the hydroxyl region of the FTIR revealed that the collidine interacted with all the hydroxyl groups within all the catalysts and this resulted in the formation of a protonated species that has a N—H stretch around 3300 cm$^{-1}$. As the temperature of the sample with collidine was increased the collidine desorbed from the sample and very little remained after 450° C. desorption. The behavior of the three HP catalysts was very similar. The total collidine adsorption is highest on the cobalt only HP catalyst and it also had the highest number of strong sites. The strength distribution was very similar for the two cobalt-containing samples, with a higher proportion of moderate sites compared to the titanium only sample.

By employing a range of spectroscopic techniques it was possible to ascertain the various strengths and type of acid sites within the HP AlPOs. Given that the samples had analogous porosity and silicon environments it would be reasonable to assume that the differences in acidity are due to the cobalt and titanium isomorphously substituted into the framework. In order to investigate these catalysts further they were tested in catalytic reactions.

Example 9: Beckmann Rearrangement of Cyclohexanone Oxime

The Beckmann rearrangement of cyclohexanone oxime to ε-caprolactam was performed in a three necked round bottom flask under nitrogen. Benzonitrile (20 ml) was added to the flask with 0.1 g of cyclohexanone oxime, 0.1 g of chlorobenzene (internal standard) and 0.1 g of catalyst. The reaction was performed at 130° C. and aliquots were taken frequently in order to monitor the course of the reaction. The solutions were centrifuged and analyzed by Perkin Elmer Calrus 480 GC using an Elite-5 column and Flame Ionization Detector. The products were identified and quantified by using cholorbenzene as an internal standard and employing the calibration method.

It was ascertained from the spectroscopic investigations that all three HP catalysts contained Brønsted acid sites, with the cobalt containing sites also having some Lewis acidity. Therefore the industrially significant Beckmann rearrangement was chosen as the probe reaction to investigate the catalysts active sites further. This transformation is used to convert cyclic oximes into the lactam monomeric building blocks for Nylon synthesis. It is well known that weak Brønsted acid sites are preferred for this reaction with stronger sites and Lewis acid sites often promoting the formation of the unwanted ketone. Therefore the nature of the acid sites within the HP AlPOs should affect their catalytic activity and selectivity.

Figure 47A:
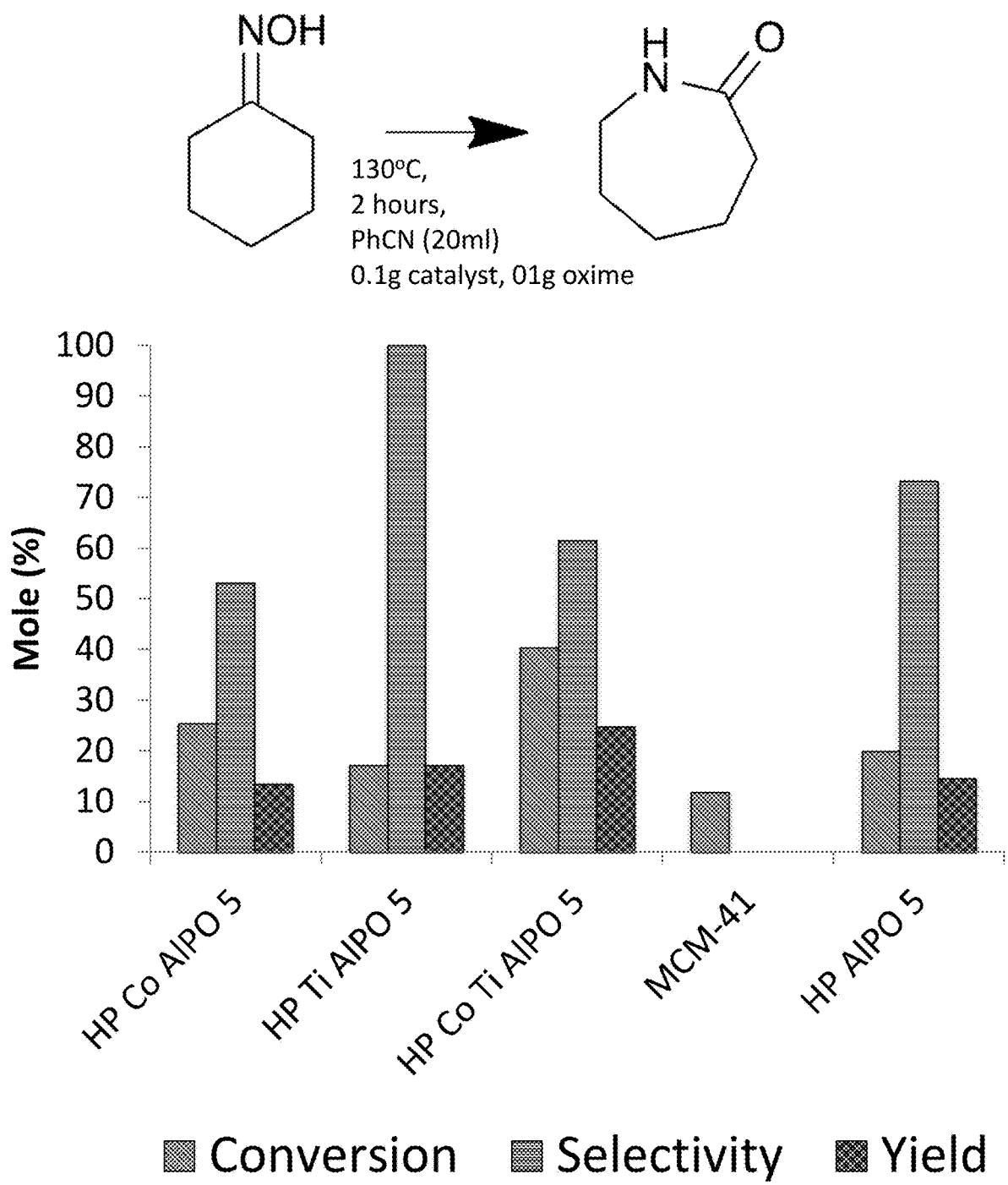
FIG. 47A is related to Example 9 and illustrates the percent conversion, percent selectivity, and percent yield for the liquid phase Beckmann rearrangement of cyclohexanone oxime to ε-caprolactam for various catalysts.

All three of the HP AlPO catalysts were active in the liquid phase Beckmann rearrangement. FIG. 47A illustrates the percent conversion, percent selectivity, and percent yield for the liquid phase Beckmann rearrangement of cyclohexanone oxime to ε-caprolactam for various catalysts. The reaction was performed using 0.1 g cyclohexanone oxime, 0.1 g catalyst, 0.1 g chlorobenzene (IS), 20 ml anhydrous PhCN, 130° C. under nitrogen for 7 hours. The HP Ti AlPO-5 was 100% selective towards the desired product, ε-caprolactam. Both HP Co AlPO5 and HP Co Ti AlPO-5 produced cyclohexanone as a by-product. Without wishing to be held to any particular theory, the formation of cyclohexanone is thought to be due to Lewis acidity as well as stronger acid sites being present, which both HP Co AlPO-5 and HP Co Ti AlPO-5 have (FIGS. 40A-40C). Interestingly though the HP Co Ti AlPO-5 is more selective than the HP Co AlPO-5 even though both have near identical acid strength and quantity. The HP Co Ti AlPO-5 also has the highest conversion at 71% and hence the largest yield of ε-caprolactam at 39%, with the HP Ti AlPO-5 that has 100% selectivity with a lower yield of 29%. These differences between the two catalysts could be due to synergy between the Co and Ti sites. From DR UV/Ms (FIG. 41) it was speculated that the titanium was more tetrahedral in nature in the bimetallic HP catalyst. This more tetrahedral nature may be more amenable for the catalysis and therefore lead to higher conversions and hence higher yields of ε-caprolactam.

As shown in FIG. 47A, the hierarchical porous catalysts demonstrate high activity and improved selectives in catalytic performance.

Figure 47B:
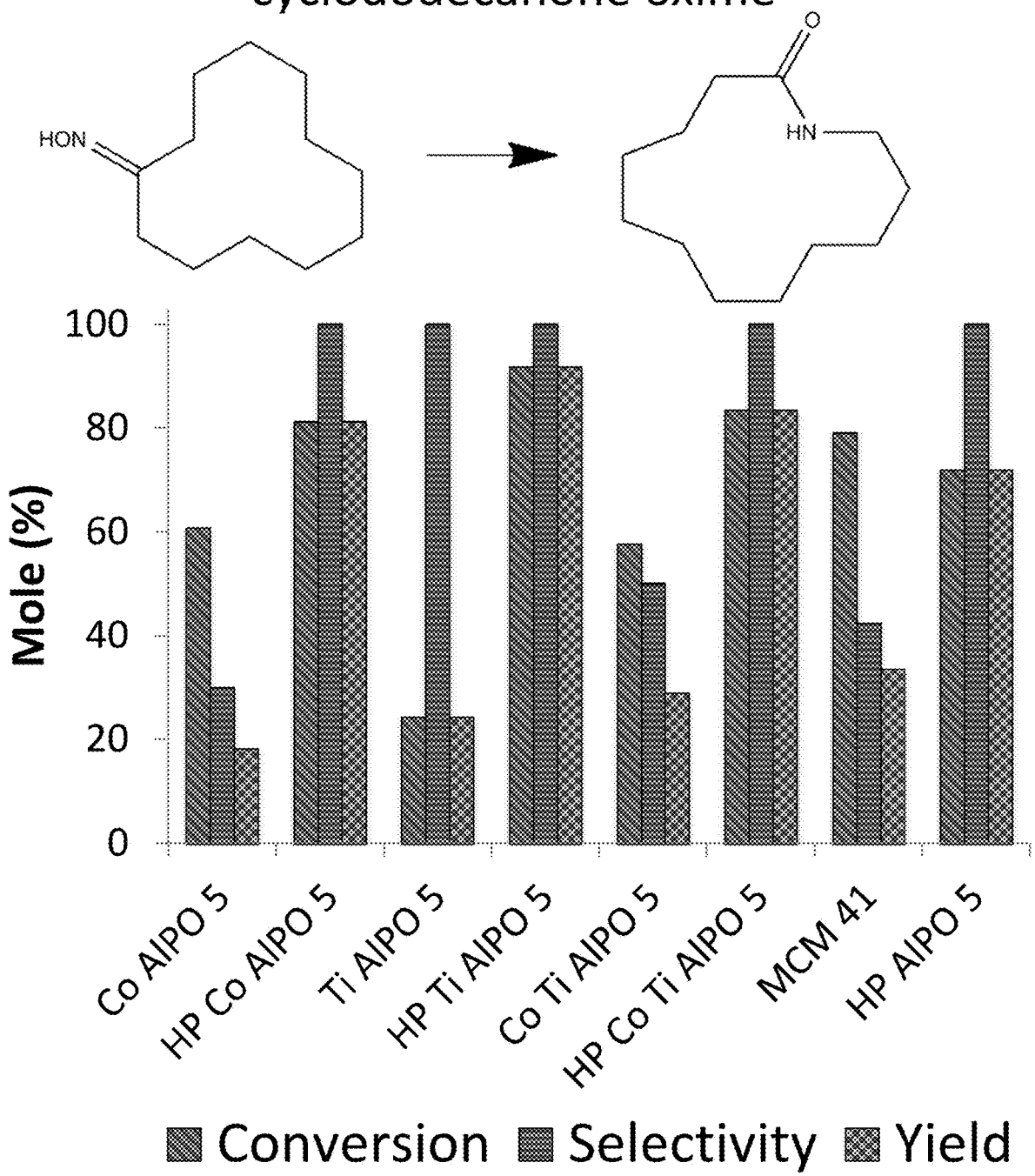
FIG. 47B is related to Example 9 and illustrates the percent conversion, percent selectivity, and percent yield for the liquid phase Beckmann rearrangement of cyclododecanone oxime to laurolactam for various catalysts.

Referring next to FIG. 47B, In order to further test the efficacy of the HP catalysts a larger substrate, cyclododecanone oxime (0.9 nm) was utilized in the Beckmann rearrangement to laurolactam, precursor to industrially significant Nylon 12. The reaction carried out was the liquid phase Beckmann rearrangement of cyclododecanone oxime to laurolactam under reaction conditions of 0.1 g cyclohexanone oxime, 0.1 g catalyst, 0.1 g chlorobenzene (IS), 20 ml anhydrous PhCN, 130° C. under nitrogen, for 2 hours. As shown in FIG. 47B, the hierarchically porous catalysts were far more active than the microporous catalysts Cyclododecanone oxime (0.9 nm) is larger than the micropores of AlPO-5 (0.7 nm), therefore seeing as the microporous catalysts are active in this rearrangement it is likely that both external and internal sites are active for this reaction. The hierarchically porous catalysts will have both external and internal sites accessible to the substrate leading to extremely high conversions after just two hours (92% for HP Ti AlPO-5) whereas in the case of the microporous analogue only the external sites will be available and hence a lower conversion is observed (just 24% for Ti AlPO-5). In this reaction the hierarchically porous catalysts all have very high conversions 81-92% with 100% selectivity. In order to elucidate the origin for the high conversions both MCM 41 and HP AlPO-5 were tested in this reaction. Unlike in the rearrangement of cyclohexanone oxime, MCM 41 was active in this reaction and was able to form laurolactam, likewise HP AlPO-5 was also active. Although they both were not as successful as the multi-metallic HP AlPO-5, therefore highlighting the importance of the metals within the framework to subtly tune the intrinsic nature of the active site for a particular reaction.

While the present disclosure is primarily directed to Beckmann rearrangement of cyclohexanone oxime, cyclooctanone oxime, and cyclododecanone oxime to their corresponding lactams, it should be understood that the features disclosed herein have application to the production of other lactams and other monomers.

While this invention has been described as relative to exemplary designs, the present invention may be further modified within the spirit and scope of this disclosure. Further, this application is intended to cover such departures from the present disclosure as come within known or customary practice in the art to which this invention pertains.

What is claimed is:

1. A method of making a catalyst for a Beckmann rearrangement reaction, wherein the catalyst is a hierarchical porous catalyst with a silicoaluminophosphate framework, a plurality of interconnected micropores, and a plurality of mesopores interconnected with the micropores, the method comprising:

combining an organosilane surfactant, at least one structure directing agent, a metal precursor, a silicon source, phosphoric acid, and water to form a mixture; wherein combining the organosilane surfactant, the structure directing agent, the metal precursor, the silicon source, the phosphoric acid, and the water to form the mixture includes:

mixing the metal precursor and the at least one structure directing agent together;

adding the silicon source to the mixture of the metal precursor and the at least one structure directing agent;

adding the organosilane surfactant to the mixture after adding the silicon source;

adding the water to the mixture after adding the organosilane surfactant; and adding the phosphoric acid to the mixture after adding the water;

heating the mixture to form a solid; and calcining the solid to form the catalyst, wherein the organosilane surfactant includes dimethyloctadecyl[3-(trimethoxysilyl)propyl]ammonium chloride and the metal precursor includes aluminum;

wherein the catalyst is a hierarchical SAPO-34 catalyst.

2. The method of claim 1, wherein the at least one structure directing agent includes tetramethylammonium hydroxide.

3. The method of claim 1, wherein the silicon source includes fumed silica.

4. The method of claim 1, wherein the metal precursor includes aluminum isopropoxide.

5. The method of claim 1, wherein the mesopores have a pore diameter from 15 Å to 50 Å.

6. The method of claim 1, wherein the micropores have a pore diameter from 3 Å to 10 Å.

7. A method of making a catalyst for a Beckmann rearrangement reaction, wherein the catalyst is a hierarchical porous catalyst with a silicoaluminophosphate framework, a plurality of interconnected micropores, and a plurality of mesopores interconnected with the micropores, the method comprising:

combining an organosilane surfactant, at least one structure directing agent, a metal precursor, a silicon source, phosphoric acid, and water to form a mixture; wherein combining the organosilane surfactant, the structure directing agent, the metal precursor, the silicon source, the phosphoric acid, and the water to form the mixture includes:

mixing the metal precursor and the phosphoric acid together with a portion of the water to form a first solution;

adding the organosilane surfactant to the at least one structure directing agent to form a second solution;

adding the silicon source to the second solution; and adding the second solution including the silicon source to the first solution to form the mixture;

heating the mixture to form a solid; and calcining the solid to form the catalyst, wherein the organosilane surfactant includes dimethyloctadecyl[3-(trimethoxysilyl)propyl]ammonium chloride and the metal precursor includes aluminum;

wherein the catalyst is a hierarchical SAPO-37 catalyst.

8. The method of claim 7, wherein the at least one structure directing agent includes tetramethylammonium hydroxide and tetrapropylammonium hydroxide.

9. The method of claim 7, wherein the silicon source includes fumed silica.

10. The method of claim 7, wherein the metal precursor includes boehmite.

11. The method of claim 7, wherein the mesopores have a pore diameter from 15 Å to 50 Å.

12. The method of claim 7, wherein the micropores have a pore diameter from 3 Å to 10 Å.

* * * * *